US009133488B2

(12) United States Patent
Green et al.

(10) Patent No.: US 9,133,488 B2
(45) Date of Patent: Sep. 15, 2015

(54) SYNTHETIC METHODS AND COMPOUNDS RELATED THERETO

(71) Applicant: University of Alaska Fairbanks, Fairbanks, AK (US)

(72) Inventors: Thomas K. Green, Fairbanks, AK (US); Zhipeng Dai, Fairbanks, AK (US)

(73) Assignee: University of Alaska Fairbanks, Fairbanks, AK (US)

( * ) Notice: Subject to any disclaimer, the term of this patent is extended or adjusted under 35 U.S.C. 154(b) by 0 days.

(21) Appl. No.: 14/144,044

(22) Filed: Dec. 30, 2013

(65) Prior Publication Data
US 2015/0184206 A1    Jul. 2, 2015

(51) Int. Cl.
C12P 7/62      (2006.01)
C07C 241/02    (2006.01)
C07D 319/06    (2006.01)

(52) U.S. Cl.
CPC ............... *C12P 7/62* (2013.01); *C07C 241/02* (2013.01); *C07D 319/06* (2013.01)

(58) Field of Classification Search
None
See application file for complete search history.

(56) References Cited

U.S. PATENT DOCUMENTS

| | | | |
|---|---|---|---|
| 3,040,079 A | 6/1962 | Joly | 260/429.9 |
| 5,559,030 A | 9/1996 | Matsuyama et al. | 435/280 |
| 5,599,963 A | 2/1997 | Carreira | 556/33 |
| 5,700,670 A | 12/1997 | Yamagishi et al. | 435/128 |
| 5,891,685 A | 4/1999 | Yamagishi et al. | 435/1.32 |
| 2010/0035959 A1 | 2/2010 | Zipkin et al. | 514/428 |

FOREIGN PATENT DOCUMENTS

| | | |
|---|---|---|
| WO | WO 2005/017135 | 2/2005 |
| WO | WO 20131057468 | 4/2013 |

OTHER PUBLICATIONS

Zhou. Nature Chemical Biology, 2012, 8, 331-333.*
Ahn, et al. "Induction of apoptosis by sphingosine, sphinganine, and c2-cennide in human colon cancer cells, but not by c2-dihydroceramicle." Anticancer Research, v. 30. pp. 2881-2884 (2010).
Ahn, et al. "Evaluation of sphinganine and sphingosine as human breast cancer chemotherapeutic and chemopreventive agents." Experimental Biology and Medicine, v. 231, pp. 1664-1672 (2006).
Akutagawa, S., et al. "Asymmetric synthesis by metal binap catalysts." Applied Catalysis a: General, v. 128(2), pp. 171-207 (1995).
Arai, N., et al. "Highly enantioselective hydrogenation of aryl vinyl ketones to allylic alcohols catalyzed by the tol-binap/dmapen ruthenium(II) complex." Angewandte Chemie, Int. Ed., v. 47, pp. 7457-7460 (2008).
Bajwa, N., Jennings, M.P., "An Efficient 1,2-Chelation-Controlled Reduction of Protected Hydroxy Ketones via Red-Al," The Journal of Organic Chemistry vol. 73, 3638-41 (2008).
Bartke, N.; Hannun, "Bioactive sphingolipids: metabolism and function" Y. A. J. Lipid Res. 2009, 50, S91.
Baskar, B., et al. "Asymmetric reduction of alklyl 2-oxo-4-arylbutanoates and -but-3-enoates by *candida parapsilosis* atcc 7330: assignment of the absolute configuration of ethyl 2-hydroxy-4-(p-methylphenyl)but-3-enoate by h nmr." Tetrahedron: Asymmetry, v. 15(24), pp. 3961-3966 (2004).
Bodalski, et al. "A new efficient synthesis of substituted nazarov reagents. A wittig-horner-emmons approach."Tetrahedron Letters, v. 21(23), pp. 2287-2290 (1980).
Brown, M.S., et al. "The reduction of esters with sodium borohydride." Journal of Organic Chemistry, v. 28, pp. 3261-3263 (1963).
Burk, M.J., et al. "Highly enantioselective hydrogenation of .beta.-keto esters under mild conditions." Journal of the American Chemical Society, v. 117, pp. 4423-4424 (1995).
Cai, et al. "A general, efficient and stereospecific route to sphingosine, sphinganines, phytosphingosines and their analogs." Organic & Biomolecular Chemistry, v. 4, pp. 1140-1146 (2006).
Carreira, et al. "Catalytic, enantioselective aldol additions with methyl and ethyl acetate o-silyl enolates: a chiral tridentate chelate as a ligand for titanium(IV)." Journal of the American Chemical Society, v. 116, pp. 8837-8838 (1994).
Chandrasekhar, et al. "Practical and highly stereoselective approaches to the total synthesis of (-)-codonopsinine." Tetrahedron: Asymmetry, v. 17, pp. 1380-1386 (2006).
Chaudhuri, et al. "Systematic investigations on the reduction of 4-aryl-4-oxoesters to 1-aryl-1,4-butanediols with methanolic sodium borohydride." Beilstein Journal of Organic Chemistry, v. 6, pp. 748-755 (2010).
Chinnababu, B., et al., "Stereoselective concise total synthesis of leodomycin C and D," Synthesis, 44(2), pp. 311-315 (2012).
Chun, J.; Hartung, H. P. "Mechanism of Action of Oral Fingolimod (FTY720) in Multiple Sclerosis" Clin. Neuropharmacol. 2010, 33, 91.
Chun, J.; He, L.; Byun, H. S.; Bittman, R. "Synthesis of ceramide analogues having the C(4)-C(5) bond of the long-chain base as part of an aromatic or heteroaromatic system" J. Org. Chem. 2000, 65, 7634.
Claridge, T. D.; Davies, S. G.; Polywka, M. E.; Roberts, P. M.; Russell, A. J.; Savory, E. D.; Smith, A. D. "Pure by NMR" Org. Lett. 2008, 10, 5433.
Clemens, J. J.; Davis, M. D.; Lynch, K. R.; Macdonald, T. L. "Synthesis of para-alkyl aryl amide analogues of sphingosine-1-phosphate: Discovery of potent Sip receptor agonists" Bioorg. Med. Chem. Lett. 2003, 13, 3401.
Corey, E.J., et al., "Highly enantioselective borane reduction of ketones catalyzed by chiral oxazaborolidines. Mechanism and synthetic implications," J. Am. Chem. Soc., vol. 109, pp. 5551-5553 (1987).
Corey, E.J., et al. "A stable and easily prepared catalyst for the enantioselective reduction of ketones. applications to multistep synthesis" J. Am. Chem. Soc., vol. 109, pp. 7925-7926 (1987).

(Continued)

Primary Examiner — Noble Jarrell
(74) Attorney, Agent, or Firm — Ballard Spahr LLP

(57) ABSTRACT

Disclosed herein are synthetic methods and compounds related to the compounds that are useful as or in the production of biologically active compounds. Stereoselective and stereospecific synthetic methods are disclosed to produce compounds, such as, for example, γ,δ-unsaturated-β-hydroxyesters and aminated derivatives thereof, at high yields with desired stereochemistry. This abstract is intended as a scanning tool for purposes of searching in the particular art and is not intended to be limiting of the present invention.

20 Claims, 28 Drawing Sheets

(56) References Cited

OTHER PUBLICATIONS

Corey, E.J., et al., "Reduction of Carbonyl Compounds with Chiral Oxazaborolidine Catalysts: A New Paradigm for Enantioselective Catalysis and a Powerful New Synthetic Method," Angew. Chem. Int. Ed., vol. 37, pp. 1986-2012 (1998).
Curfman, C.; Liotta, D. "Synthesis of sphingosine and sphingoid bases" Methods Enzymol. 2000, 311, 391.
Dai, et al. Stereoselective synthesis of aryl γ, δ-unsaturated β-hydroxyesters by ketoreductases. Molecular Catalysis B: Enzymatic, 97 (1), 264-269 (2013).
Dondoni, et al., "Stereoselective mono- and bis-homologation of L-serinal via 2-trimethylsilylthiazole addition. The thiazole route to amino L-sugars and D-erythrosphingosines," Journal of the Chemical Society, Chemical Communications, pp. 10-12 (1988).
du Pisani, et al., "Ethyl 4-(diethoxyphosphinyl)-3-oxobutanoate: Selective synthesis of beta-keto phosphonates," Synthetic Communications, vol. 32, pp. 305-314 (2002).
Edsall, et al., "N,N-dimethylsphingosine is a potent competitive inhibitor of sphingosine kinase but not of protein kinase C: modulation of cellular levels of sphingosine 1-phosphate and ceramide," Biochemistry-Us, vol. 37, pp. 12892-12898 (1998).
Frater, G., et al., "The Stereoselective α-Alkylation of Chiral β-Hydroxy Esters and some Application Thereof," Tetrahedron, vol. 40, pp. 1269-1277 (1984)., vol. 19, pp. 1941-46 (2008).
Fuglseth, E., et al. "Asymmetric reduction using (R)-MeCBS and determination of absolute configuration of para-substituted 2-fluoroarylethanols," Tetrahedron: Asymmetry, vol. 19, pp. 1941-1946 (2008).
Garner, et al., "A Stereodivergent Synthesis of D-erythro-Sphingosine and D-threoSphingosine from L-Serine," The Journal of Organic Chemistry, vol. 53, pp. 4395-4398 (1988).
Genet, J.P., et al., "Dynamic kinetic resolution of cyclic β-ketoesters with preformed or prepared in situ chiral diphosphine-ruthenium (II) catalysts," Tetrahedron Lett., vol. 35, pp. 4559-4562 (1994).
Genet, J.P., et al., "Novel, general synthesis of the chiral catalysts diphosphine-ruthenium (II) diallyl complexes and a new practical in situ preparation of chiral ruthenium (II) catalysts," Tetrahedron: Asymmetry., vol. 5, pp. 665-674 (1994).
Genet, J.P., et al., "Enantioselective hydrogenation reactions with a full set of preformed and prepared in situ chiral diphosphine-ruthenium (II) catalysts," Tetrahedron: Asymmetry, vol. 5, pp. 675-690 (1994).
Genet, J.P., "New asymmetric syntheses of βhydroxy α-amino acids and analogues. Components of Biologically Active Cyclopeptides," Pure & Appl. Chem, vol. 88, pp. 593-596 (1996).
Girard, a., et al., "Syntheses of the syn and anti α-amino-β-hydroxy acids of vancomycin: (2S, 3R) and (2R, 3R) p-chloro-3-hydroxytyrosines," Tetrahedron Lett., vol. 37, pp. 7967-7970 (1996).
Greck, C., "Asymmetric-synthesis of anti n-boc-alpha-hydrazino-beta-hydroxyestersfrom beta-ketoesters by sequential catalytic-hydrogenation and electrophilic amination," Synlett, v. 1993(7), pp. 475-477 (1993).
Greck, et al., Synthesis of (3s, 4s)-4-Hydroxy-2, 3, 4, 5-Tetrahydropyridazine-3-Carboxylic Acid, Component of Luzopeptin A, Tetrahedron: Asymmetry, vol. 6, pp. 1989-1994 (1993).
Greek, et al., "Synthesis of both enantiomers of trans 3-hydroxypipecolic acid," Tetrahedron Lett., vol. 37, pp. 2031-2034 (1996).
Greek, C. And Genet, J.P., "Electrophilic amination: new synthetic applications," Synlett, p. 741 (1997).
Hasegawa, "Synthesis of α-diazo-β-hydroxyesters through a one-pot protocol by phase-transfer catalysis: application to enantioselective aldol-type reaction and diastereoselective synthesis of α-amino-β-hydroxyester derivatives," *Tetrahedron*, vol. 62, pp. 1390-1401 (2006).
Hannun, et al. "The Ceramide-centric Universe of Lipid-mediated Cell Regulation: Stress Encounters of Lipid Kind," *Journal of Biological Chemistry*, v. 277, pp. 25847-25850 (2002).

Hannun and Obeid, "Principles of Bioactive Lipids Signalling: Lessons from Sphingolipids," *Nat. Rev. Mol. Cell Biol.*, vol. 9, pp. 139-150 (2008).
Herold, P. Synthesis of D-erythro- and D-threo-Sphingosine Derivatives from L-Serine, Helv. Chim. Acta 71, pp. 354-362 (1998).
Hopkins, C.D., et al., "Total Synthesis of (-)-CP2-Disorazole C1," Org. Lett., vol. 13, pp. 4088-4091 (2011).
Hoye, et al., "Mosher ester analysis for the determination of absolute configuration of stereogenic (chiral) carbinol carbons," Nat. Protoc., vol. 2, pp. 2451-2458 (2007).
Hu, a., et al., "Remarkable 4,4'-Substituent Effects on Binap: Highly Enantioselective Ru Catalysts for Asymmetric Hydrogenation of β-Aryl Ketoesters and Their Immobilization in Room-Temperature Ionic Liquids," Angew. Chem., Int. Ed. vol. 43, pp. 2501-2504 (2004).
Huisman, G.W., et al., "Practical chiral alcohol manufacture using ketoreductases," Curr. Opin. Chem. Biol., vol. 14, pp. 122-129 (2010).
Hummel, "Dehydrogenases for the synthesis of chiral compounds," Eur. J. Biochem., vol. 184, pp. 1-13 (1989).
Ishihara, K., et al., "Stereocontrolled Reduction of α- and β-Keto Esters with Micro Green Algae, Chlorella Strains," Biosci., Biotechnol., Biochem., vol. 64, pp. 2099-2103 (2000).
Jaramillo, M.; Kirschner, D. L.; Dai, Z. P.; Green, T. K. "Separation of sulfoalkylated cyclodextrins with hydrophilic interaction liquid chromatography" J. Chromatogr. A 2013, 1316, 92.
Kalaitzakis, D, et al., "Highly stereoselective reductions of α-alkyl-1,3-diketones and α-alkyl-β-keto esters catalyzed by isolated NADPH-dependent ketoreductases," Organic Letters, vol. 7, pp. 4799-4801 (2005).
Kalaitzakis, D., et al., "Stereoselective chemoenzymatic synthesis of sitophilate: a natural pheromone," Tetrahedron: Asymmetry, vol. 18, pp. 2418-2426 (2007).
Kaluzna, I.A., et al., "Systematic investigation of Saccharomyces cerevisiae enzymes catalyzing carbonyl reductions," J. Am. Chem. Soc., vol. 126, pp. 12827-12832 (2004).
Kambourakis, S., et al., "Ketoreductases in the synthesis of valuable chiral intermediates: application in the synthesis of α-hydroxy β-amino and β-hydroxy γ-amino acids," Tetrahedron, vol. 60, pp. 663-669 (2004).
Kawanami, et al., "Practical enantioselective reduction of ketones using oxazaborolidine catalyst generated in situ from chiral lactam alcohol and borane," Tetrahedron, vol. 59, pp. 8411-8414 (2003).
Kim, et al., "Reduction of aromatic and aliphatic keto esters using sodium borohydride/MeOH at room temperature: a thorough investigation," Tetrahedron, vol. 66, pp. 3995-4001 (2010).
Kim, K., et al. "Synthesis and cytotoxicity of new aromatic ceramide analogs with alkylsulfonamido chains" Arch. Pharm. Res. 2007, 30, 570.
Kim, J. W., et al. "Synthesis and evaluation of sphingoid analogs as inhibitors of sphingosine kinases" Bioorg. Med. Chem. 2005, 13, 3475.
Kirschner, D., et al., "Fine tuning of sulfoalkylated cyclodextrin structures to improve their mass-transfer properties in an aqueous biphasic hydroformylation reaction ," J. Mol. Catal. A: Chem, vol. 286, pp. 11-20 (2008).
Kobayashi, et al., "Enantioselective syntheses of d-erythro-sphingosine and phytosphingosine from simple achiral aldehydes using catalytic asymmetric aldol reactions as key steps," Tetrahedron Letters, vol. 35, pp. 9573-9576 (1994).
Kumar, et al., "A general and concise asymmetric synthesis of sphingosine, safingol and phytosphingosines via tethered aminohydroxylation," Organic & Biomolecular Chemistry, vol. 8, pp. 5074-5086 (2010).
Labeeuw, et al., "A short total synthesis of sulfobacin A," Tetrahedron Letters, vol. 44, pp. 6383-6386 (2003).
Lahmar, N., "A general route to α-alkyl (E)-α,(β-unsaturated aldehydes," Journal of Organometallic Chemistry, vol. 691, pp. 3018-3026 (2006).
Li, D., et al., "Turnagainolides A and B, cyclic depsipeptides produced in culture by a *Bacillus sp.*: isolation, structure elucidation, and synthesis," J. Nat. Prod., vol. 74, pp. 1093-1099 (2011).

(56) References Cited

OTHER PUBLICATIONS

Lim, et al "Syntheses of sphingosine-1-phosphate analogues and their interaction with EDG/S1P receptors," Bioorg. Med. Chem. Lett. vol. 14, pp. 2499-2503 (2004).
Liao, J.Y.; Tao, J. H.; Lin, G. Q.; Liu, D. G. "Chemistry and biology of sphingolipids" Tetrahedron 2005, 61, 4715.
Lim, et al., "FTY720 analogues as sphingosine kinase 1 inhibitors enzyme inhibition kinetics, allosterism, proteasomal degradation, and actin rearrangement in MCF-7 breast cancer cells," Journal of Biological Chemistry, vol. 286, pp. 18633-18640 (2011).
Llaveria, et al., "An efficient and general enantioselective synthesis of sphingosine, phythosphingosine, and 4-substituted derivatives," Organic Letters, vol. 11, pp. 205-208 (2008).
Ma, X., et al., "Ru-catalyzed highly chemo- and enantioselective hydrogenation of γ-halo-γ,δ-unsaturated-β-keto esters under neutral conditions," Chem. Commun., vol. 48, pp. 5352-5354 (2012).
Magnus, et al., "Synthesis of carbamates from diethoxycarbonyl hydrazine derivatives by E1cB eliminative cleavage of the N-N'-bond rather than reduction.," Org. Lett., vol. 11, pp. 56465648 (2009).
Mathre, D.J., et al., "A practical process for the preparation of tetrahydro-1-methy-3,3-diphenyl-1H,3H-pyrrolo[1,2-c][1,3,2]oxazaborole-borane. A highly enantioselective stoichiometric and catalytic reducing agent," J. Org. Chem., vol. 58, pp. 2880-2888 (1993).
Matsuda, T., et al., "Recent progress in biocatalysis for asymmetric oxidation and reduction," Tetrahedron: Asymmetry, vol. 20, pp. 513-557 (2009).
Milstein, et al., "Targeting Sphingosine-1-phosphate: A Novel Avenue for Cancer Therapeutics," Cancer Cell, v. 9, pp. 148-150 (2006).
Moorhoff, C.M., "An efficient separation method for enol phosphate and corresponding-ketophosphonate from their mixtures under aqueous conditions," Synthetic Communications, vol. 33, pp. 2069-2086 (2003).
Moorhoff, et al., "Comments on the reaction of ethyl 4-(diethoxyphosphinyl)-3-oxobutanoate and related phosphonate esters with enals," Tetrahedron Letters, vol. 28, pp. 559-562 (1987).
Morad, S. A.; Cabot, M. C. "Ceramide-orchestrated signalling in cancer cells" Nat. Rev. Cancer 2013, 13, 51.
Moreno, et al., "Enantioselective synthesis of sphingadienines and aromatic ceramide analogs,"Organic Letters, vol. 13, pp. 5184-5187 (2011).
Mori, K.; Tashiro, T. "Spihngolipids and glycosphingolipids—their syntheses and bioactivities" Heterocycles 2011, 83, 951.
Murahashi, S-I., et al., "Palladium-catalyzed decarbonylation of acyl cyanides," Journal of Organic Chemisty, vol. 51, pp. 898-901 (1986).
Murakami, T.; Furusawa, K. "Efficient stereodivergent synthesis of erythro- and threo-sphingosines: unprecedented reversal of the stereochemistry in the addition" Tetrahedron 2002, 58, 9257.
Murakami et al., "Synthesis and biological properties of novel sphingosine derivatives," Bioorg. Med. Chem. Lett., vol. 15, pp. 1115-1119 (2005).
Nimkar, et al.; "A stereoselective synthesis of sphingosine, a protein kinase c inhibitor," Tetrahedron Letters, vol. 29, pp. 3037-3040 (1988).
Nussbaumer, P. "Medicinal chemistry aspects sphingolipid metabolism" ChemMedChem 2008, 3, 543.
Ogretmen, et al., "Biologically Active Phingolipids in Cancer Pathogenesis and Treatment," Nature Reviews Cancer, vol. 4, pp. 604-616 (2004).
Ohkuma, T., et al., "Asymmetric hydrogenation of alkenyl, cyclopropyl,and aryl ketones, RuCl2(xylbinap)(1,Z-diamine) as a precatalyst exhibiting a wide scope," J. Am. Chem. Soc., vol. 120, pp. 13529-13530 (1998).
Padhi, S.K., et al., "Deracemisation of aromatic β-hydroxy esters using immobilised whole cells of Candida parapsilosis ATCC 7330 and determination of absolute configuration by 1H NMR," Tetrahedron: Asymmetry, vol. 16, pp. 2790-2798 (2005).

Park, Y.S., et al., "Facile synthesis of β-ketoesters by indium-mediated reaction of acyl cyanides with ethyl bromoacetate under ultrasonication," Bulletin Korean Chemical Society, vol. 26, pp. 878-879 (2005).
Paugh, et al., "A selective sphingosine kinase 1 inhibitor integrates multiple molecular therapeutic targets in human leukemia," Blood, vol. 12, pp. 1382-1391 (2008).
Perry, et al., "Serine Palmitoyltransferase Regulates de Novo Ceramid Generation during Etoposide-induced Apoptosis," Journal of Biological Chemistry, vol. 275, pp. 9078-9084 (2000).
Poupardin, O., et al., "First approach to the cycloisodityrosine unit of RA-IV," Tetrahedron Letters, 42(8), pp. 1523-1526 (2001).
Pyne, et al., "Sphingosine 1-phosphate and Cancer," Cancer Research, vol. 71, pp. 6576-6582 (2011).
Radin, "Killing tumours by ceramide-induced apoptosis: a critique of available drugs," Biochem J., vol. 371, pp. 243-256 (2003).
Radunz, et al. Liebigs Annalen der Chemie, vol. 1988, pp. 1103-1105 (1988).
Reiff, E.A., et al., "Practical syntheses of the C12-C21 epothilone subunit via catalytic asymmetric reductions: Itsuno—Corey oxazaborolidine reduction and asymmetric Noyori hydrogenation," Tetrahedron Lett., vol. 45, pp. 5845-5847 (2004).
Reynolds, et al., "Ceramide Synthesis and metabolism as a target for cancer therapy," Cancer Letter, vol. 206, pp. 169-180 (2004).
Rimoldi, I., et al., "Chemo- and biocatalytic strategies to obtain phenylisoserine, a lateral chain of Taxol by asymmetric reduction," Tetrahedron: Asymmetry, vol. 22, pp. 2110-2116 (2011).
Rimoldi, I., et al., "3-(Hydroxy(phenyl)methyl)azetidin-2-ones obtained via catalytic asymmetric hydrogenation or by biotransformation," Tetrahedron: Asymmetry, vol. 22, pp. 597-602 (2011).
Saravanan, T., et al., "Stereochemical preference of Candida parapsilosis ATCC 7330 mediated deracemization: E- versus Z-aryl secondary alcohols," Tetrahedron: Asymmetry, vol. 23, pp. 1360-1368 (2012).
Schmidt, B., et al., "Ruthenium-Catalyzed Olefin Metathesis Double-Bond Isomerization Sequence," J. Org. Chem., vol. 69, pp. 7672-7687 (2004).
Schmidt, B., et al., "Total Syntheses of Naturally Occurring Seimatopolide A and Its Enantiomer from Chiral Pool Starting Materials Using a Bidirectional Strategy," J. Org. Chem., vol. 77, pp. 10897-10906 (2012).
Schroer, K., et al., "Continuous asymmetric ketone reduction processes with recombinant Escherichia coli," Biotechnol., vol. 132, pp. 438-444 (2007).
Seashore-Ludlow, B., et al., "Asymmetric transfer hydrogenation coupled with dynamic kinetic resolution in water: synthesis of anti-β-hydroxy-α-amino acid derivatives," Org. Lett., vol. 14, pp. 6334-6337 (2012).
Singer, R.A., et al., "An in situ procedure for catalytic, enantioselective acetate aldol addition. Application to the synthesis of (R)-(—)-epinephrine," Tetrahedron Letters, 38(6), pp. 927-930 (1997).
Smrcina, M., et al., "A Facile Synthesis of 2—Amino 2'—hydroxy—1,1—binaphthyl and 2,2'—Diamino—1,1'—binaphthyl by Oxidative Coupling Using Copper (II) Chloride" Synlett, pp. 231-232 (1991).
Spiegel, et al., "Sphingosine-1-phosphate: An Enigmatic Signalling Lipid," Nat. Rev. Mol. Cell Bio., v. 4, pp. 397-407 (2003).
Svendsen, "Naturally occuring lactones and lactames—V : Halogenated β-keto esters as starting materials for the synthesis of tetronic acids," Tetrahedron, vol. 29, pp. 4251-4258 (1973).
Taber, D.F., et al., "Enantioselective reduction of β-keto esters," Tetrahedron Lett., vol. 32, pp. 4227-4230 (1991).
Toure, B.B. and D.G. Hall, "Design of a Nonreductive Method for Chemoselective Cleavage of Hydrazines in the Presence of Unsaturations: Application to a Stereoconvergent Three-Component Synthesis of (-)-Methyl Palustramate," The Journal of Organic Chemistry, vol. 69, pp. 8429-8436 (2004).
Turner, N.J., et al., "Directed evolution drives the next generation of biocatalysts," Nat. Chem. Biol., vol. 5, pp. 568-574 (2009).
Van den Berg, et al., "A Rapid and Efficient Synthesis of D-erythro-Sphingosine from D-ribo-Phytosphingosine," European Journal of Organic Chemistry, vol. 2011, pp. 6685-6689 (2011).

(56) References Cited

OTHER PUBLICATIONS

Van den Berg, et al., "A simple and low cost synthesis of d-erythro-sphingosine and d-erythro-azidosphingosine from d-ribo-phytosphingosine: glycosphingolipid precursors," Tetrahedron Letters, vol. 43, pp. 8409-8412 (2002).

Van Den Goorbergh, J.A.M., et al., "Ethyl 4-diphenylphosphinoyl-2-oxobutanoate: A convenient reagent for the synthesis of γ,δ-unsaturated β-ketoesters," Tetrahedron Letters, vol. 21, pp. 3621-3624 (1980).

Van Overmeire, et al., "Effect of Aromatic Short-Chain Analogues of Ceramide on Axonal Growth in Hippocampal Neurons," J. Med. Chem., vol. 42, pp. 2697-2705 (1999).

Voight, E.A., et. al. (2006) "Efficient preparation of chiral diamines via Red-Al reduction of N-Boc-protected amino acid-derived secondary amides," Tetrahedron Letters, vol. 47, 1717-20 (2006).

Wong, et al., "Synthesis and evaluation of sphingosine analogues as inhibitors of sphingosine kinases," J. Med. Chem., vol. 52, pp. 3618-3626 (2009).

Wymann, et al., "Lipid signalling in disease," Nat. Rev. Mol. Cell Biol., vol. 9, pp. 162-176 (2008).

Yang, et al., "A concise and scalable synthesis of high enantiopurity (-)-D-erythro-sphingosine using peptidyl thiol ester-boronic acid cross-coupling," Organic Letters, vol. 9, pp. 2993-2995 (2007).

Yatomi, et al., "N,N-Dimethylsphingosine Inhibition of Sphingosine Kinase and Sphingosine 1-Phosphate Activity in Human Platelets," Biochemistry-Us, vol. 35, pp. 626-633 (1996).

Zemmouri, R., et al., "Palladium-Catalyzed Stereoconvergent Formylation of (E/Z)-β-Bromo-β-fluorostyrenes: Straightforward Access to (Z)-α-Fluorocinnamic Aldehydes and (Z)-β-Fluorocinnamic Alcohols," Journal of Organic Chemistry, vol. 76, pp. 7691-7698 (2011).

Zhang, Z, et al., "Synthesis of Chiral Bisphosphines with Tunable Bite Angles and Their Applications in Asymmetric Hydrogenation of β-Ketoesters," J. Org. Chem., vol. 65, pp. 6223-6226 (2000).

Zhou, H., et al. A fungal ketoreductase domain that displays substrate dependent stereoselectivity. Nature Chemical Biology, v. 8(4), pp. 331-333 (2012).

Zhou, Y.G., et al., "Highly Effective Chiral Ortho-Substituted BINAPO Ligands (o-BINAPO): Applications in Ru-Catalyzed Asymmetric Hydrogenations of β-Aryl-Substituted β-(Acylamino)acrylates and β-Keto Esters," Am. Chem. Soc., vol. 124, pp. 4952-4953 (2002).

Zhu, D., et al., "A recombinant ketoreductase tool-box. Assessing the substrate selectivity and stereoselectivity toward the reduction of β-ketoesters," Tetrahedron, vol. 62, pp. 901-905 (2006).

Zhu, D., et al., "Stereoselective Enzymatic Synthesis of Chiral Alcohols with the Use of a Carbonyl Reductase from *Candida magnoliae* with Anti-Prelog Enantioselectivity," Org. Chem., vol. 71, pp. 4202-4205 (2006).

\* cited by examiner

SYNTHETIC METHODS AND COMPOUNDS RELATED THERETO

BACKGROUND

Ceramide (Cer) is involved in regulation of anti-proliferative and apoptotic responses in various cancer cells (Hannun and Obeid, *Journal of Biological Chemistry* 2002, 277, 25847; Ogretmen and Hannun, *Nature Reviews Cancer* 2004, 4, 604). In the sphingolipid metabolism cascade, Cer can be formed from the hydrolysis of sphingomyelin (SM), catalyzed by acid and neutral sphingomyelinase (SMase), or synthesized de novo from serine and palmitoyl-CoA (Perry et al., *Journal of Biological Chemistry* 2000, 275, 9078). Reciprocally, Cer levels can be decreased by conversion into other interconnected bioactive sphingolipid species, which in turn reduces the apoptotic effectiveness of Cer. Cer can be broken down by one of many ceramidases (CDase), leading to the formation of sphingosine (SP). SP is then either acylated back to Cer via Ceramide synthase (CS) or phosphorylated to S1P by sphingosine kinase (SK), of which there are two isoforms, SK1 and SK2 (Hannun and Obeid, *Nat Rev Mol Cell Biol* 2008, 9, 139). According to the Cer-SP-S1P rheostat model, both Cer and sphingosine are apoptosis-induced lipids, whereas S1P leads to cell proliferation and inflammation and is referred to as a tumor-promoting lipid (Pyne and Pyne, *Nat Rev Cancer* 2010, 10, 489; Spiegel and Milstien, *Nat Rev Mol Cell Bio* 2003, 4, 397; Milstien and Spiegel, *Cancer Cell* 2006, 9, 148; Wymann and Schneiter, *Nat Rev Mol Cell Biol* 2008, 9, 162). Cer can also be phosphorylated into ceramide 1-phospate (Cer1P) by ceramide kinase (CK), antagonizing the pro-apoptotic action of ceramide and promoting inflammation (Wymann and Schneiter, *Nat Rev Mol Cell Biol* 2008, 9, 162), or glycosylated to glucosylceramide (GluCer) mediated by glucosylceramide synthase (GCS). The latter results in the development of multidrug resistance in many cancer cells (Ogretmen and Hannun, *Nature Reviews Cancer* 2004, 4, 604; Reynolds et al., *Cancer Letters* 2004, 206, 169).

Different strategies have been developed to enhance the level of Cer. For example, many anticancer drugs and stress-induced agonists have been used to increase endogenous Cer levels through de novo synthesis of Cer or the hydrolysis of SM. In addition, treating cancer cells in vitro with more easily dispersed short-chain Cers (C2 to C8-Cer) almost always produces apoptosis and cell-cycle arrest, and those exogenous Cers compete metabolically with natural Cers and their metabolites (Radin, *Biochem J* 2003, 371, 243). Currently, a number of anticancer agents in clinical trials act to increase Cer levels via inhibition of the conversion of GluCer and Cer1P from Cer, or by blocking the hydrolysis of Cer to S1P (Radin, *Biochem J* 2003, 371, 243). Sphingosine analogs that serve as pharmacological inhibitors of SK have been developed, including DMS (N,N-dimethylsphingosine) (Edsall et al., *Biochemistry-Us* 1998, 37, 12892; Yatomi et al., *Biochem-istry-Us* 1996, 35, 626) and sphingamine (D, L-threo-dihydrosphingosine) (Ahn et al., *Experimental Biology and Medicine* 2006, 231, 1664; Ahn and Schroeder, *Anticancer Res* 2010, 30, 2881). FTY720 (fingolimod) has also been known to directly inhibit SK1 activity, reduce tumor metastasis and increase apoptosis (Lim et al., *Journal of Biological Chemistry* 2011, 286, 18633). In addition, aromatic sphingosine analogs have been assessed as stronger sphingosine kinase inhibitors (Murakami et al., *Bioorg Med Chem Lett* 2005, 15, 1115; Moreno et al., *Organic Letters* 2011, 13, 5184; Lim et al., *Bioorg Med Chem Lett* 2004, 14, 2499). For example, water soluble sphingosine analog BML-258 (FIG. 1) is an SK1 selective inhibitor and is efficacious both in vitro and in vivo (Paugh et al., *Blood* 2008, 112, 1382; Pyne et al., *Cancer research* 2011, 71, 6576).

Accordingly, disclosed herein are synthetic methods and compounds related to the synthesis of bioactive compounds. The synthetic methods and compounds provide useful routes and efficient synthesis of the enantiomers of sphingosine derivatives with high diastereomeric excess.

SUMMARY OF THE INVENTION

In accordance with the purpose(s) of the invention, as embodied and broadly described herein, the invention, in one aspect, relates to synthetic method and compounds related thereto, for the production of compounds useful as or in the production of biologically active compounds.

Disclosed herein is a synthetic method comprising:
a) providing a first compound having the structure:

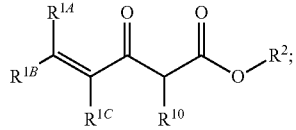

b) reacting the first compound in the presence of a ketoreductase, thereby forming a second compound having the structure:

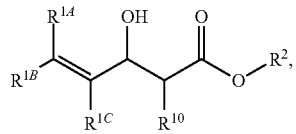

wherein each of $R^{1A}$, $R^{1B}$, and $R^{1C}$ is independently selected from hydrogen, aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, nitro, cyano, —C(O)O—$R^7$, —C(O)—$R^7$, ⁻COR$^7$, and —OR$^7$, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, ⁻COR$^7$, and —OR$^7$, wherein at least one of $R^{1A}$ and $R^{1B}$ is not hydrogen, wherein $R^2$ is selected from alkyl, alkenyl, alkynyl, haloalkyl, haloalkenyl, haloalkynyl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, $^-COR^7$, and —$OR^7$, wherein each $R^7$ is independently selected from hydrogen, alkyl, haloalkyl, polyhaloalkyl, alkylamino, dialkylamino, -alkyl-aryl, and -alkyl-heterocyclyl, wherein R is selected from hydrogen, alkyl, alkenyl, or alkynyl, and wherein the ketoreductase is selected from 101, 119, 130, NADH-101, NADH-110, P1-B02, P1-B05, P1-B10, P1-B12, P1-C01, P1-H08, P2-B02, P2-C11, P2-D03, P2-D11, P2-D12, P2-G03, P3-G09, and P3-H12.

Also disclosed herein is a synthetic method comprising aminating a second compound having the structure:

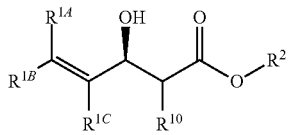

to form a third compound having the structure:

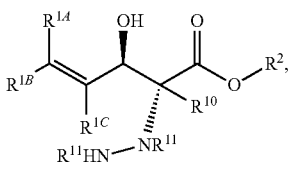

wherein each of $R^{1A}$, $R^{1B}$, and $R^{1C}$ is independently selected from hydrogen, aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, nitro, cyano, —C(O)O—$R^7$, —C(O)—$R^7$, $^-COR^7$, and —$OR^7$, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, $^-COR^7$, and —$OR^7$, wherein $R^2$ is selected from alkyl, alkenyl, alkynyl, haloalkyl, haloalkenyl, haloalkynyl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, $^-COR^7$, and —$OR^7$, wherein each $R^7$ is independently selected from hydrogen, alkyl, haloalkyl, polyhaloalkyl, alkylamino, dialkylamino, -alkyl-aryl, and -alkyl-heterocyclyl, wherein $R^{10}$ is selected from hydrogen, alkyl, alkenyl, or alkynyl, and wherein each $R^{11}$ is an amine protecting group.

Also disclosed herein, is a synthetic method comprising:

a) providing a first compound having the structure:

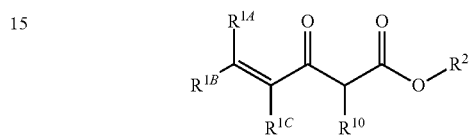

wherein each of $R^{1A}$, $R^{1B}$, and $R^{1C}$ is independently selected from hydrogen, aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, nitro, cyano, —C(O)O—$R^7$, —C(O)—$R^7$, $^-COR^7$, and —$OR^7$, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, $^-COR^7$, and —$OR^7$, wherein $R^2$ is selected from alkyl, alkenyl, alkynyl, haloalkyl, haloalkenyl, haloalkynyl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, $^-COR^7$, and —$OR^7$, wherein each $R^7$ is independently selected from hydrogen, alkyl, haloalkyl, polyhaloalkyl, alkylamino, dialkylamino, -alkyl-aryl, and -alkyl-heterocyclyl, wherein $R^{10}$ is selected from hydrogen, alkyl, alkenyl, or alkynyl;

b) reacting the first compound in the presence of a ketoreductase, thereby forming a second compound having the structure:

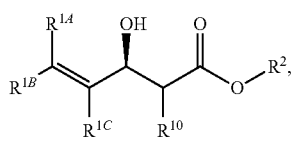

wherein the ketoreductase is 130, NADH-101, P3-G09, or P3-H12;

c) aminating the second compound to form a third compound having the structure:

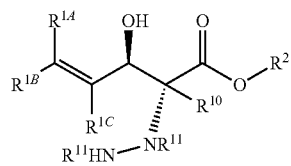

wherein $R^{11}$ is an amine protecting group, d) reducing the ester in the third compound to form an alcohol in a fourth compound;

e) protecting the alcohols in the fourth compound to form a fifth compound; and f) cleaving the N—N bond in the fifth compound to form a sixth having the structure:

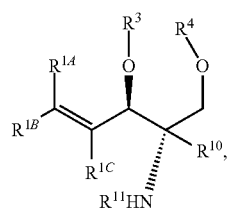

or

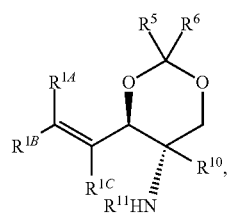

wherein $R^3$ and $R^4$ are alcohol protecting groups, or wherein $R^3$ and $R^4$ are linked together to form an alcohol protecting group, and wherein each of $R^5$ and $R^6$ is independently selected from hydrogen, alkyl, and aryl, or wherein $R^5$ and $R^5$ are linked together to form a cycloalkyl, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, ⁻$COR^7$, and —O$R^7$.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying Figures, which are incorporated in and constitute a part of this specification, illustrate several aspects and together with the description serve to explain the principles of the invention.

Figure 1:
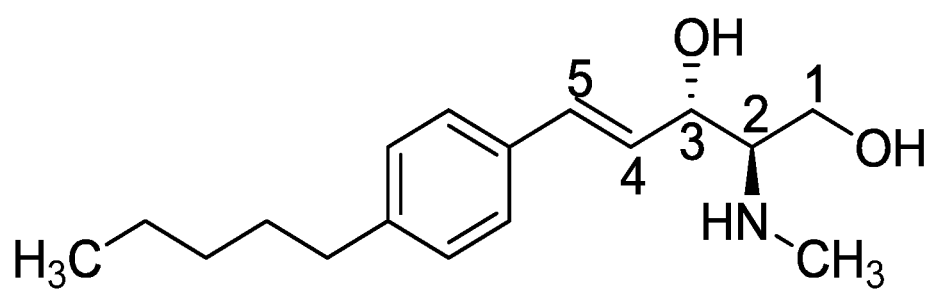
FIG. 1 shows the structure of BLM-258, (2R, 3S, 4E)-N-methyl-5-(4'-pentylphenyl-2-aminopent-4-ene-1,3-diol), a water soluble sphingosine analog. Low stereospecificity was observed with respect to the C-2 and C-3 stereocenters, resulting in a mixture of threo and erythro products necessitating chiral separation.
Figure 2:
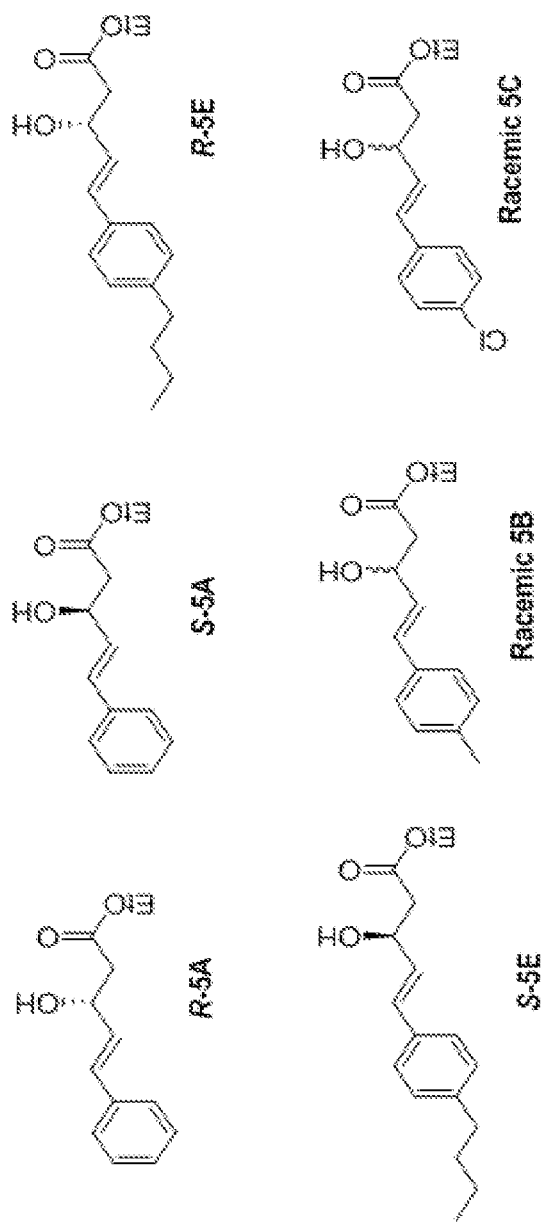
FIG. 2 shows the structures of trans-γ,δ-unsaturated β-hydroxyester analogs. Enantiopure (>99%) R-5A, R-5E and S-1E were prepared via reduction of the corresponding trans-γ,δ-unsaturated β-ketoesters using KREDs (Dai et al., *Molecular Catalysis B: Enzymatic*, In press). S-1A (75% e.e.) was prepared according to the literature (Carreira et al., *Journal of the American Chemical Society* 1994, 116, 8837). Racemic-5C and 5D were prepared via reduction of the corresponding trans-γ,δ-unsaturated β-ketoesters using NaBH$_4$.
Figure 3:
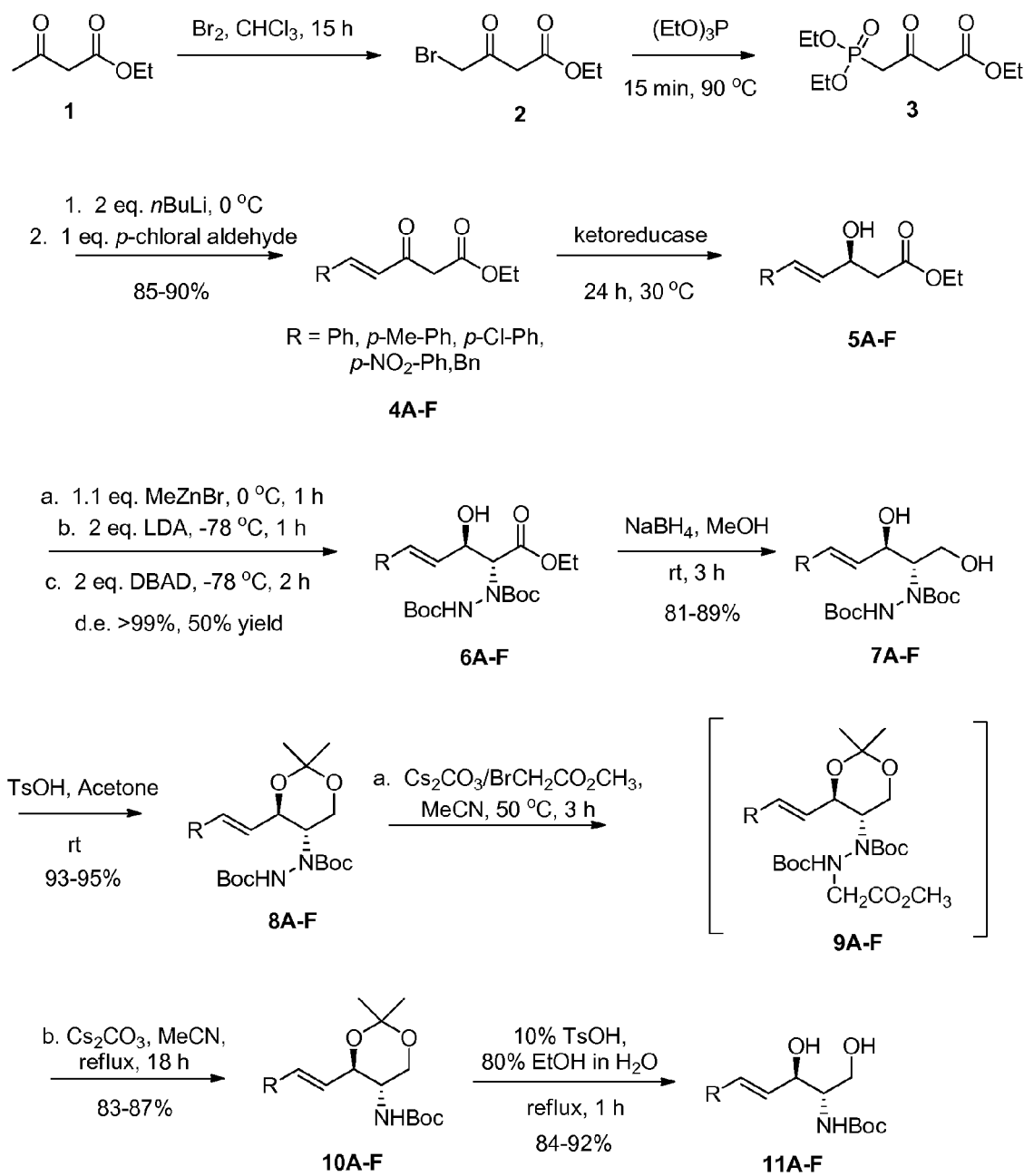
FIG. 3 shows the diastereoselective synthetic route utilized towards the preparation of D-erythro-sphingosine analogs.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. DEFINITIONS

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C—F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "analog" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein "protecting group" refers functional group that masks the characteristic reactivity of another group to which it can later be converted. Thus, an alcohol protecting group is a functional group that masks the characteristic reactivity of the alcohol, and the functional group can be removed to yield the alcohol. Alcohol protecting groups can include, but are not limited to, acetyl, benzoyl, benzyl, βmethoxyethoxymethyl ether (MEM), methoxymethyl ether (MOM), methyl ethers, tetrahydrofuran (THF), tetrahydropyranyl (THP), tosyl, methylthiomethyl ether, and p-methoxybenzyl ether. Similarly, an amine protecting group is a functional group that masks the characteristic reactivity of the amine (primary or secondary amine), and the functional group can be removed to yield the amine. Amine protecting groups can include, but are not limited to, N-tert-butoxycarbonyl (t-Boc or Boc), —COOEt, —COOBn. The use of protecting groups, both alcohol protecting groups and amine protecting groups is common practice by those skilled in the art.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. Non-limiting examples of alkyls include C1-18 alkyl, C1-C12 alkyl, C1-C8 alkyl, C1-C6 alkyl, C1-C3 alkyl, and C1 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

The term "alkenyl" as used herein is a hydrocarbon group of 2 to 24 carbon atoms with a structural formula containing at least one carbon-carbon double bond. The alkenyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein. Non-limiting examples of alkenyls include C2-18 alkenyl, C2-12 alkenyl, C2-8 alkenyl, C2-6 alkenyl, and C2-3 alkenyl.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein. Non-limiting examples of alkynyls include C2-18 alkynyl, C2-12 alkynyl, C2-8 alkynyl, C2-6 alkynyl, and C2-3 alkynyl.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "ester" as used herein is represented by the formula —$OC(O)A^1$ or —$C(O)OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1O(O)C$-$A^2$-$C(O)O)_a$— or -($A^1O(O)C$-$A^2$-$OC(O))_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1O$-$A^2O)_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "azide" as used herein is represented by the formula —$N_3$.

The term "thiol" as used herein is represented by the formula —SH.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999). In one aspect, a hydrolysable group is a protecting group.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. SYNTHESIS OF Γ,Δ-UNSATURATED-B-HYDROXYESTERS AND D-ERYTHRO-SPHINGOSINE ANALOGS

Due to the important bioactivities of sphingosine and sphingosine analogs, many synthetic approaches have been developed to towards these target molecules (Kumar et al., *Organic & Biomolecular Chemistry* 2010, 8, 5074; Kobayashi et al., *Tetrahedron Letters* 1994, 35, 9573; van den Berg et al., *Tetrahedron Letters* 2002, 43, 8409; Cai et al., *Organic & Biomolecular Chemistry* 2006, 4, 1140; Llaveria et al., *Organic Letters* 2008, 11, 205; van den Berg, R. J. B. H. N.; van den Elst et al., *European Journal of Organic Chemistry* 2011, 2011, 6685; Yang and Liebeskind, *Organic Letters* 2007, 9, 2993). Most syntheses begin with a protected serine aldehyde (Murakami et al., *Bioorg Med Chem Lett* 2005, 15, 1115; Lim et al., *Bioorg Med Chem Lett* 2004, 14, 2499; Chandrasekhar et al., *Tetrahedron: Asymmetry* 2006, 17, 1380; Herold, *Helv Chim Acta* 1988, 71, 354; Van Overmeire et al., *J Med Chem* 1999, 42, 2697; Wong et al., *J Med Chem* 2009, 52, 3618; Zipkin et al., US 2010/0035959 A1, 2010; Radunz et al., *Liebigs Annalen der Chemie* 1988, 1988, 1103; Nimkar et al., *Tetrahedron Letters* 1988, 29, 3037; Garner et al., *The Journal of Organic Chemistry* 1988, 53, 4395; Dondoni et al., *Journal of the Chemical Society, Chemical Communications* 1988, 10) or its corresponding derivative (Moreno et al., *Organic Letters* 2011, 13, 5184). A patent of the synthesis of aromatic sphingosine analog BLM-258 by Zipkin et al. uses a protected serine aldehyde (Zipkin et al., US 2010/0035959 A1, 2010). In synthesis utilizing a protected serine aldehyde, the central problem is the low stereospecificity observed with respect to the C-2 and C-3 stereocenters, resulting in a mixture of threo and erythro products that require chiral separation (Zipkin et al., US 2010/0035959 A1, 2010).

Therefore, enantiomerically pure γ,δ-unsaturated-β-hydroxyesters and their derivatives are important chiral building blocks for synthesis of many biologically active compounds, pharmaceutical products and their intermediates, such as (−)-CP$_2$-Disorazole C$_1$ (C. D. Hopkins, et al., *Org. Lett.* 13 (2011) 4088-4091), turnagainolides A and B (D. Li, et al., *J. Nat. Prod.* 74 (2011) 1093-1099), epothilone (E. A. Reiff, et al., *Tetrahedron Lett.* 45 (2004) 5845-5847) and Seimatopolide A (B. Schmidt, et al., *J. Org. Chem.* 77 (2012) 10897-10906). Many traditional methods have been addressed and provide pathways to make β-hydroxyesters asymmetrically, for example, (1) enantioselective Mukaiyama aldol addition between aldehyde and methyl (ethyl)acetate O-Silyl enolates with a chiral Ti(IV) complexes as catalyst (E. M. Carreira, et al., *J. Am. Chem. Soc.* 116 (1994) 8837-8838; T. Mukaiyama, The Directed Aldol Reaction, in: Organic Reactions, John Wiley & Sons, Inc., 2004; M. Smrčina, et al., *Synlett*. (1991) 231-232), (2) enantioselective ruthenium-catalyzed hydrogenation of saturated α-ketoesters (I. Rimoldi, et al., *Tetrahedron: Asymmetry.* 22 (2011) 2110-2116), β-ketoesters (A. Hu, et al, *Angew. Chem., Int. Ed.* 43 (2004) 2501-2504; D. F. Taber, et al., *Tetrahedron Lett.* 32 (1991) 4227-4230; Y.-G. Zhou, et al., *Am. Chem. Soc.* 124 (2002) 4952-4953; Z. Zhang, et al, *J. Org. Chem.* 65 (2000) 6223-6226; M. J. Burk, et al., *J. Am. Chem. Soc.* 117 (1995) 4423-4424; C. Greck, et al. *Genet, Synlett*. (1993) 475-477; J. P. Genêt, et al., *Tetrahedron Lett.* 35 (1994) 4559-4562; B. Seashore-Ludlow, et al., *Org. Lett.* 14 (2012) 6334-6337; J. P. Genêt, et al., *Tetrahedron: Asymmetry.* 5 (1994) 665-674; A. Girard, et al., *Tetrahedron Lett.* 37 (1996) 7967-7970) and α,β-unsaturated carbonyls (T. Ohkuma, et al., *J. Am. Chem. Soc.* 120 (1998) 13529-13530; N. Arai, et al., *Angew. Chem., Int. Ed.* 47 (2008) 7457-7460, and (3) chiral oxazaborolidine-catalyzed reduction of prochiral ketones, cyclic and acyclic α, and β-enones (E. J. Corey, et al., *J. Am. Chem. Soc.* 109 (1987) 5551-5553; E. J. Corey, et al., *J. Am. Chem. Soc.* 109 (1987) 7925-7926; E. J. Corey, et al., *Angew. Chem., Int. Ed.* 37 (1998) 1986-2012; Y. Kawanami, et al., *Tetrahedron,* 59 (2003) 8411-8414; D. J. Mathre, et al., *J. Org. Chem.* 58 (1993) 2880-2888).

All of these methods, while potentially providing high enantioselectivity, have disadvantages. The Mukaiyama aldol methods often require an expensive chiral ligand (e.g. BINAP) and multiple steps to make the catalyst (M. Smrčina, et al., *Synlett*. (1991) 231-232). While ruthenium-catalyzed hydrogenation has been shown to selectively reduce the carbonyl of β-ketoesters chemoselectively in the presence of a nonconjugated carbon-carbon double bond (D. F. Taber, et al., *Tetrahedron Lett.* 32 (1991) 4227-4230; C. Greck, et al., *Tetrahedron Lett.* 37 (1996) 2031-2034), it was previously found (X. Ma, et al., *Chem. Commun.* 48 (2012) 5352-5354) that partial hydrogenation of the double bond of conjugated γ,δ-unsaturated-β-ketoesters often occurs, and is difficult to control. Recently, Ma et al. published a Ru-catalyzed hydrogenation of γ-halo-γ,δ-unsaturated-β-ketoesters in up to 97% ee (X. Ma, et al., *Chem. Commun.* 48 (2012) 5352-5354), where halogen at the γ-position is needed to protect the γ,δ-carbon-carbon double bond with further organometallic transformation required to remove the vinyl halide moiety. The enantioselectivity of chiral oxazaborolidines catalysts (3) are sensitive to moisture and temperature and must be conducted under strictly anhydrous conditions and typically at low temperature (−20° C. and below). Also, the use of BH$_3$.THF (or BH$_3$.Me$_2$S) is often incompatible with carbon-carbon double bonds. Although these chemical methods using chiral auxiliaries are frequently used, other limitations remain in many cases; the incompatibility of catalytic conditions with a number of functionalities (J. P. Genêt, et al., *Tetrahedron: Asymmetry.* 5 (1994) 675-690; B. Schmidt, *J. Org. Chem.* 69 (2004) 7672-7687; S. Akutagawa, *Appl. Catal., A* 128 (1995) 171-207) and the catalytic behavior (enantiomeric purity and productivity) being sensitive to even slight modifications in the substances due to the change of steric and electronic properties.

With the advantages of high enantioselectivity, broader substrate acceptance, mild and environmental friendly reaction conditions, tolerance of organic solvents and easy separation, biocatalysts using whole cells and isolated enzymes have received increasing interest toward the production of optically pure β-hydroxyesters and their derivatives (T. Matsuda, R. et al., *Tetrahedron: Asymmetry.* 20 (2009) 513-557; N. J. Turner, *Nat. Chem. Biol.* 5 (2009) 568-574; D. Zhu, et al., *Org. Chem.* 71 (2006) 4202-4205; I. A. Kaluzna, et al., *J. Am. Chem. Soc.* 126 (2004) 12827-12832; G. W. Huisman, et al., *Curr. Opin. Chem. Biol.* 14 (2010) 122-129; D. Kalaitzakis, et al., *Tetrahedron: Asymmetry.* 18 (2007) 2418-2426). For instances, the asymmetric reduction of α- and/or β-ketoesters was evaluated by means of whole cells of *Candida parapsilosis* ATCC 7330 (on the reduction alkyl 2-oxo-4-arylbutanoates) (B. Baskar, et al., *Tetrahedron: Asymmetry.* 15 (2004) 3961-3966), the recombinant *Escherichia Coli* (for the synthesis of 3-hydroxybutyrate) (K. Schroer, et al., *Biotechnol.* 132 (2007) 438-444), *Chlorella* strains (toward the reduction of α-ketoesters) (K. Ishihara, et al., *Biosci., Biotechnol., Biochem.* 64 (2000) 2099-2103), yeast (reduction of α- and β-ketoesters) (I. A. Kaluzna, et al, *J. Am. Chem. Soc.* 126 (2004) 12827-12832; I. Rimoldi, et al., *Tetrahedron: Asymmetry.* 22 (2011) 597-602), carbonyl reductase from *Candila magnolia* (D. Zhu, et al., *Org. Chem.* 71 (2006)

4202-4205), nicotinamide-dependent ketoreductases (reduction of β-ketoesters with alkyl substituents at α- or β-position) (S. Kambourakis, et al., *Tetrahedron*. 60 (2004) 663-669; D. Zhu, et al., *Tetrahedron*. 62 (2006) 901-905), and NADPH-dependent ketoreductases (toward the reduction of α-alkyl-β-ketoesters) (D. Kalaitzakis, et al., *Org. Lett*. 7 (2005) 4799-4801). What is more, *Candida parapsilosis* ATCC 7330-induced deracemisation of unsaturated aryl β-hydroxyesters to a single enantiomer has also been reported (S. K. Padhi, et al., *Tetrahedron: Asymmetry*. 16 (2005) 2790-2798; T. Saravanan, et al., *Tetrahedron: Asymmetry*. 23 (2012) 1360-1368).

1. Synthesis of γ,δ-Unsaturated-B-Hydroxyesters

In one aspect, γ,δ-unsaturated-β-hydroxyesters of the present invention can be prepared generically by the synthesis scheme as shown below. All positions are defined herein.

SCHEME 1A

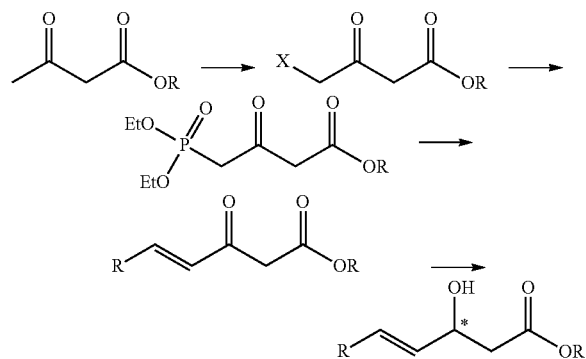

Compounds are represented in generic form, with substituents as noted in compound descriptions elsewhere herein. A more specific example is set forth below.

SCHEME 1B

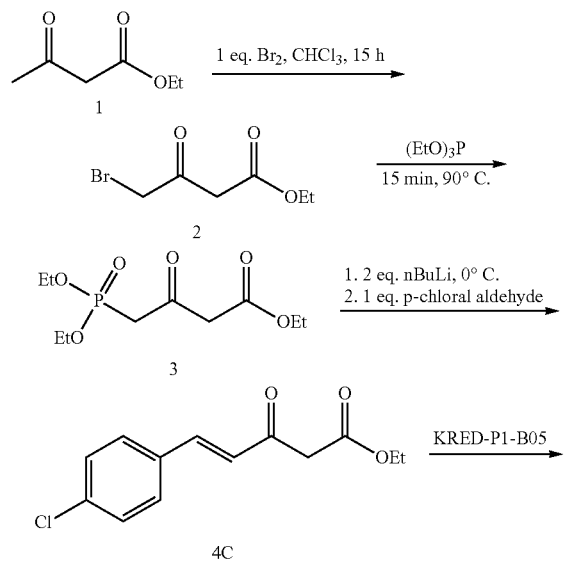

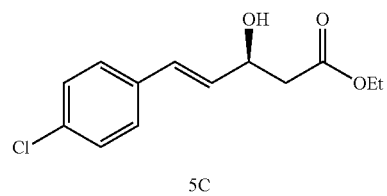

5C

In one aspect, compounds of type 5C, and similar compounds, can be prepared according to reaction Scheme 1B above. Thus, compounds of type 2 can be prepared by bromination of a ketone, e.g. ethyl 3-oxobutanoate (1) as shown above, which is commercially available or can be prepared by methods known to one skilled in the art. The reaction can be carried out using an appropriate halide, e.g. bromine, in an appropriate solvent, e.g. chloroform, for a suitable period of time, e.g. 15 h. A compound of type 3 can be prepared by substitution of a compound of type 2. For example, as shown above, such a substitution reaction can be accomplished using a suitable phosphite, e.g., triethyl phosphite, at a suitable temperature, e.g. 90° C., for a suitable period of time, e.g. 15 min. A compound of type 4C can be prepared by displacement reaction of a compound of type 3. For example, as shown above, such a displacement reaction can be accomplished in the presence of a suitable base, e.g. butyl lithium, at a suitable temperature, e.g. 0° C., followed by addition of a suitable aldehyde, e.g. p-chloral aldehyde. Suitable aldehydes that can be used in the reaction are commercially available or can be prepared by methods known to one skilled in the art. A compound of type 5C can be prepared by reduction of a compound of type 4C. For example, as shown above, such a reduction reaction can be accomplished using a suitable ketoreductase, e.g. KRED-P1-B05. Suitable ketoreductases that can be used in the reaction are commercially available or can be isolated by methods known to one skilled in the art. As can be appreciated by one skilled in the art, the above reaction provides an example of a generalized approach wherein compounds similar in structure to the specific reactants above (compounds similar to compounds of type 2, 3 and 4C), can be substituted in the reaction to provide γ,δ-unsaturated-β-hydroxyesters similar to Formula 4C.

2. Synthesis of D-Erythro-Sphingosine Analogs

In one aspect, D-erythro-sphingosine analogs of the present invention can be prepared generically by the synthesis scheme as shown below. All positions are defined herein.

SCHEME 2A

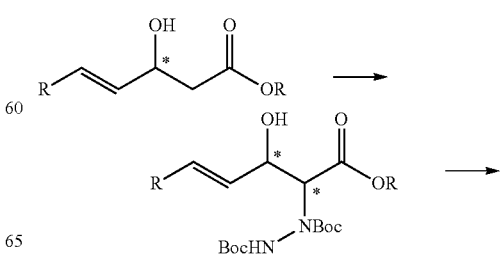

17
-continued

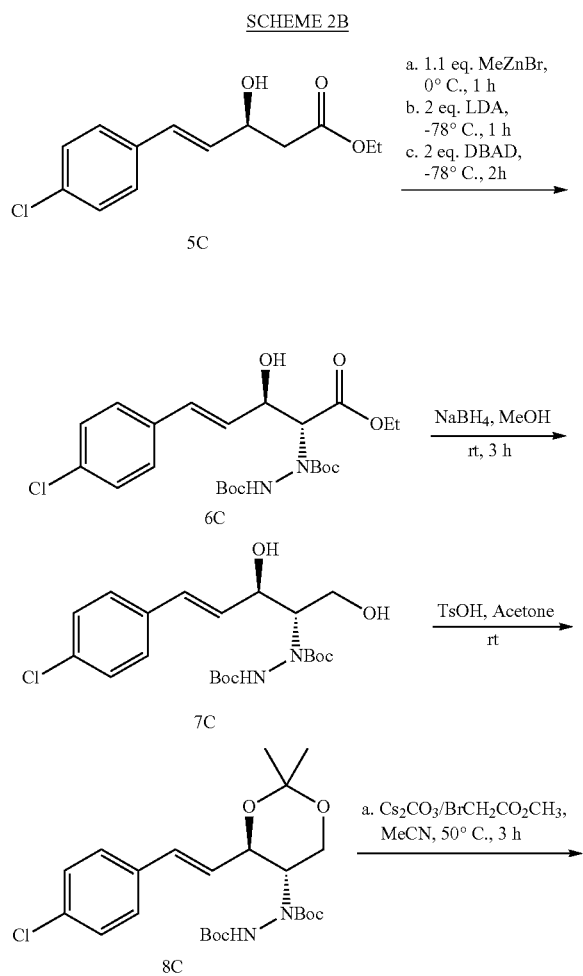

Compounds are represented in generic form, with substituents as noted in compound descriptions elsewhere herein. A more specific example is set forth below.

18
-continued

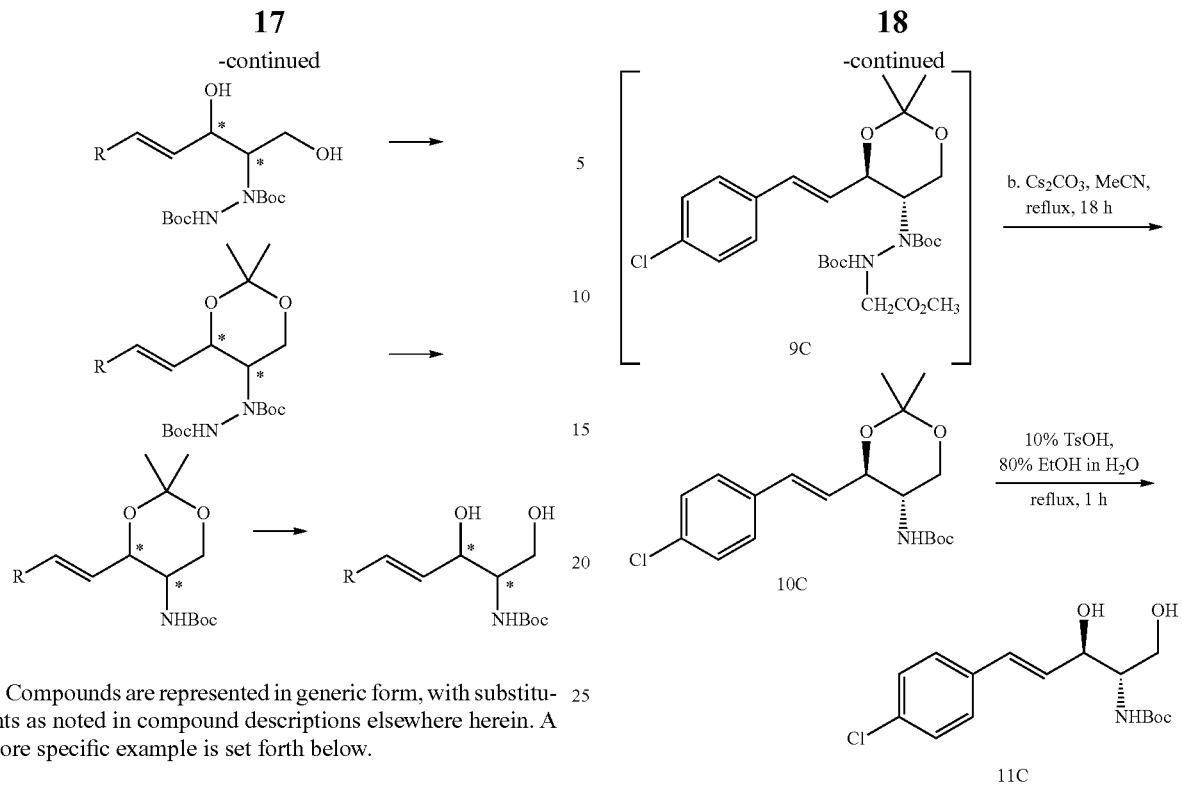

In one aspect, compounds of type 11C, and similar compounds, can be prepared according to reaction Scheme 2B above. Thus, compounds of type 6C can be prepared by substitution of an ester, e.g. (S,E)-ethyl 5-(4-chlorophenyl)-3-hydroxypent-4-enoate (5C) as shown above, which is commercially available or can be prepared by methods known to one skilled in the art. The reaction can be carried out using an appropriate salt, e.g. methyl zinc(II)bromide, at an appropriate temperature, e.g. 0° C., for a suitable period of time, e.g. 1 h; followed by addition of an appropriate base, e.g. lithium diisopropylamino, at a suitable temperature, e.g. −78° C., for a suitable period of time, e.g. 1 h. An appropriate activating agent is added, e.g. dibenzy azodicarboxylate, as shown above, at a suitable temperature, e.g. −78° C., stirred for an appropriate period of time, e.g. 1 h. A compound of type 7C can be prepared by reduction of a compound of type 6C. For example, as shown above, such a reduction can be accomplished using a suitable reducing agent, e.g. sodium borohydride, in a suitable protic solvent, e.g. methanol, at a suitable temperature, e.g. rt, for a suitable period of time, e.g. 3 h. A compound of type 8C can be prepared by protection of a compound of type 7C. For example, as shown above, such a protection can be accomplished using a suitable protecting agent, e.g. p-toluene sulfonic acid monohydrate, in a suitable solvent, e.g. acetone, at a suitable temperature, e.g. rt. A compound of type 10C can be prepared by eliminative cleavage of a compound of type 8C. For example, as shown above, such an eliminative cleavage can be accomplished using a suitable base, e.g. cesium carbonate, in an appropriate solvent, e.g. acetonitrile, in the presence of a suitable haloacetate, e.g. methyl bromoacetetate, at a suitable temperature, e.g. 50° C., for a suitable period of time, e.g. 3 h to afford intermediate 9C. Suitable haloacetates are commercially available or can be prepared by methods known to one skilled in the art. Subsequent addition of a suitable base, e.g. cesium carbonate, in a suitable solvent, e.g. acetonitrile, at a suitable temperature, e.g. reflux, for a suitable period of time, affords a compound of type 10C. A compound of type 11C can be prepared by deprotection of a compound of type 10C. For example, as shown above, such a deprotection can be accomplished using a suitable acid, e.g. p-toluene sulfonic acid, in a suitable solvent, e.g. 80% ethanol in water, at a suitable temperature, e.g. reflux, for a suitable period of time, e.g. 1 h. As can be appreciated by one skilled in the art, the above reaction provides an example of a generalized approach wherein compounds similar in structure to the specific reactants above (compounds similar to compounds of type 6C, 7C, 8C, 9C and 10C), can be substituted in the reaction to provide D-erythro-sphingosine analogs similar to Formula 11C.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

Disclosed herein are compounds and methods related to the synthesis of γ,δ-unsaturated-β-hydroxyesters and D-erythro-sphingosine analogs. The disclosed compounds can be synthesized with high enantioselectivity, such as above 90% ee, for example greater than 99% ee. The conversion and purification of these compounds can be achieved economically, safely and readily by the methods disclosed herein. Compound

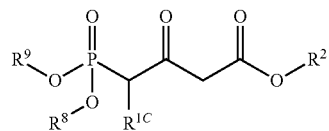

can be made and used as shown in Schemes 2C-2G.

Scheme 2C

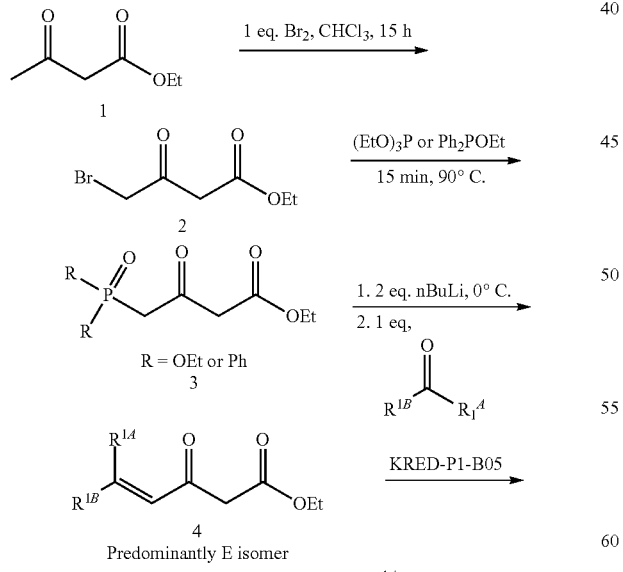

Scheme 2D

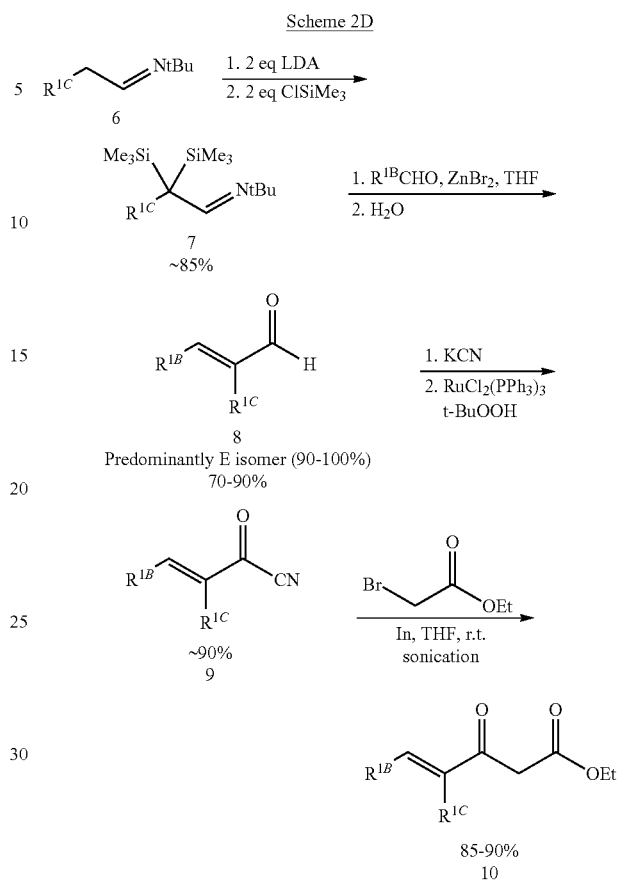

Scheme 2E

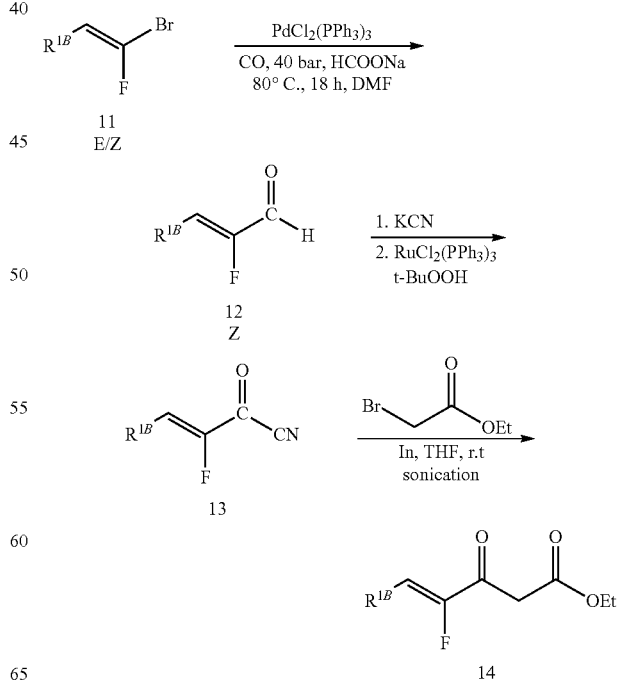

Scheme 2F

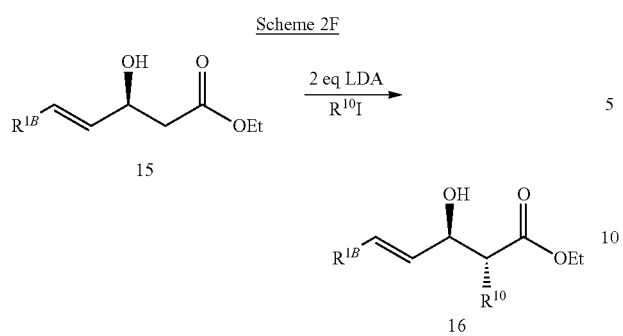

Scheme 2G

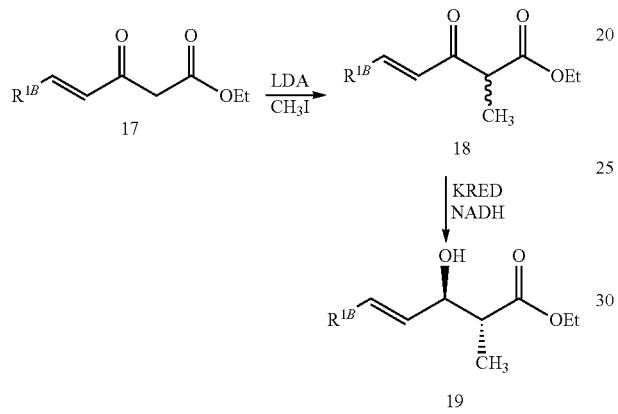

The compounds shown in Schemes 2C-2G can be made by the methods described in the references cited below, all of which are incorporated by references herein.

Compound 3 can be made by the methods disclosed by Moorhoff, C. M. Synthetic Communications 2003, 33, 2069-2086.

Compound 4 can be made by the methods disclosed by van den Goorbergh, J. A. M.; van der Gen, A. Tetrahedron Letters 1980, 21, 3621-3624; du Pisani, C.; et al. Synthetic Communications 2002, 32, 305-314; Boldalski, R.; et al. Tetrahedron Letters 1980, 21, 2237-2290.

Compound 8 can be made by the methods disclosed by Lahmar, N.; Aatar, J.; Taicir, B. A.; Amri, H.; Bellassoued, M. Journal of Organometallic Chemistry 2006, 691, 3018-3026.

Compound 9 can be made by the methods disclosed by Murahashi, S-I.; Naota, T.; Nakajima, N. Journal of Organic Chemistry 1986, 51, 898-901.

Compound 10 can be made by the methods disclosed by Park, Y. S.; Han, J. H.; Yoo, B.; Choi, K. I.; Kim, J. H.; Yoon, C. M.; Yoo, B. W. Bulletin Korean Chemical Society 2005, 26, 878-879.

Compound 12 can be made by the methods disclosed by Zemmouri, R.; Kajjout, M.; Castanet, Y.; Eddarir, S.; Roland, C. Journal of Organic Chemistry 2011, 76, 7691-7698.

Compound 13 can be made by the methods disclosed by Lahmar, N.; Aatar, J.; Taicir, B. A.; Amri, H.; Bellassoued, M. Journal of Organometallic Chemistry 2006, 691, 3018-3026.

Compound 14 can be made by the methods disclosed by Park, Y. S.; Han, J. H.; Yoo, B.; Choi, K. I.; Kim, J. H.; Yoon, C. M.; Yoo, B. W. Bulletin Korean Chemical Society 2005, 26, 878-879.

Compounds 16 and 18 can be made by the methods disclosed by Frater, G.; Muller, U.; Gunther, W. Tetrahedron 1984, 40, 1269-1277.

Compound 19, for reduction of ketoesters, can be made by the methods disclosed by Kalaitzakis, D.; Rozzell, J. D.; Kambourakis, S.; Smonou, I. Organic Letters 2005, 7, 4799-4801.

C. COMPOUNDS

Disclosed herein are biologically active compounds and compounds useful in the preparation or synthesis of biologically active compounds.

Disclosed herein is a first compound having the structure:

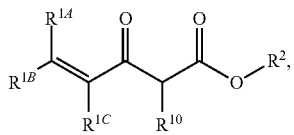

wherein each of $R^{1A}$, $R^{1B}$, and $R^{1C}$ is independently selected from hydrogen, aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, nitro, cyano, —C(O)O—$R^7$, —C(O)—$R^7$, ⁻COR$^7$, and —OR$^7$, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, ⁻COR$^7$, and —OR$^7$, wherein at least one of $R^{1A}$ and $R^{1B}$ is not hydrogen, wherein $R^2$ is selected from alkyl, alkenyl, alkynyl, haloalkyl, haloalkenyl, haloalkynyl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, ⁻COR$^7$, and —OR$^7$, wherein each $R^7$ is independently selected from hydrogen, alkyl, haloalkyl, polyhaloalkyl, alkylamino, dialkylamino, -alkyl-aryl, and -alkyl-heterocyclyl, wherein $R^{10}$ is selected from hydrogen, alkyl, alkenyl, and alkynyl.

In one aspect, the first compound can formed from a compound having the structure:

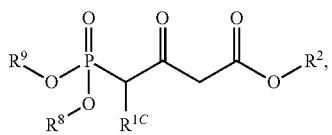

wherein $R^8$ and $R^9$ is independently selected from alkyl, alkenyl, alkynyl, aryl, and phenyl.

Also disclosed herein is a second compound having the structure:

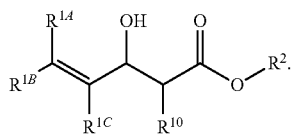

In one aspect, the second compound can have the structure:

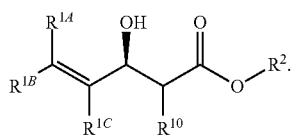

In another aspect, the second compound can have the structure:

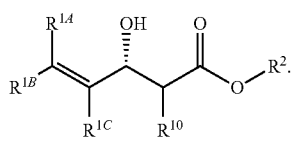

Also disclosed herein is a third compound having the structure:

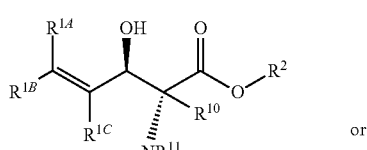

or

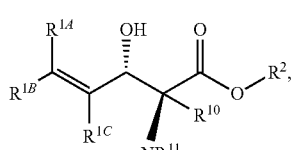

wherein each $R^{11}$ is independently an amine protecting group.

In one aspect, third compound has the structure:

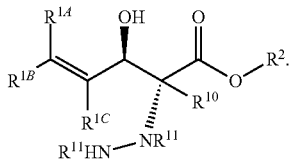

Also disclosed herein is a fourth compound, which is a compound that has been formed from reducing the ester in the third compound to form an alcohol in the fourth compound. The fourth compound comprises at least two alcohol groups.

Also disclosed herein is a fifth compound, which is a compound wherein the alcohols in the fourth compound are protected. In one aspect, the fifth compound has the structure:

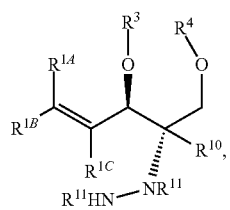

wherein each of $R^3$ and $R^4$ are alcohol protecting groups, or wherein $R^3$ and $R^4$ are linked together to form an alcohol protecting group.

In one aspect, the fifth compound has the structure:

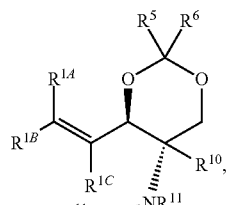

wherein each of $R^5$ and $R^6$ is independently selected from hydrogen, alkyl, and aryl, or wherein $R^5$ and $R^5$ are linked together to form a cycloalkyl, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, ⁻COR$^7$, and —OR$^7$.

Also disclosed herein is a sixth compound, which is the fifth compound wherein the N—N has been cleaved. In one aspect, the sixth compound has the structure:

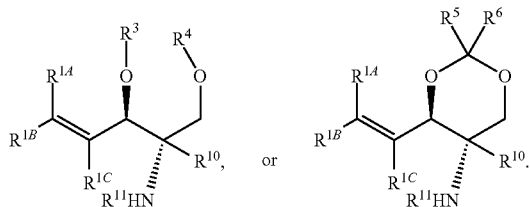

Also disclosed herein is a seventh compound having the structure:

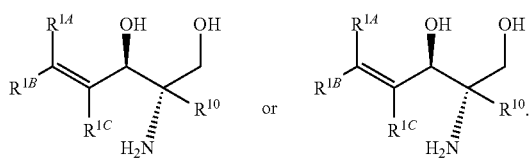

a. $R^1$ Groups

In one aspect, $R^{1A}$ is selected from hydrogen, aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, and haloalkynyl. For example, $R^{1A}$ can be hydrogen, alkyl, and -alkyl-aryl. In another example, $R^{1A}$ can be hydrogen. In yet another example, $R^{1A}$ can be alkyl or -alkyl-aryl.

In one aspect, $R^{1A}$ is substituted with 0 groups. In another aspect, $R^{1A}$ is substituted with 1 group. For example, $R^{1A}$ can be substituted with alkyl.

In one aspect, $R^{1B}$ is selected from hydrogen, aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, and haloalkynyl. For example, $R^{1B}$ can be selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, and alkynyl-heteroaryl. In another example, $R^{1B}$ can be aryl or -alkyl-aryl.

In one aspect, $R^{1B}$ is substituted with 0 groups. In another aspect, $R^{1B}$ is substituted with 1 group. In another aspect, $R^{1B}$ is substituted with 2 groups. For example, $R^{1B}$ can be substituted with 1 group selected from alkyl, alkenyl, alkynyl, haloalkyl, haloalkenyl, halo, haloalkynyl, and alkoxy. In another example, $R^{1B}$ can be substituted with 1 group selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, and alkynyl-heteroaryl.

In one aspect, $R^{1A}$ is small than $R^{1B}$. For example, $R^{1A}$ can be hydrogen or C1-C3 alkyl and $R^{1B}$ can be can be selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, and alkynyl-heteroaryl. In another example, $R^{1A}$ can be hydrogen and $R^{1B}$ can be can be selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, and alkynyl-heteroaryl.

In one aspect, $R^{1C}$ is hydrogen or alkyl. For example, $R^{1C}$ can be hydrogen. In another example, $R^{1C}$ can be C1-C3 alkyl, such as methyl.

In one aspect, $R^{1C}$ is substituted with 0 groups.

In one aspect, $R^{1A}$ and $R^{1C}$ are hydrogen. In another aspect, $R^{1A}$ is alkyl or alkyl-aryl and $R^{1C}$ is hydrogen. In yet another aspect, $R^{1A}$ is hydrogen and $R^{1C}$ is methyl.

In one aspect, $R^{1A}$, $R^{1C}$, and $R^{10}$ are hydrogen. In one aspect, $R^{1A}$, $R^{1C}$, and $R^{10}$ are hydrogen and $R^{1B}$ is selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, and alkynyl-heteroaryl. In one aspect, one of $R^{1A}$, $R^{1C}$, and $R^{10}$ is C1-C3 alkyl and the other two of $R^{1A}$, $R^{1C}$, and $R^{10}$ are hydrogen and $R^{1B}$ is selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, and alkynyl-heteroaryl.

In one aspect, $R^{1A}$ is hydrogen, $R^{1B}$ is C13-alkyl, and $R^{1C}$ is hydrogen.

b. $R^2$ Groups

In one aspect, $R^2$ is selected from alkyl, alkenyl, and alkynyl. For example, $R^2$ can be alkyl, such as methyl or ethyl.

In one aspect, $R^2$ is substituted with 0 groups.

c. $R^3$ and $R^4$ Groups

In one aspect, each of $R^3$ and $R^4$ is independently an alcohol protecting group. Alcohol protecting groups are known to one skilled in the art. For example, each of $R^3$ and $R^4$ is independently an alcohol protecting group selected from acetyl, benzoyl, benzyl, β-methoxyethoxymethyl ether (MEM), methoxymethyl ether (MOM), methyl ethers, tetrahydrofuran (THF), tetrahydropyranyl (THP), tosyl, methylthiomethyl ether, and p-methoxybenzyl ether.

In one aspect, $R^3$ and $R^4$ are linked together to form an alcohol protecting group. Alcohol protecting groups formed with two alcohols are known to those skilled in the art. For example, $R^3$ and $R^4$ are linked together to form a cyclic structure, such a monocyclic or bicyclic structure. Suitable structures for the third compound when $R^3$ and $R^4$ are linked together to form a cyclic structure include:

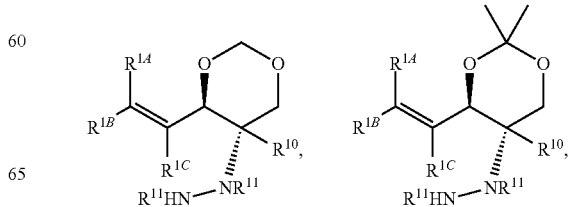

-continued

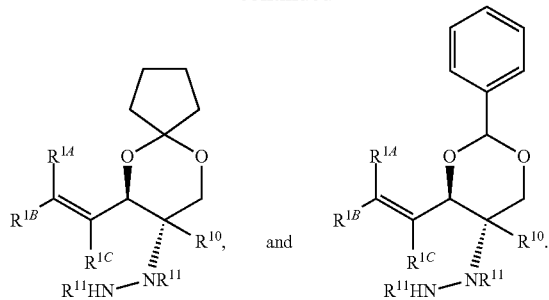

d. $R^5$ and $R^6$ Groups

In one aspect, each of $R^5$ and $R^6$ is independently selected from hydrogen, alkyl, and aryl. In one aspect, both $R^5$ and $R^6$ are selected from hydrogen, alkyl, and aryl. For example, both $R^5$ and $R^6$ can be hydrogen. In another example, both $R^5$ and $R^6$ can be alkyl. In another aspect, $R^5$ and $R^6$ are different. For example, $R^5$ can be hydrogen and $R^6$ can be aryl. Non-limiting compounds showing $R^5$ and $R^6$ include:

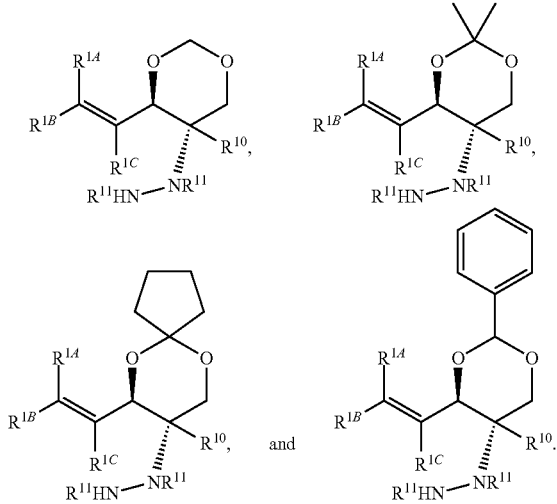

e. $R^7$ Groups

In one aspect, each $R^7$ is independently selected from hydrogen, alkyl, haloalkyl, polyhaloalkyl, alkylamino, dialkylamino, -alkyl-aryl, and -alkyl-heterocyclyl. For example, each $R^7$ can independently be hydrogen or alkyl. In another example, each $R^7$ can independently be hydrogen.

f. $R^8$ and $R^9$ Groups

In one aspect, both $R^8$ and $R^9$ are selected from alkyl, alkenyl, alkynyl, aryl, and phenyl. For example, both $R^8$ and $R^9$ can be alkyl, such as C1-C3 alkyl. In another example, both $R^8$ and $R^9$ can be alkenyl, such as C1-C3 alkenyl. In yet another example, both $R^8$ and $R^9$ can be aryl, such as phenyl.

g. $R^{10}$ Groups

In one aspect, $R^{10}$ is hydrogen or alkyl. For example, $R^{10}$ can be hydrogen. In another example, $R^{10}$ can be alkyl, such as C1-C3 alkyl, for example, methyl.

h. $R^{11}$ Groups

In one aspect, $R^{11}$ is an amine protecting group. Amine protecting groups are known to those skilled in the art. Non-limiting examples of amine protecting groups include N-tert-butoxycarbonyl (t-Boc or Boc), —COOEt, —COOBn. For example, the amine protecting group can be Boc.

D. SYNTHETIC METHODS

Disclosed herein are synthetic methods to make the compounds disclosed herein. The synthetic methods can produce the useful compounds at high yields and at desired stereo chemistry.

It is understood that the synthetic methods apply to the corresponding compounds disclosed herein.

Disclosed herein is a synthetic method comprising:

a) providing a first compound having the structure:

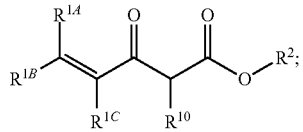

b) reacting the first compound in the presence of a ketoreductase, thereby forming a second compound having the structure:

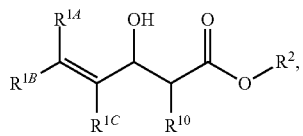

wherein each of $R^{1A}$, $R^{1B}$, and $R^{1C}$ is independently selected from hydrogen, aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, nitro, cyano, —C(O)O—$R^7$, —C(O)—$R^7$, ⁻COR$^7$, and —OR$^7$, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, ⁻COR$^7$, and —OR$^7$, wherein at least one of $R^{1A}$ and $R^{1B}$ is not hydrogen, wherein $R^2$ is selected from alkyl, alkenyl, alkynyl, haloalkyl, haloalkenyl, haloalkynyl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, ⁻COR$^7$, and —OR$^7$, wherein each $R^7$ is independently selected from hydrogen, alkyl, haloalkyl, polyhaloalkyl, alkylamino, dialkylamino, -alkyl-aryl, and -alkyl-heterocyclyl, wherein $R^{10}$ is selected from hydrogen, alkyl, alkenyl, or alkynyl, and wherein the ketoreductase is selected from 101, 119, 130, NADH-101, NADH-110, P1-B02, P1-B05, P1-B10, P1-B12, P1-C01, P1-H08, P2-B02, P2-C11, P2-D03, P2-D11, P2-D12, P2-G03, P3-G09, and P3-H12.

Also disclosed herein is a synthetic method comprising aminating a second compound having the structure:

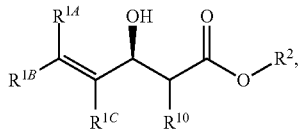

to form a third compound having the structure:

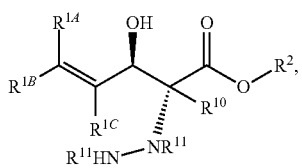

wherein each of $R^{1A}$, $R^{1B}$, and $R^{1C}$ is independently selected from hydrogen, aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, nitro, cyano, —C(O)O—$R^7$, —C(O)—$R^7$, ⁻COR$^7$, and —OR$^7$, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, ⁻COR$^7$, and —OR$^7$, wherein $R^2$ is selected from alkyl, alkenyl, alkynyl, haloalkyl, haloalkenyl, haloalkynyl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, ⁻COR$^7$, and —OR$^7$, wherein each $R^7$ is independently selected from hydrogen, alkyl, haloalkyl, polyhaloalkyl, alkylamino, dialkylamino, -alkyl-aryl, and -alkyl-heterocyclyl, wherein $R^{10}$ is selected from hydrogen, alkyl, alkenyl, or alkynyl, and wherein each $R^{11}$ is an amine protecting group.

Also disclosed herein, is a synthetic method comprising a) providing a first compound having the structure:

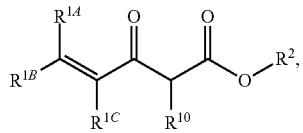

wherein each of $R^{1A}$, $R^{1B}$, and $R^{1C}$ is independently selected from hydrogen, aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, nitro, cyano, —C(O)O—$R^7$, —C(O)—$R^7$, ⁻COR$^7$, and —OR$^7$, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, ⁻COR$^7$, and —OR$^7$, wherein $R^2$ is selected from alkyl, alkenyl, alkynyl, haloalkyl, haloalkenyl, haloalkynyl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, ⁻COR$^7$, and —OR$^7$, wherein each $R^7$ is independently selected from hydrogen, alkyl, haloalkyl, polyhaloalkyl, alkylamino, dialkylamino, -alkyl-aryl, and -alkyl-heterocyclyl, wherein $R^{10}$ is selected from hydrogen, alkyl, alkenyl, or alkynyl;

b) reacting the first compound in the presence of a ketoreductase, thereby forming a second compound having the structure:

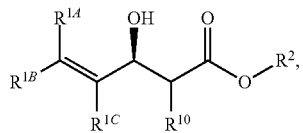

wherein the ketoreductase is 130, NADH-101, P3-G09, or P3-H12;

c) aminating the second compound to form a third compound having the structure:

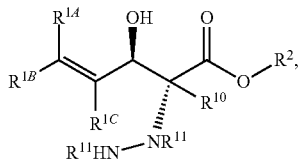

wherein $R^{11}$ is an amine protecting group, d) reducing the ester in the third compound to form an alcohol in a fourth compound;

e) protecting the alcohols in the fourth compound to form a fifth compound; and f) cleaving the N—N bond in the fifth compound to form a sixth having the structure

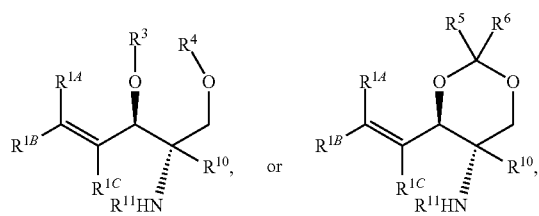

wherein $R^3$ and $R^4$ are alcohol protecting groups, or wherein $R^3$ and $R^4$ are linked together to form an alcohol protecting group, and wherein each of $R^5$ and $R^6$ is independently selected from hydrogen, alkyl, and aryl, or wherein $R^5$ and $R^5$ are linked together to form a cycloalkyl, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, $^-COR^7$, and —O$R^7$.

Ketoreductases can stereoselectively reduce ketoesters to hydroxy esters, such as β-hydroxy esters. Not all ketoreductases produces high enantiomeric excess of β-hydroxy esters from ketoesters. Furthermore, not all ketoreductases produce the same stereoselectivity in the production of β-hydroxy esters. Thus, one ketoreductase can form and R— or S—type β-hydroxy esters.

Ketoreductases 101, 119, 130, NADH-101, NADH-110, P1-B02, P1-B05, P1-B10, P1-B12, P1-C01, P1-H08, P2-B02, P2-C11, P2-D03, P2-D11, P2-D12, P2-G03, P3-G09, and P3-H12 can stereoselectively reduce:

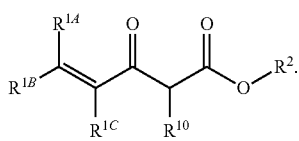

In one aspect, the ketoreductase is selected from 130, NADH-101, P3-G09, and P3-H12. For example, the ketoreductase can be 130. In another example, the ketoreductase can be NADH-101. In yet another example, the ketoreductase can be P3-G09. In yet another example, the ketoreductase can be P3-H12. The ketoreductase selected from 130, NADH-101, P3-G09, and P3-H12 can form:

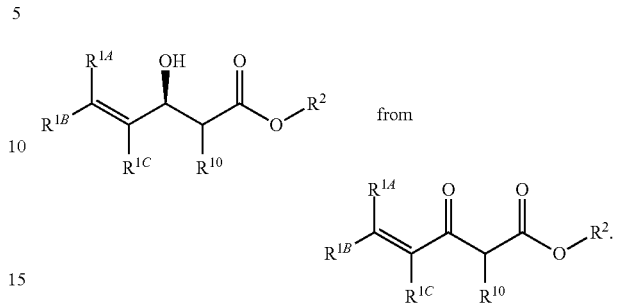

In general ketoreductases can be found in a wide range of bacteria and yeast (for reviews: Kraus and Waldman, Enzyme catalysis in organic synthesis, Vols. 1 and 2.VCH Weinheim 1995; Faber, K., Biotransformations in organic chemistry, 4th Ed. Springer, Berlin Heidelberg New York. 2000; Hummel and Kula, 1989, Eur. J. Biochem. 184: 1-13). Several KRED gene and enzyme sequences have been reported, e.g., *Candida magnoliae* (Genbank Ace. No. JC7338; GL 1 1360538) *Candida parapsilosis* (Genbank Ace. No. BAA24528.1; GI:2815409), *Sporobolomyces salmonicolor* (Genbank Ace. No. AF 160799; GL6539734).

Ketoreductases 101, 119, 130, NADH-101, NADH-110, P1-B02, P1-B05, P1-B10, P1-B12, P1-C01, P1-H08, P2-B02, P2-C11, P2-D03, P2-D11, P2-D12, P2-G03, P3-G09, and P3-H12 are commercially available from Codexis, Inc. Sequences of ketoreductases can be found in WO 2005/017135, which is hereby incorporated by reference in its entirety.

In one aspect, the method forms:

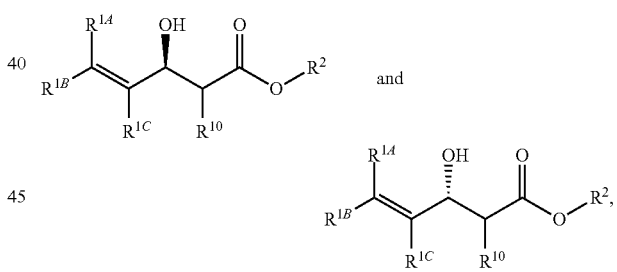

at least 90% enantiomeric excess. For example, the method can form:

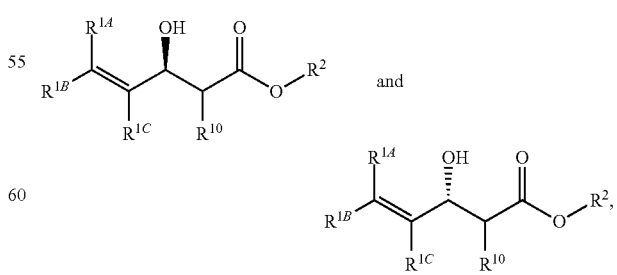

at least 90%, 91%, 92%, 93%, 94%, 95%, 96%, 97%, 98%, 99%, or 99.9% enantiomeric excess. In one example, the method can form:

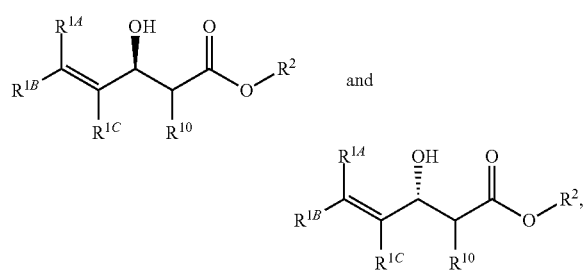

at least 99%, or 99.9% enantiomeric excess, such as at least 99% enantiomeric excess. In one aspect, the method forms:

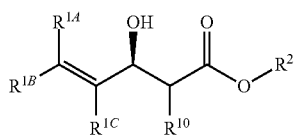

in an excess over:

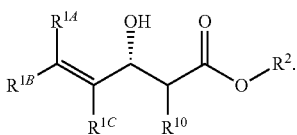

In one aspect, the method further comprises aminating the second compound to form a third compound having the structure:

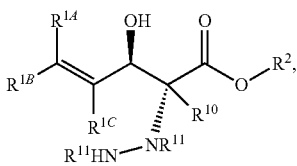

wherein each $R^{11}$ is an amine protecting group. The amination can be performed with a range of suitable amine containing compounds. Suitable amine containing compounds are azo ($R-N=N-R^7$) compounds. Suitable azo compounds include, but are not limited to, dibenzyl azodicarboxylate, diethyl azodicarboxylate (DEAD), and di-tert-butylazodicarboxylate (DBAD). As such, $R^{11}$ can be present in the azo compound used in the amination.

In one aspect, the method further comprises reducing the ester of the third compound to form an alcohol in a fourth compound. As such, the fourth compound comprises at least two alcohols. The fourth compound can have the structure:

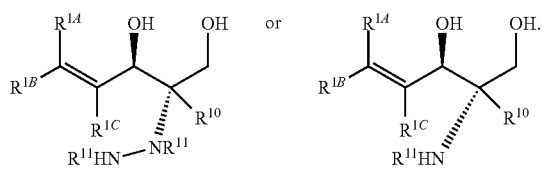

For example, the fourth compound can have the structure:

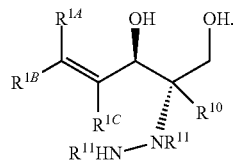

In one aspect, the N—N bond is cleaved simultaneously as the reduction of the ester. The fourth compound can then have the structure:

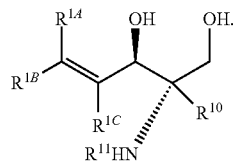

The reduction of the ester in the third compound can be achieved by the use of a variety of reaction conditions. For example, the $NaBH_4$ can be used to reduce the ester in the third compound to an alcohol. In another example, Red-Al (sodium bis(2-methoxyethoxy)aluminumhydride) can be used to both reduce the ester in the third compound and cleave the N—N bond in the third compound.

In one aspect, the alcohols in fourth compound are protected, thereby forming a fifth compound having the structure

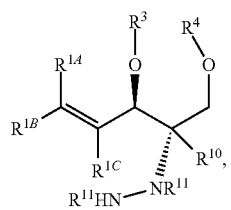

wherein $R^3$ and $R^4$ are alcohol protecting groups, or wherein $R^3$ and $R^4$ are linked together to form an alcohol protecting group.

In one aspect, the alcohol protecting groups are selected to retain the stereochemistry in the fourth compound. For example, $R^3$ and $R^4$ are linked together to form an alcohol protecting group.

In another aspect, the fifth compound has the structure:

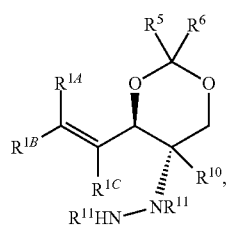

wherein each of $R^5$ and $R^6$ is independently selected from hydrogen, alkyl, and aryl, or wherein $R^5$ and $R^5$ are linked together to form a cycloalkyl, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, ⁻C(O)—$R^7$, —$COR^7$, and —$OR^7$.

A variety of $R^5$ and $R^6$ moieties can be used in the protecting group. For example, $R^5$ and $R^6$ can be a variety of suitable groups available in the formation of an acetal.

Protecting alcohols is common practice in synthetic chemistry and one skilled in the art is familiar with such synthetic strategy. For example, the formation of an acetal can be used to protect the two alcohol groups in the fourth compound.

In one aspect, the method further comprises cleaving the N—N bond in the fifth compound, thereby forming a sixth compound. The cleaving of the N—N bond can be achieved using a variety of chemical reactions. The protection of the alcohols in the fourth compound allows several possible reaction conditions to be used since the alcohols are protected and will not participate in reaction wherein the N—N bond is cleaved.

In one aspect, the sixth compound has the structure:

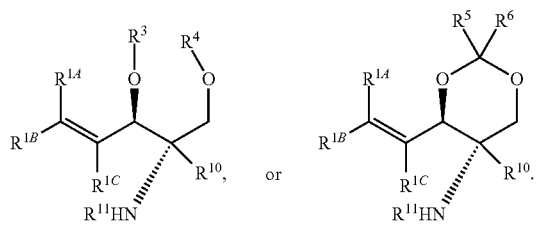

In one aspect, the method further comprises deprotecting both the alcohol protecting groups and amine protecting groups in the sixth compound in one or more steps, thereby forming a seventh compound. The sixth and/or seventh compounds are useful compounds due to their ability to be or be converted into biologically active compounds.

In one aspect the seventh compound has the structure:

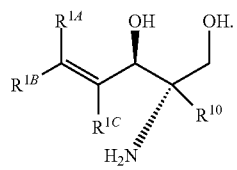

In another aspect, the seventh compound has the structure:

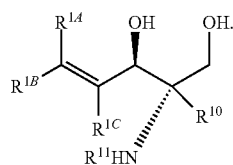

E. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

1. Chemistry Experimental

All chemicals were purchased from Sigma-Aldrich Chemical Company, unless otherwise noted. Spectroscopy grade chloroform was used for all optical rotation measurements. Cyclodextrins used for capillary electrophoresis, heptakis(2,3-di-O-methyl-6-O-sulfobutyl)cyclomaltoheptaose, sodium salt (NaSBDM-β-CD) and heptakis (2,3-di-O-ethyl-6-O-sulfopropyl)cyclomaltoheptaose potassium salt (KSP-DEβ-CD), were synthesized according to procedures reported in the literature (Kirschner et al., J. Mol. Catal. A: Chem. 2008, 286, 11). Codex® KRED screening kit was purchased from Codexis, Inc. Both reconstituted KRED Recycle Mix N (containing 250 mM potassium phosphate, 2 mM magnesium sulfate, 1.1 mM NADP+, 1.1 mM NAD+, 80 mM D-glucose, 10 U/mL glucose dehydrogenase, pH 7.0) and reconstituted KRED Recycle Mix P (containing 125 mM potassium phosphate, 1.25 mM magnesium sulfate, 1.0 mM NADP+, pH 7.0) are available from Codexis, Inc. Aluminum coated silica gel WF254s plates were used to monitor reaction products and flash chromatography eluents. Column chromatography was performed with silica gel SiliaFlash®P60 (40-60 μm, 230-400 mesh).

1H and 13C NMR spectra were recorded in CDCl3 solution with a Varian 300 MHz instrument. Chemical shifts are reported in ppm relative to TMS as internal standard. HPLC was performed on Agilent 1100 series with isocratic pump and UV-visible detector. A Phenomenex® Lux 3μ, cellulose-1 column (50×4.60 mm) was used for the chiral separation at 23° C. The mobile phase consisted of hexanes and isopropanol in the ratio of 90:10, with a flow rate of 0.5 mL/min. Optical rotations were measured on a Krüss P3000 polarimeter operating at the sodium D line 589 nm and reported as follows: $[\alpha]_{589}^{23}$, concentration (g/100 ml), and solvent. Capillary electrophoresis was performed with an Agilent 3D Capillary Electrophoresis System using bare fused silica capillary (purchased from Polymicro Technologies, L.L.C.) (50 µm i.d., 32.5 cm total length, 24.0 cm to detector) under reverse polarity (−10 or −15 kV), and detection by UV absorbance at 254 nm. Prior to first use, the capillary was primed for 2 min with 1 M NaOH solution and then for 2 min with 0.1 M NaOH solution. For each use, the capillary was preconditioned for 1 min using a background electrolyte (BGE). BGE was either 5.0 mM NaSBDM-β-CD or 5.0 mM KSPDE-β-CD as chiral selector in 25 mM tris buffer, pH 2.5. Samples (diluted 10 fold into 90:10 v/v deionized water/acetone solvent) were injected into the capillary under 50.0 mbar pressures for 3 seconds. At the end of each run, the capillary was post-conditioned with 0.1 M NaOH solution for 1 min and then with deionized water for 1 min.

Several methods for preparing the compounds of this invention are illustrated in the following examples. Starting materials and the requisite intermediates are in some cases commercially available, or can be prepared according to literature procedures or as illustrated herein.

a. Synthesis of Ethyl 4-(diethoxyphosphinyl)-3-oxobutanoate (3)

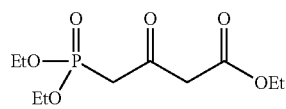 [SMILES: CCOC(=O)CC(=O)CP(=O)(OCC)OCC]

Ethyl 4-bromo-3-oxobutanoate (2) (7.0 g, 34 mmol) was added to triethyl phosphite (7.0 g, 42 mmol) at 90° C. within 2 min and stirred for an additional 15 min at 90° C. with a simultaneous release of ethyl bromide. Excess triethyl phosphite and traces of ethyl bromide were removed under vacuum. The resulting viscous oily mixture of diethylphosphonate (3) and enol diethyl-phosphonate (3') was shaken in an aqueous solution of potassium carbonate (7.0 g in 200 mL $H_2O$, pH 10) and then extracted 3× with a mixture of petroleum spirits (40-60° C.) and dichloromethane (19:1) (3×100 mL). Acidification of the aqueous layer with aqueous HCl, followed by extraction with dichloromethane gave ethyl 4-(diethyoxyphosphinyl)-3-oxobutanoate 3 (Moorhoff et al., *Synthetic Communications* 2003, 33, 2069).

b. Synthesis of γ,δ-Unsaturated b-Keto Ethyl Esters (4A-4F)

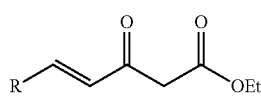

where R=Ph, 4-Me-Ph, 4-Cl-Ph, 4-$NO_2$-Ph, 4-nBu-Ph, Bn (E)-Ethyl 4-(diethoxyphosphinyl)-3-oxobutanoate (3) (2.2 g, 6.6 mmol) in 20 mL anhydrous THF was reacted with 2.0 equivalents of n-BuLi (6.0 mL, 13 mmol, 2.2 M in hexanes) at 0° C. After gas formation ceased, stirring was continued for 1 h at rt. One equivalent of aldehyde (6.0 mmol) was added over 10 min, and the reaction mixture was stirred at rt for another 2.5 h. After completion, the reaction was quenched by adding 15 mL of saturated $NH_4Cl$. The reaction mixture was concentrated under vacuum at 50-60° C. The residue was extracted by $CH_2Cl_2$ (3×15 mL), the combined organic extracts were washed with saturated NaCl (2×15 mL), and then dried with anhydrous $Na_2SO_4$. The organic solvent was removed under vacuum at 30° C. Product was isolated by chromatography on silica gel using 10:1 $CH_2Cl_2$/EtOAc and verified by $^1H$ and $^{13}C$ NMR spectroscopy.

c. Synthesis of Racemic γ,δ-Unsaturated b-Hydroxyesters (5A-5F)

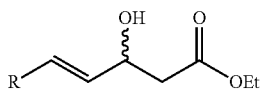

where R=Ph, 4-Me-Ph, 4-Cl-Ph, 4-$NO_2$-Ph, 4-nBu-Ph, Bn

In a round bottom flask β-ketoester (4A-4F) (1 mmol) was dissolved in 5 mL ethanol. In portion, cautiously and intermittently, 0.4 equivalent of $NaBH_4$ (15 mg, 0.4 mmol) was added and the mixture was stirred for 30 min at rt. The reaction mixture was concentrated under vacuum at 60° C. The product was isolated by chromatography on silica gel using 10:1 $CH_2Cl_2$/EtOAc and verified by $^1H$ and $^{13}C$ NMR spectroscopy.

d. Enzymatic Formation of γ,δ-Unsaturated β-Hydroxyesters (5A-5F) Using NADH System (enzymes 1-5)

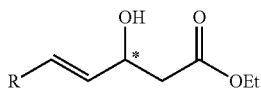

where R=Ph, 4-Me-Ph, 4-Cl-Ph, 4-$NO_2$-Ph, 4-nBu-Ph, Bn

Into a solution of β-ketoester (4A-4F) (25 µmmol) in 50 µL methanol, was added KRED Mix N (57.4 mg in 1.0 mL deionized $H_2O$) and 1.0 mg ketoreductase. The mixture was shaken at 32±1° C. After 24 h, the reaction was extracted by EtOAc (2×1 mL). The combined organic extract was dried over anhydrous $Na_2SO_4$ and was subjected to chiral HPLC or CE analysis, and $^1H$ NMR spectroscopy.

e. Enzymatic Formation of γ,δ-Unsaturated β-Hydroxyesters (5A-5F) Using NADPH System (enzymes 6-24)

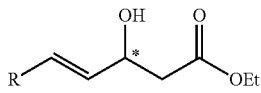

where R=Ph, 4-Me-Ph, 4-Cl-Ph, 4-$NO_2$-Ph, 4-nBu-Ph, Bn

Into a solution of β-ketoester (4A-4F) (25 µmol) in 400 µL isopropanol and 50 µL methanol, was added KRED Mix P (29.1 mg in 1.0 mL deionized $H_2O$) and 1.0 mg ketoreductase. The mixture was stirred at 32±1° C. After 24 h, the reaction was extracted by EtOAc (2×1 mL). The combined organic extract was dried over anhydrous $Na_2SO_4$ and was subjected to chiral HPLC or CE analysis, and $^1H$ NMR spectroscopy. For β-ketoesters 2A-2D, the reactions were scaled up by a factor of 20 or 100 using enzymes that yielded high conversions and e.e., and all products were isolated by chromatography on silica gel using 10:1 CH₂Cl₂/EtOAc, and verified by ¹H and ¹³C NMR spectroscopy.

f. Synthesis of Di-tert-butyl 1-((3R,E)-1-ethoxy-3-hydroxy-1-oxo-5-(p-tolyl)pent-4-en-2-yl)hydrazine-1,2-dicarboxylate (6B)

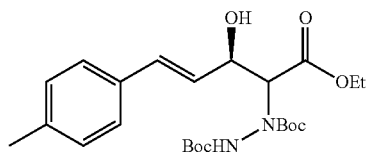 [SMILES: CCOC(=O)C([C@H](O)/C=C/c1ccc(C)cc1)N(NC(=O)OC(C)(C)C)C(=O)OC(C)(C)C]

To a solution of 3-hydroxyl-5-phenyl-4-pententoic acid, methyl ester 5 (178 mg, 0.87 mmol) in 2 mL anhydrous THF at 0° C., zinc methyl bromide (1.2 equiv., 1.0 mmol, 2.6 mL, 0.4 M in THF) was added slowly, and the reaction mixture was stirred for 1 h. After the reaction was cooled to −78° C., 2.0 equiv. of LDA (1.7 mmol, 0.87 mL, 2 M in heptane/THF/ethyl benzene) in 2 mL anhydrous THF was added dropwise. After 1 h at −78° C., a solution of DBAD (401 mg, 1.7 mmol) in 1 mL anhydrous THF was added slowly, the reaction mixture continued to stir for another 2 h. The reaction mixture was quenched at −78° C. with saturated NH₄Cl solution (aq.) (4 mL), warmed to rt, extracted with Et₂O (2×10 ml). The combined organic layers were dried over anhydrous MgSO₄ and concentrated in vacuo to afford the crude product. Purification by chromatography on silica gel using 100% CH₂Cl₂ to elute unreacted DBAD, then gradient elution using 10:1/CH₂Cl₂: EtOAc to afford hydrazino (6B) as a white solid (58%). Diastereomeric excess (d.e.)>99% (Girard et al., *Tet. Lett.* 1996, 37, 7967; Labeeuw et al., *Tet. Lett.* 2003, 44, 6383).

g. Synthesis of γ,δ-Unsaturated-anti-N,N-boc-α-hydrazino-β-hydroxyl ester (6C)

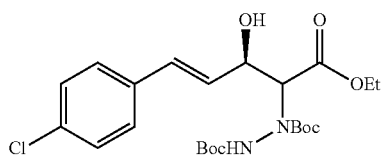 [SMILES: CCOC(=O)C([C@H](O)/C=C/c1ccc(Cl)cc1)N(NC(=O)OC(C)(C)C)C(=O)OC(C)(C)C]

To a solution of 3-hydroxyl-5-parachlorophenyl-4-pententoic acid, ethyl ester (5C) (347 mg, 1.4 mmol) in 4 mL anhydrous THF at 0° C., zinc methyl bromide (1.2 equiv., 1.6 mmol, 4.1 mL, 0.4 M in THF) was added slowly, and the reaction mixture was stirred for 1 h. After the reaction was cooled to −78° C., 2.0 equiv of LDA (2.7 mmol, 1.3 mL, 2 M in heptane/THF/ethyl benzene) was added dropwise. After 1 h at −78° C., a solution of DBAD (626 mg, 2.7 mmol) in 2 mL anhydrous THF was added slowly, and the reaction mixture continued to stir for another 2 h. The reaction mixture was quenched at −78° C. with saturated NH₄Cl solution (aq.) (6 mL), warmed to rt, extracted with EtOAc (2×15 mL). The combined organic layers were dried over anhydrous MgSO₄ and concentrated in vacuo to afford the crude product. Purification by chromatography on SiO₂ using 100% CH₂Cl₂ to elute unreacted DBAD, then gradient elution using 10:1/CH₂Cl₂:EtOAc to afford hydrazine (6C) as a white solid (58%). Diastereomeric excess (d.e.)>99% (Girard et al., *Tet. Lett.* 1996, 37, 7967; Labeeuw et al., *Tet. Lett.* 2003, 44, 6383).

h. Synthesis of Di-tert-butyl 1-((3R,E)-1,3-dihydroxy-5-(p-tolyl)pent-4-en-2-yl)hydrazine-1,2-dicarboxylate (7B)

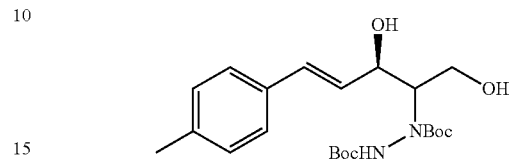

β-hydroxy-α-hydrazino ester (6B) (465 mg, 1.0 mmol) was added to 25 mL MeOH, then 3.0 eq of NaBH₄ (114 mg, 3.0 mmol) was added every 15 min until the starting material was consumed as indicated by TLC. The reaction was quenched with saturated NH₄Cl (aq.), extracted with EtOAc, and the combined extracts were washed with brine, dried over anhydrous Na₂SO₄, and the solvent was removed in vacuo. Purification by chromatography on silica gel to afford the desired product as a white solid (83%) (Kim et al., *Tetrahedron* 2010, 66, 3995).

i. Synthesis of Di-tert-butyl 1-((3R,E)-5-(4-chlorophenyl)-1,3-dihydroxypent-4-en-2-yl)hydrazine-1,2-dicarboxylate (7C)

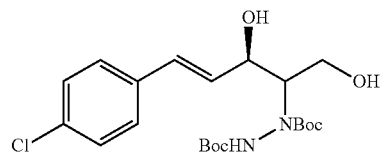 [SMILES: CC(C)(C)OC(=O)NN(C(=O)OC(C)(C)C)C(CO)[C@H](O)/C=C/c1ccc(Cl)cc1]

In a round bottom flask, β-hydroxy-α-hydrazino ester (6C) (214 mg, 0.44 mmol) was dissolved in 11 mL MeOH. 3.0 equiv. of NaBH₄ (114 mg, 3.0 mmol) was added every 15 min. The reaction mixture was stirred at rt and monitored by TLC (10:1/CH₂Cl₂/EtOAc) until the starting material was consumed. The reaction was quenched with saturated NH₄Cl (eq.), extracted with EtOAc, and the combined extracts were washed with brine, dried over anhydrous Na₂SO₄, and the solvent was removed in vacuo. Purification by chromatography on silica gel afforded the desired product as a white solid (81%) (Kim et al., *Tetrahedron* 2010, 66, 3995).

j. Synthesis of Di-tert-butyl 1-((4R)-2,2-dimethyl-4-((E)-4-methylstyryl)-1,3-dioxan-5-yl)hydrazine-1,2-dicarboxylate (8B)

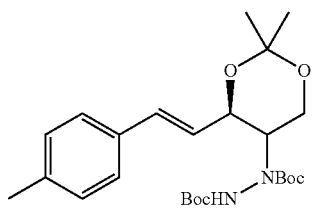

A mixture of 1,3-diol, 2-hydrazino (7B) (59 mg, 0.14 mmol) and p-toluene sulfonic acid monohydrate (2.7 mg, 0.014 mmol) in 5.0 mL anhydrous acetone was stirred at rt for 42 h. The reaction mixture was quenched with 5% NaHCO$_3$ and extracted with CH$_2$Cl$_2$. The combined organic layers were dried over anhydrous Na$_2$SO$_4$, and removed in vacuo. Purification by flash chromatography on silica gel afforded the desired product as a white solid (94%).

k. Synthesis of Di-tert-butyl 1-((2R)-2-((E)-4-chlorostyryl)-6,6-dimethyltetrahydro-2H-pyran-3-yl)hydrazine-1,2-dicarboxylate (8C)

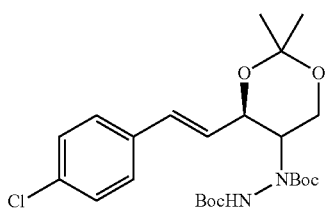

A mixture of 1,3-diol, 2-hydrazino (7C) (158 mg, 0.35 mmol) and p-toluene sulfonic acid monohydrate (6.8 mg, 0.035 mmol) in 10 mL anhydrous acetone was stirred at rt for 36 h, until the starting material was consumed as indicated by TLC (10:1/CH$_2$Cl$_2$/EtOAc). The reaction mixture was quenched with 5% NaHCO$_3$ and extracted by CH$_2$Cl$_2$. The combined organic layers were dried over anhydrous Na$_2$SO$_4$, and removed in vacuo. Purification by flash column chromatography on silica gel afforded the desired product as a white solid (93%).

l. Synthesis of tert-Butyl ((4R)-2,2-dimethyl-4-((E)-4-methylstyryl)-1,3-dioxan-5-yl)carbamate (10B)

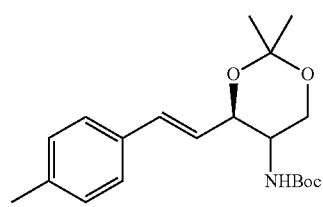

To a suspension of 1,3-ketal-2-hydrazino (8B) (23 mg, 0.05 mmol) and Cs$_2$CO$_3$ (41 mg, 0.13 mmol) in 0.5 mL CH$_3$CN, was added methyl bromoacetate (17 mg, 0.10 mmol) in 0.5 mL CH$_3$CN. The reaction mixture was heated at 50° C. for 3 h. The reaction mixture was then refluxed until the intermediate was consumed as indicated by TLC. The reaction mixture was quenched with saturated NH$_4$Cl (aq.), and extracted with EtOAc. The combined extracts were washed with brine, dried over anhydrous Na$_2$SO$_4$, and the solvent was removed in vacuo. Purification by flash chromatography on silica gel afforded the desired product as a white solid (90%) (Magnus et al., *Org. Lett.* 2009, 11, 5646).

m. Synthesis of tert-Butyl ((2R)-2-((E)-4-Chlorostyryl)-6,6-dimethyltetrahydro-2H-pyran-3-yl)carbamate (10C)

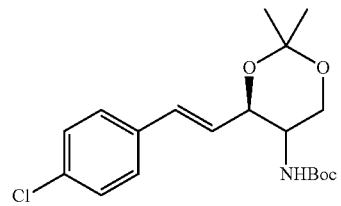

To a suspension of 1,3-ketal-2-hydrazino (8C) (117 mg, 0.24 mmol) and Cs$_2$CO$_3$ (199 mg, 0.61 mmol) in 2.5 mL CH$_3$CN, was added methyl bromoacetate (75 mg, 0.48 mmol) in 1.0 mL CH$_3$CN. The reaction mixture was heated at 50° C. for 3 h. The reaction mixture was then refluxed until the intermediate was consumed as indicated by TLC. The reaction mixture was quenched with saturated NH$_4$Cl (aq.) and extracted with EtOAc. The combined organic extracts were washed with brine, dried over anhydrous Na$_2$SO$_4$, and the solvent was removed in vacuo. Purification by flash chromatography on silica gel afforded the desired product as a white solid (83%) (Magnus et al., *Org. Lett.* 2009, 11, 5646).

n. Synthesis of tert-Butyl ((3R,E)-1,3-dihydroxy-5-(p-tolyl)pent-4-En-2-yl)carbamate (11B)

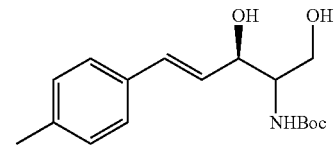 [SMILES: Cc1ccc(/C=C/[C@@H](O)C(CO)NC(=O)OC(C)(C)C)cc1]

1,3-Dioxane, 2-boc amino (10B) and 10 mol % TsOH were combined in 5.0 mL THF and 5.0 mL H$_2$O and stirred at reflux until the starting material was consumed as indicated by TLC. The reaction mixture was quenched with 5% NaHCO$_3$ and extracted with CH$_2$Cl$_2$. The combined organic layers were dried over anhydrous Na$_2$SO$_4$, and removed in vacuo. Purification by flash chromatography on silica gel afforded the desired product as a white solid (95%).

o. Synthesis of tert-Butyl ((3 R,E)-5-(4-chlorophenyl)-1,3-dihydroxypent-4-en-2-yl)carbamate (11C)

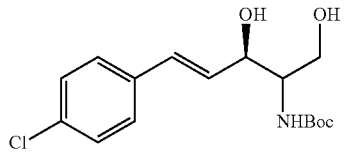 [SMILES: CC(C)(C)OC(=O)NC(CO)[C@H](O)/C=C/c1ccc(Cl)cc1]

1,3-Dioxane, 2-boc amino (10C) (18 mg, 0.05 mmol) and 10 mol % TsOH (1.0 mg, 0.005 mmol) were combined in 5.0 mL 80% EtOH (in H$_2$O) and stirred at reflux for 1 h, until the starting material was consumed as indicated by TLC (5:3/ CH₂Cl₂:EtOAc). The reaction mixture was quenched with 5% NaHCO₃, and removed in vacuo. Purification by flash column chromatography on silica gel afforded the desired product as a white solid (92%).

p. Synthesis of MTPA Ester of γ,δ-Unsaturated β-Hydroxyesters

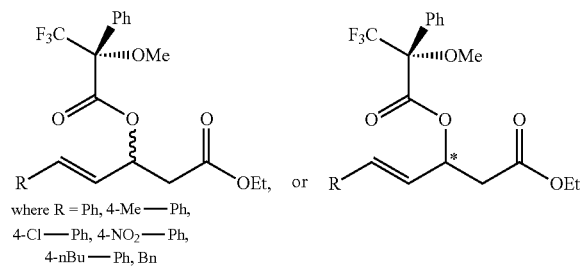

Product MTPA esters were prepared using a method previously described (Hoye et al., *Nat. Protoc.* 2007, 2, 2451). Briefly, into a solution of 64 μmol β-hydroxyester (3A-3F) (racemic or made by enzyme 8 KRED-P1-B05 or enzyme 23 KRED-P3-G09) and dry pyridine (16 μL, 200 μmol, 3.1 equiv.) in 1.0 mL anhydrous CH₂Cl₂, was added the R-(−)-MTPA-Cl (23 μL, 120 μmol, 1.9 equiv.). The reaction mixture was stirred at ambient temperature till the reaction was completed as monitored by TLC plate (eluent: 10:1=CH₂Cl₂: EtOAc) (approx. 3 h). After completion, the reaction was quenched by 2 mL H₂O, extracted by EtOAc (2×5 mL). The combined organic layer were dried over anhydrous Na₂SO₄ and removed under vacuo. The product MTPA ester of γ,δ-unsaturated β-hydroxyesters was isolated by chromatography on silica gel using 10:1 CH₂Cl₂/EtOAc.

2. Results and Discussion a. Preparation of γ,δ-Unsaturated β-Keto Ethyl Esters (4A-4F)

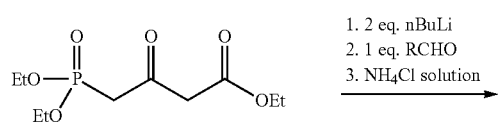

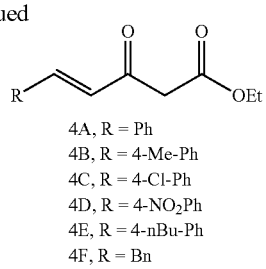

4A, R = Ph
4B, R = 4-Me-Ph
4C, R = 4-Cl-Ph
4D, R = 4-NO₂Ph
4E, R = 4-nBu-Ph
4F, R = Bn

By optimizing previously reported procedures (Svendsen and Boll, *Tetrahedron* 1973, 29, 4251; Bodalski et al., *Tet. Lett.* 1980, 21, 2287; Vandengoorbergh and Vandergen, *Tet. Lett.* 1980, 21, 3621; Moorhoff and Schneider, *Tet. Lett.* 1987, 28, 559; du Pisani et al., *Synthetic Communications* 2002, 32, 305), synthesis of γ,δ-unsaturated β-keto ethyl esters (4A-F) was accomplished via the condensation of appropriate aldehydes with pretreated 4-(diethoxyphosphinyl)-3-oxobutanoate (Moorhoff, C. M., *Synthetic Communications* 2003, 33, 2069) by two equivalents of n-BuLi at room temperature. No Z-olefins were detected by ¹H NMR (E-olefins have a coupling constant with a value of 15 Hz in ¹H NMR spectrometry). The condensation afforded yields of 75%-90% for 4A-E; ketoester 4F was formed in only 15% yield when phenylacetaldehyde was used under the same reaction conditions. A significant by-product was obtained because the α-hydrogen of phenylacetaldehyde is activated by the phenyl and formyl groups and easily deprotonated under basic conditions, followed by intermolecular aldol condensation.

b. Stereoselectivity of Enzymatic Formation of β-Hydroxyesters (5A-5F)

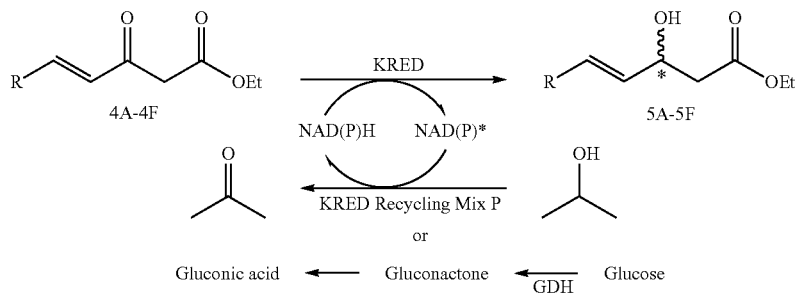

The five para-substituted phenyl (4A-E) and one benzyl (4F) γ,δ-unsaturated β-ketoesters were selected as substrates to evaluate the stereoselectivity of twenty-four isolated ketoreductases listed in Table 1 below from the Codex® ketoreductase screening kit, which includes five wild type KREDs 1-5 and nineteen engineered KREDs 6-24. All KREDs reactions used NADPH recycle system except enzyme 4 (KRED-NADH-101) and 5 (KRED-NADH-110), which used NADH instead of NADPH, as shown above. For engineered KREDs 6-24 which have high tolerance to high concentration of isopropanol (IPA), IPA was used to assist in dissolving poor water soluble substances and served to recycle NADPH cofactor from NADP+, and the reconstituted KRED recycle Mix P serviced as the reaction medium. However, for wild type KREDs 1-5, the reconstituted KRED recycle Mix N containing D-glucose/glucose dehydrogenase (GDH) and NAD(P)+ was used to provide a cofactor recycle system. In each case, methanol was used as a co-solvent to enhance the solubility of β-ketoesters, but the amount of co-solvent was no more than 5% of the total volume of reaction solution as recommended in the protocol provided by Codexis.

TABLE 1

| Enzyme No. | KRED |
|---|---|
| 1 | 101 |
| 2 | 119 |
| 3 | 130 |
| 4 | NADH-101 |
| 5 | NADH-110 |
| 6 | P1-A04 |
| 7 | P1-B02 |
| 8 | P1-B05 |
| 9 | P1-B10 |
| 10 | P1-B12 |

Figure 28:
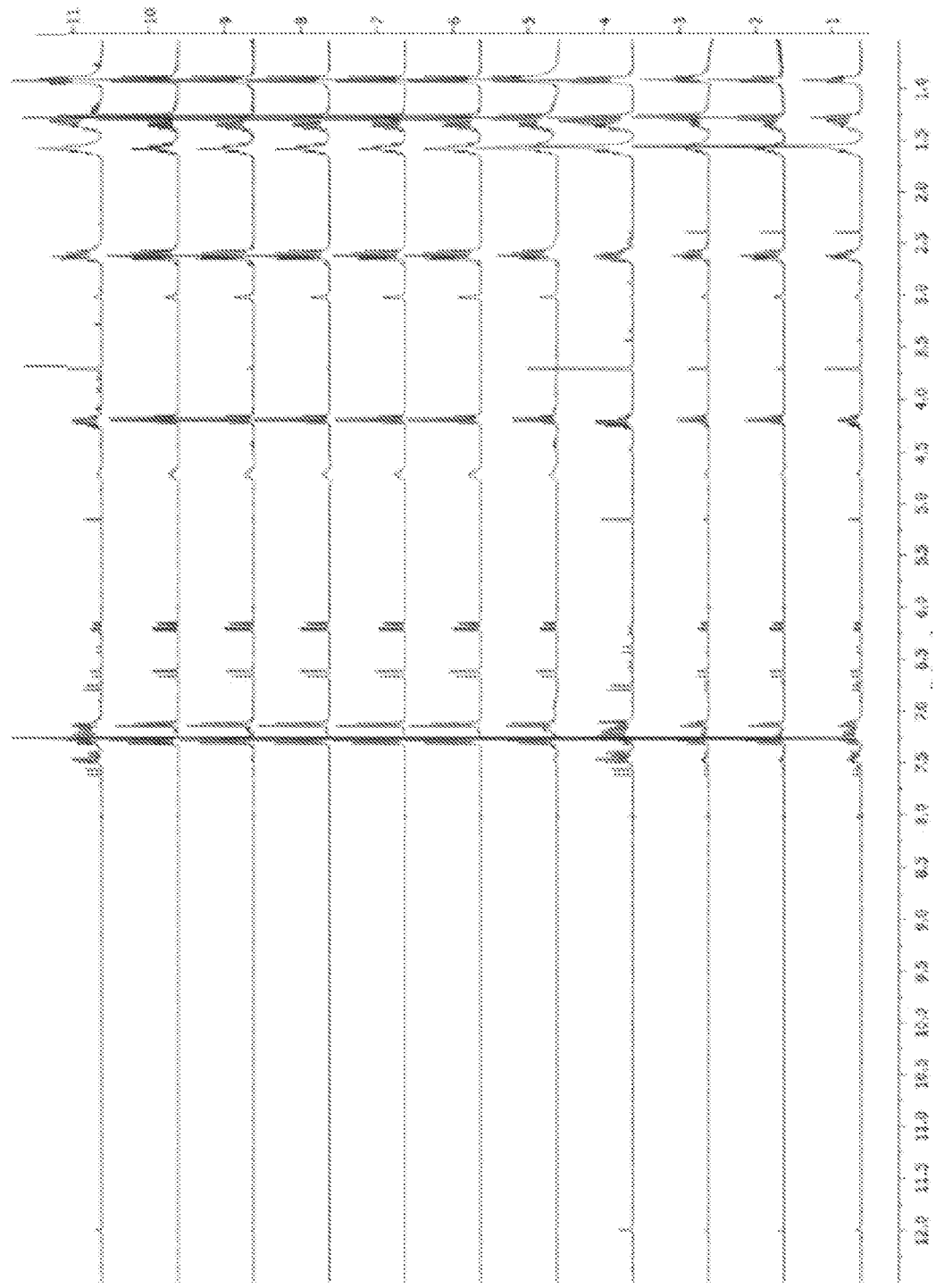
FIG. 28 shows stacked $^{1}$H NMR spectra of crude enzymatic product 3E in CDCl$_3$. 1): Enzyme #1; 2): Enzyme #2; 3): Enzyme #3; 4): Enzyme #5; 5): Enzyme #7; 6): Enzyme #8; 7): Enzyme #14; 8): Enzyme #15; 9): Enzyme #16; 10): Enzyme #20; 11): Enzyme #23.

In the protocol provided by Codex®, 1-4 mg of KREDs was recommended to reduce 1 mmol of substance. Different from that in the protocol, in our experiment 40 mg/mmol ratio of KREDs relative to unsaturated β-ketoesters was used to perform all the microscale reactions (using 25 μmol of unsaturated β-ketoesters) shown in Table 2. All reactions were carried at 30-32° C. Approximate yields for the microscale reactions were determined by integration of the vinyl hydrogen regions of the $^1$H NMR spectra of the crude mixtures, which also served to establish whether substantial byproducts formed and whether the double bond was reduced. There was no evidence of double bond reduction in any reaction. When conversion of β-ketoesters was greater than 3%, only the presence of unreacted β-ketoesters and product β-hydroxyester was observed in the spectrum (see FIG. 28).

TABLE 2

| | 3A | | 3B | | 3C | | 3D | | 3E | | 3F | | 3F' | |
|---|---|---|---|---|---|---|---|---|---|---|---|---|---|---|
| Enzyme No. | e.e.[a,b] % | Conv.[c] (%) | e.e.[a,b] % | Conv.[c] (%) | e.e.[b] % | Conv.[c] (%) | e.e.[a,b] % | Conv.[c] (%) | e.e.[a] % | Conv.[c] (%) | e.e.[a] % | Conv.[c] (%) | e.e.[a] % | Conv.[c] (%) |
| 1 | >99 | 92 | >99 | 67 | >99 | 77 | >99 | 62 | >99 | 49 | 91 | >99 | — | — |
| 2 | >99 | 94 | >99 | 96 | 94 | 95 | >99 | 24 | >99 | 87 | 96 | >99 | — | — |
| 3 | ->99 | 84 | ->99 | 84 | -93 | 85 | ->99 | 6 | ->99 | 74 | -85 | 81 | — | — |
| 4 | ->99 | w | ->99 | w | — | — | <3 | <3 | — | — | ->99 | 50 | — | — |
| 5 | >99 | 94 | >99 | 75 | >99 | 66 | >99 | 13 | >99 | 8 | >99 | >99 | — | — |
| 6 | — | — | — | — | — | — | — | — | — | — | — | — | — | — |
| 7 | 84 | 88 | 90 | 90 | >99 | >99 | >99 | 86 | 54 | 87 | 98 | 97 | 8 | 3 |
| 8 | >99 | >99 | >99 | 79 | >99 | >99 | >99 | 92 | >99 | >99 | 82 | 89 | 90 | 11 |
| 9 | 53 | 28 | 84 | 13 | 68 | 40 | 72 | <3 | — | — | 52 | <3 | -68 | <3 |
| 10 | 49 | 31 | 45 | 28 | 50 | <3 | >99 | <3 | — | — | 38 | <3 | -76 | <3 |
| 11 | 90 | <3 | — | — | — | — | — | — | — | — | — | — | — | — |
| 12 | 98 | <3 | 95 | 8 | 40 | <3 | 54 | <3 | — | — | — | — | — | — |
| 13 | — | — | — | — | — | — | — | — | — | — | 48 | <3 | 14 | <3 |
| 14 | >99 | >99 | >99 | >99 | >99 | >99 | 96 | 96 | >99 | >99 | >99 | 97 | 95 | 3 |
| 15 | >99 | 93 | >99 | >99 | >99 | >99 | 25 | 90 | >99 | >99 | >99 | 98 | >99 | 2 |
| 16 | >99 | 96 | >99 | 93 | >99 | >99 | >99 | 96 | >99 | 98 | >99 | 94 | >99 | 6 |
| 17 | 94 | <3 | — | — | 80 | <3 | — | — | — | — | — | — | — | — |
| 18 | 96 | 33 | >99 | 10 | 92 | <3 | — | — | — | — | — | — | — | — |
| 19 | 95 | <3 | 96 | <3 | 82 | <3 | — | — | — | — | — | — | -46 | <3 |
| 20 | >99 | 94 | >99 | 97 | >99 | >99 | >99 | 81 | >99 | >99 | >99 | >99 | — | — |
| 21 | — | — | — | — | — | — | — | — | — | — | — | — | — | — |
| 22 | — | — | — | — | — | — | — | — | — | — | — | — | — | — |
| 23 | ->99 | 15 | ->99 | 38 | ->99 | >99 | ->99 | 73 | ->99 | 40 | ->99 | 43 | ->99 | 9 |
| 24 | ->99 | 8 | ->99 | <3 | ->99 | 20 | ->99 | 43 | ->99 | 15 | -90 | 62 | 21 | 31 |

[a]Percent e.e. was measured by chiral HPLC. The positive e.e. value indicates that the (R)-enantiomer is the major product, while negative e.e. value indicates that the (S)-enantiomer is the major product. In each case, the racemic mixture was prepared for calibration. Absolute configuration of stereogenic C-3 was identified by $^1$H NMR analysis of the corresponding MTPA ester (Hoye et al., *Nat. Protoc.* 2007, 2, 2451).
[b]Percent e.e. was determined by CE using charged β-CD as a chiral selector.
[c]The conversion was obtained by $^1$H NMR integration using d-chloroform as a solvent. When <3% conversion is reported, the presence of byproducts made the measurement uncertain, although a small amount of product is detected. If no value is given, the product was not detected by either HPLC, CE, $^1$H NMR spectroscopy or TLC.

TABLE 1-continued

| Enzyme No. | KRED |
|---|---|
| 11 | P1-C01 |
| 12 | P1-H08 |
| 13 | P1-H10 |
| 14 | P2-B02 |
| 15 | P2-C02 |
| 16 | P2-C11 |
| 17 | P2-D03 |
| 18 | P2-D11 |
| 19 | P2-D12 |
| 20 | P2-G03 |
| 21 | P2-H07 |
| 22 | P3-B03 |
| 23 | P3-G09 |
| 24 | P3-H12 | enantiomer is the major product, while negative e.e. value indicates that the (S)-enantiomer is the major product. In each case, the racemic mixture was prepared for calibration. Absolute configuration of stereogenic C-3 was identified by $^1$H NMR analysis of the corresponding MTPA ester (Hoye et al., *Nat. Protoc.* 2007, 2, 2451). [b]Percent e.e. was determined by CE using charged β-CD as a chiral selector. [c]The conversion was obtained by $^1$H NMR integration using d-chloroform as a solvent. When <3% conversion is reported, the presence of byproducts made the measurement uncertain, although a small amount of product is detected. If no value is given, the product was not detected by either HPLC, CE, $^1$H NMR spectroscopy or TLC.

The data reported in Table 2 present the results of the reduction of γ,δ-unsaturated β-ketoesters under the action of twenty-four KREDs 1-24. With the exception of eight enzymes (P1-A04, P1-C01, P1-H08, P1-H10, P2-D03, P2-D12, P2-H07 and P2-D11) which have no (or very weak) effects on the conversion of β-ketoesters and two enzymes (P1-B10 and P1-B12) which provide low to medium enantiomeric excess of the desired β-hydroxyesters, most enzymes showed activity and excellent stereoselectivity for the reduction of β-ketoesters 4A-4F toward β-hydroxyesters 5A-5F. We do not discern any trends, either in terms of e.e. or conversion, as the substituent on the aromatic rings changes from weakly electron-donating (4B and 4E, alkyl) to strongly electron-withdrawing (4D, nitro).

c. Absolute Configuration of β-Hydroxyesters (5A, 5B, 5C, and 5E)

Figure 4:
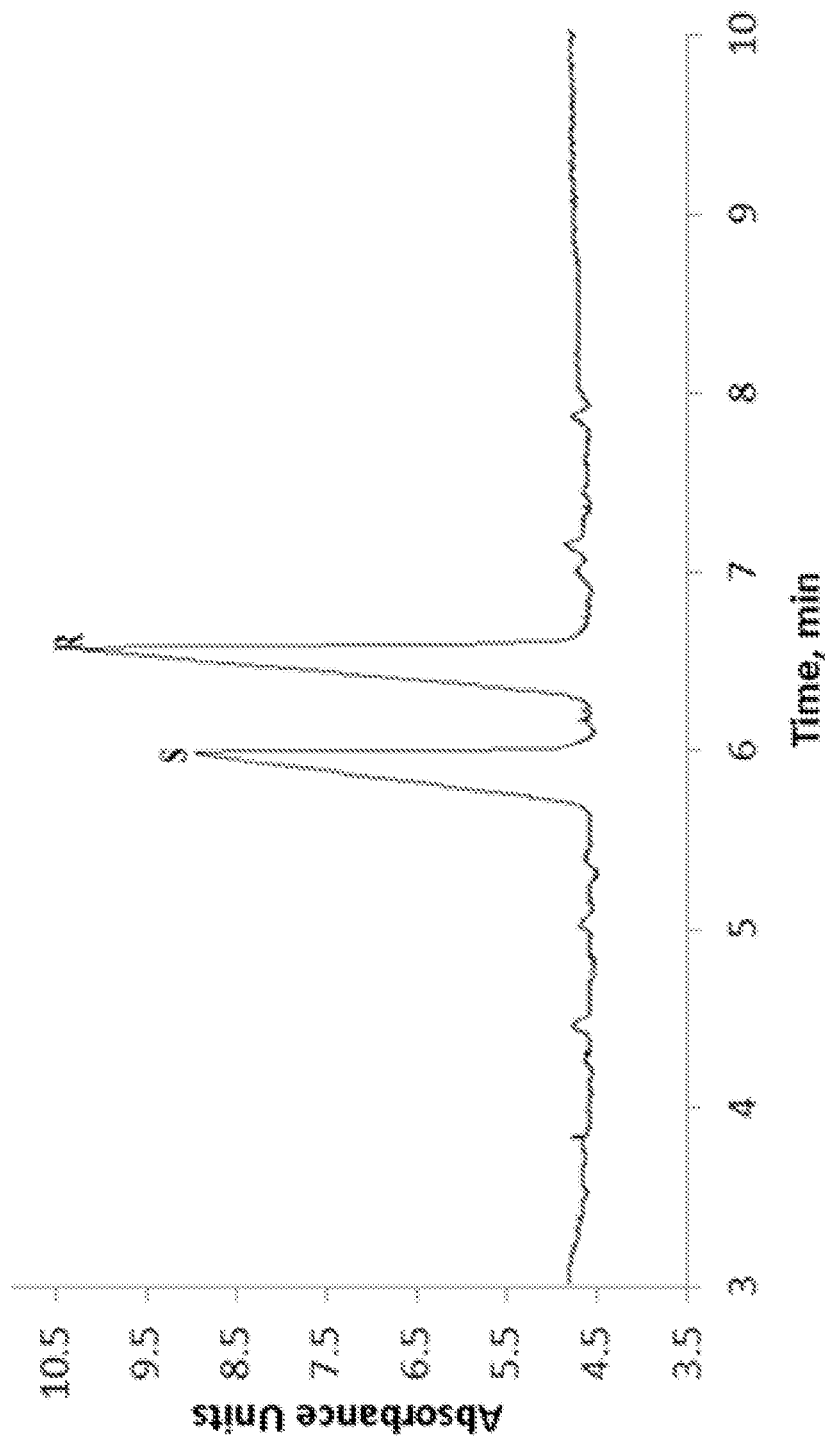
FIG. 4 shows a capillary electrophoresis trace of racemic 3-hydroxyl-5-para-chlorophenyl-4-pentenoic acid ethyl ester (5C). The conditions used were as follows: capillary: 50 μm i.d., 32.5 cm total, 24.5 cm to the detector; voltage: −20.0 KV (reverse polarity); buffer: 25.0 mM phosphate buffer, pH=2.5; 15.0 mM KSPDE-β-CD; injection: 50.0 mBar/ls.
Figure 5:
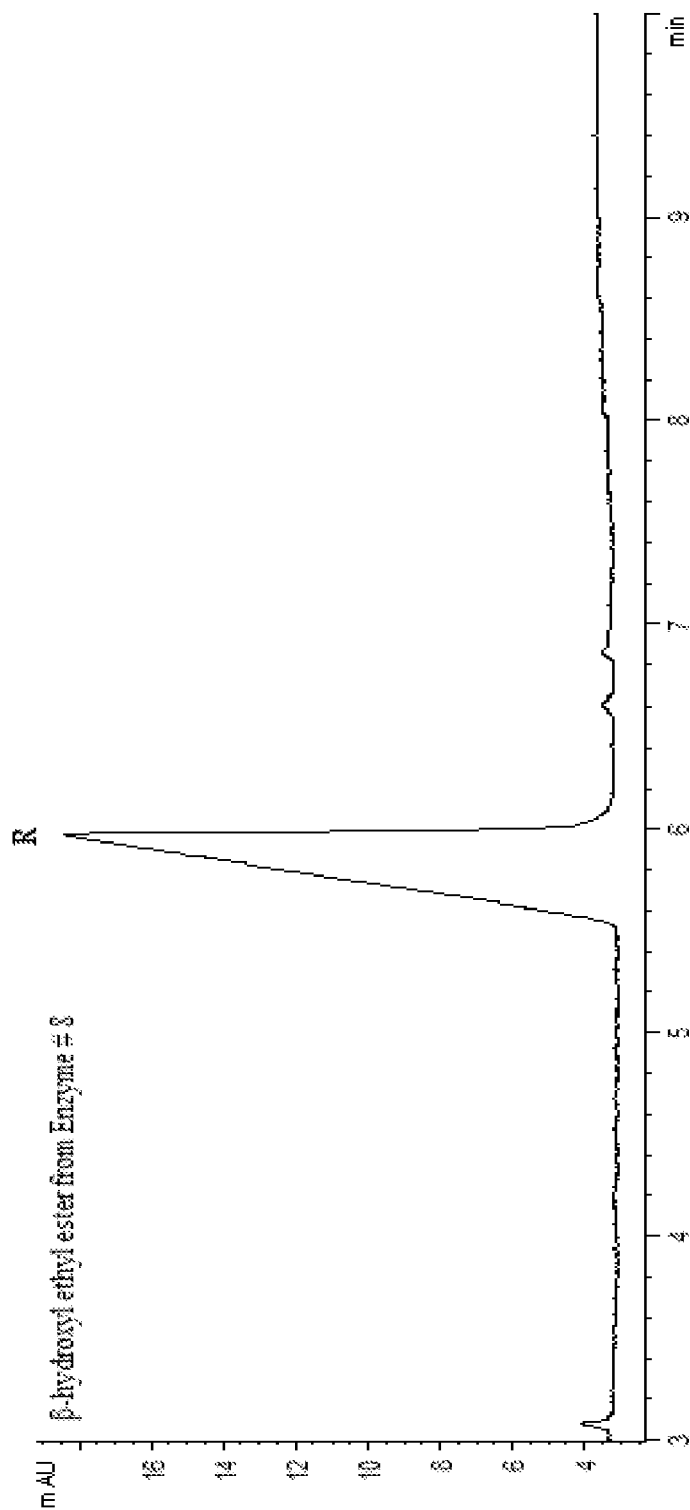
FIG. 5 shows a capillary electrophoresis trace of 3-hydroxyl-5-para-chlorophenyl-4-pentenoic acid ethyl ester (5C) prepared via enzymatic reduction using ketoreductase P1-B05 (enzyme 8). The conditions utilized were as described above.
Figure 6:
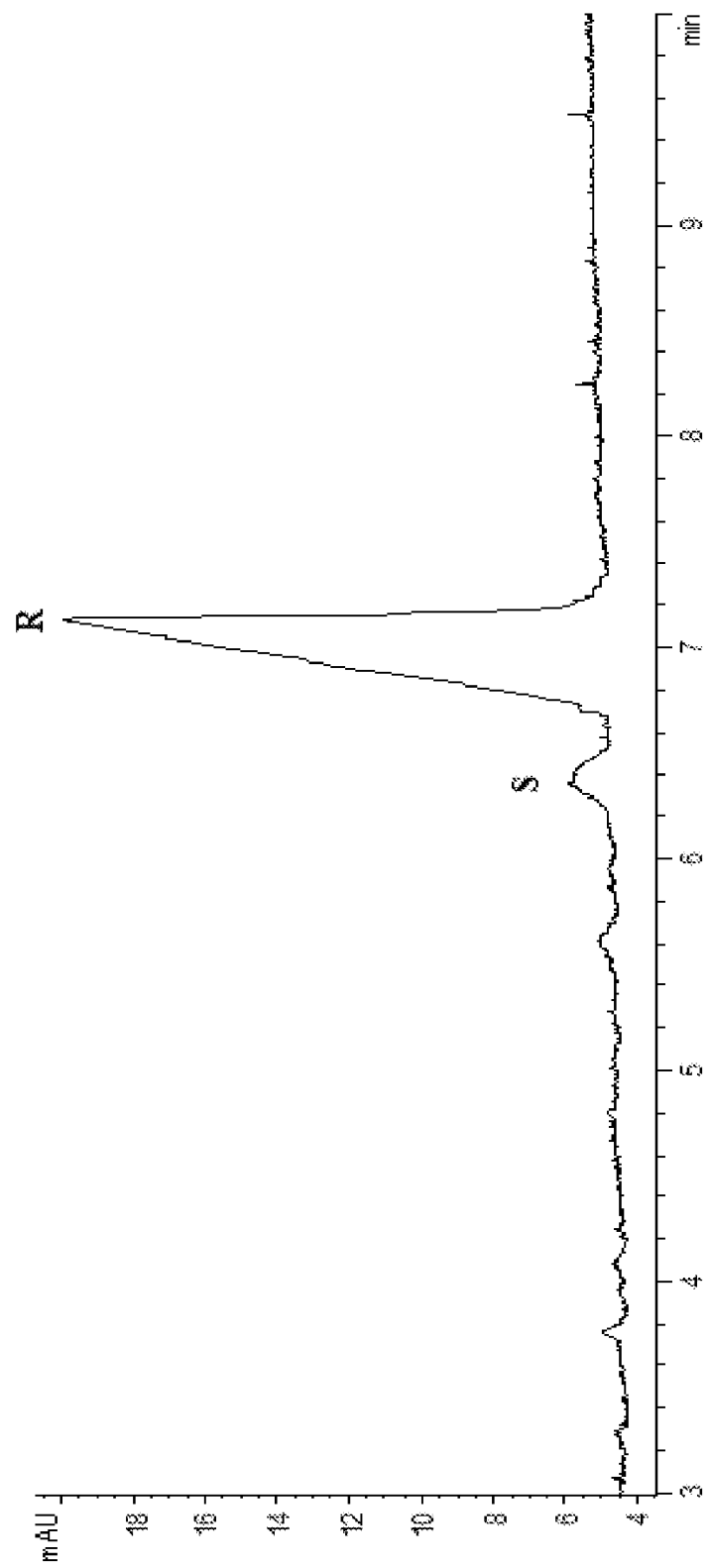
FIG. 6 shows a capillary electrophoresis trace of 3-hydroxyl-5-para-chlorophenyl-4-pentenoic acid ethyl ester (5C) prepared via enzymatic reduction using ketoreductase P1-B05 (enzyme 8) spiked with the racemic mixture. The conditions utilized were as described above.
Figure 7:
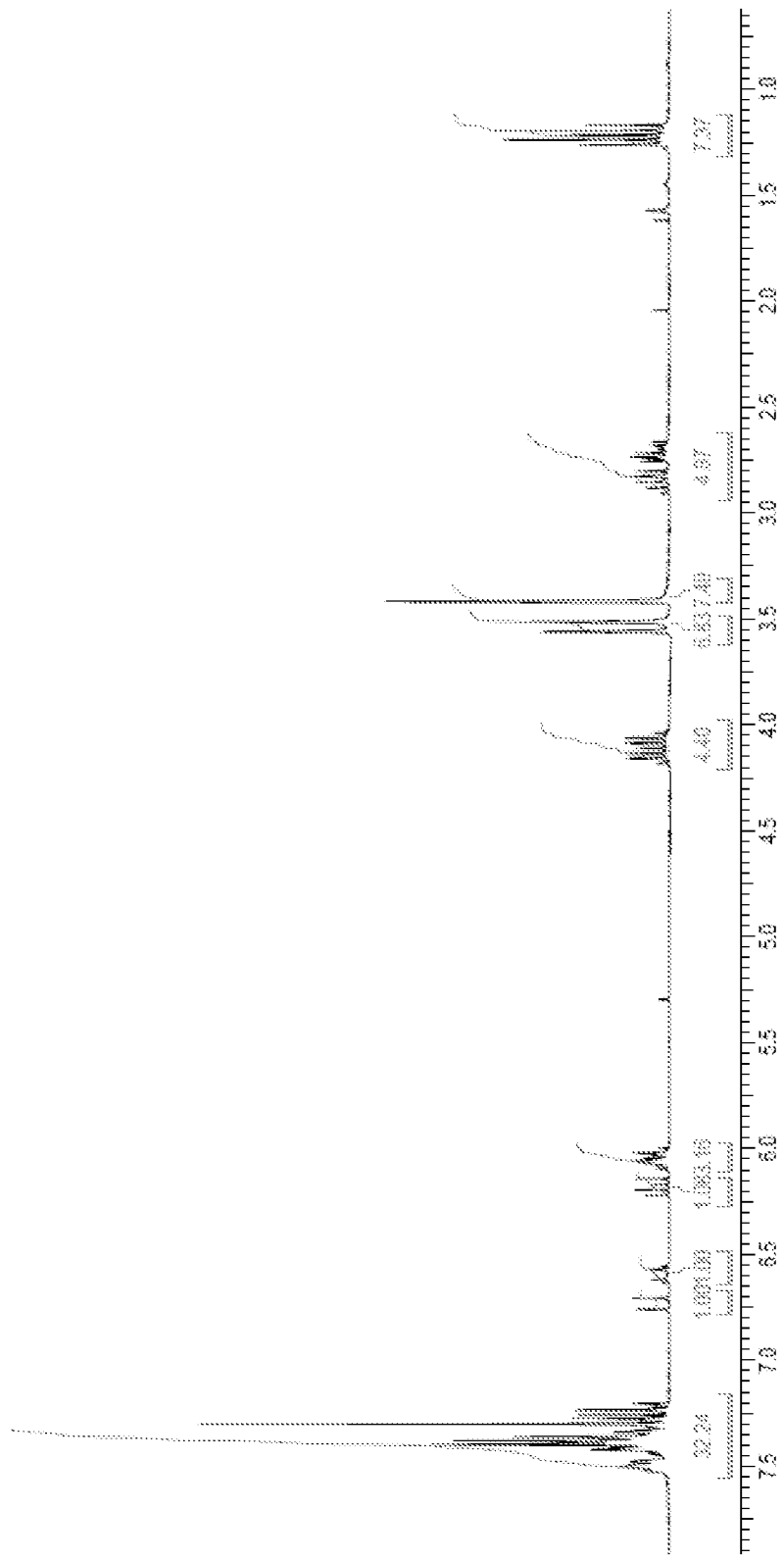
FIG. 7 shows a $^1$H NMR spectrum of a Mosher ester made from racemic β-hydroxyl ethyl ester (5C). Both diastereomers are observed in equal amounts.
Figure 8:
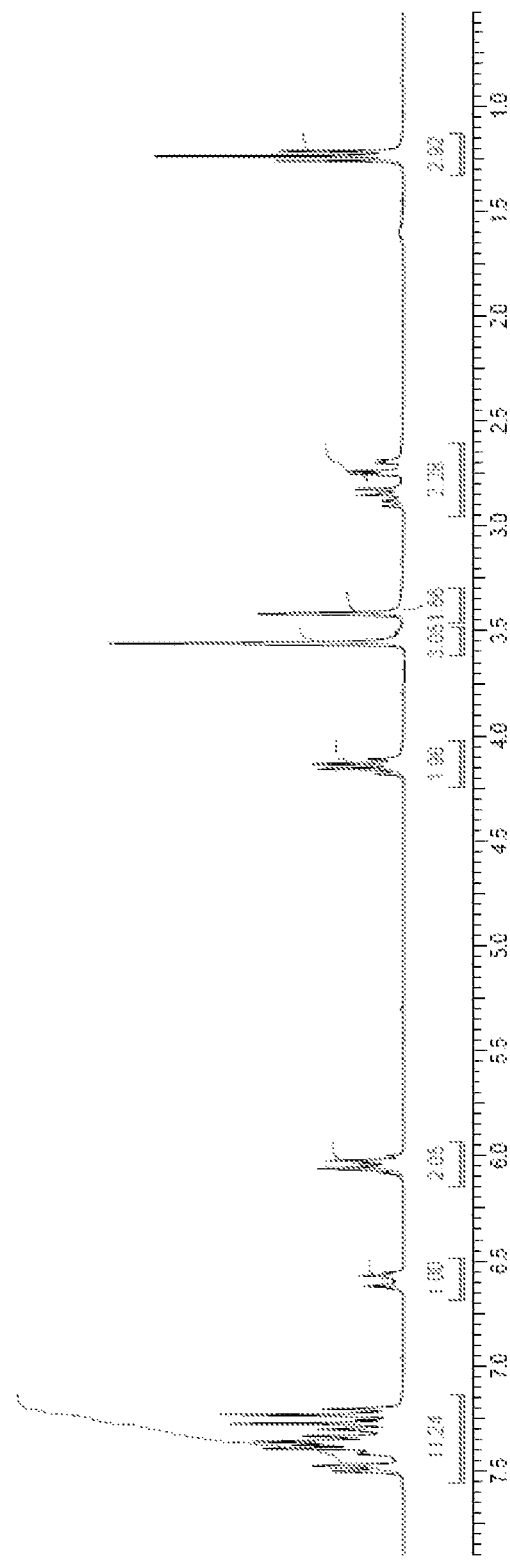
FIG. 8 shows a $^1$H NMR spectrum of a Mosher ester made from enantiopure β-hydroxyl ethyl ester (5C) prepared via enzymatic reduction using ketoreductase P1-B05. Only a single diastereomer is observed (R,S), indicating that the starting enantiomer (4C) was pure and that the absolute configuration of (4C) is R.
Figure 9:
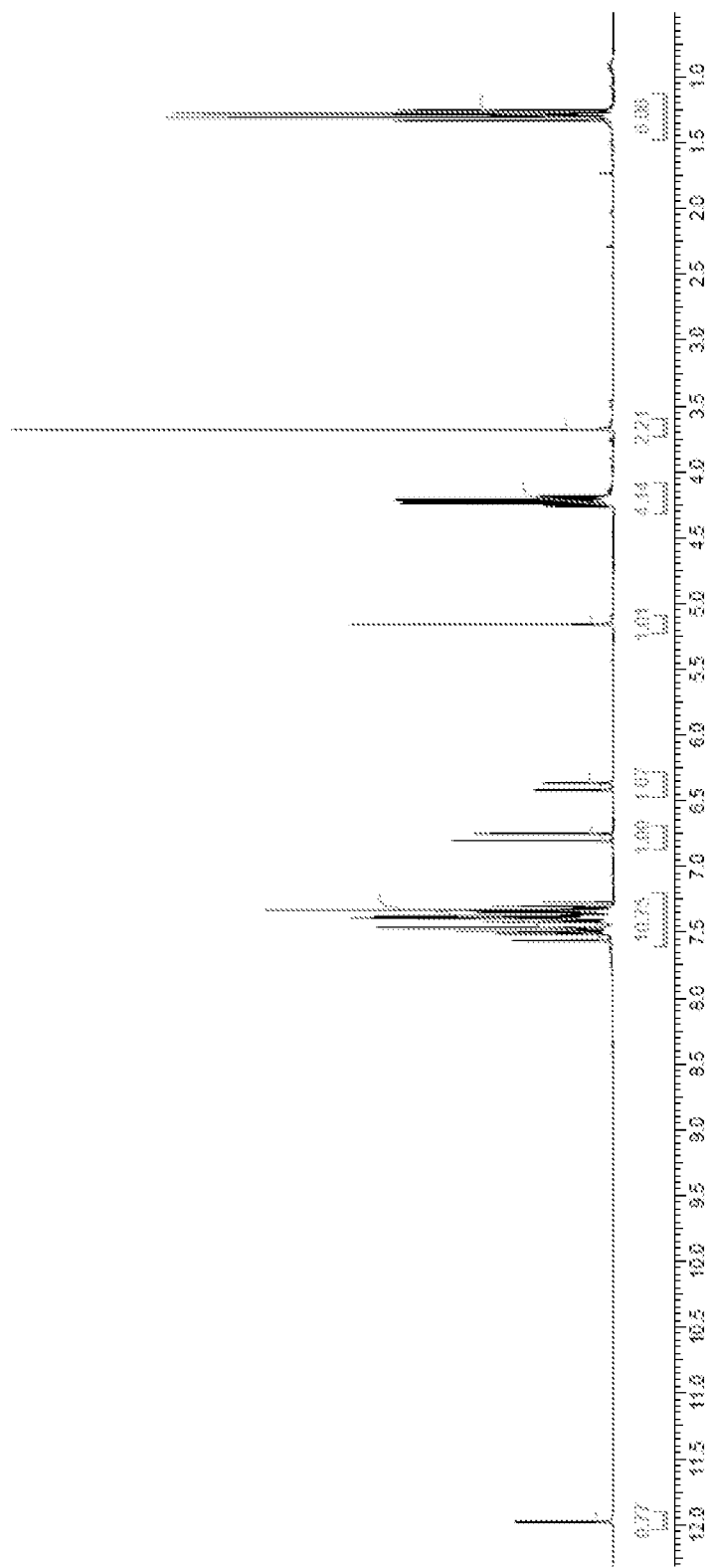
FIG. 9 shows the $^1$H NMR spectrum of γ,δ-unsaturated β-keto ethyl ester 4C.
Figure 10:
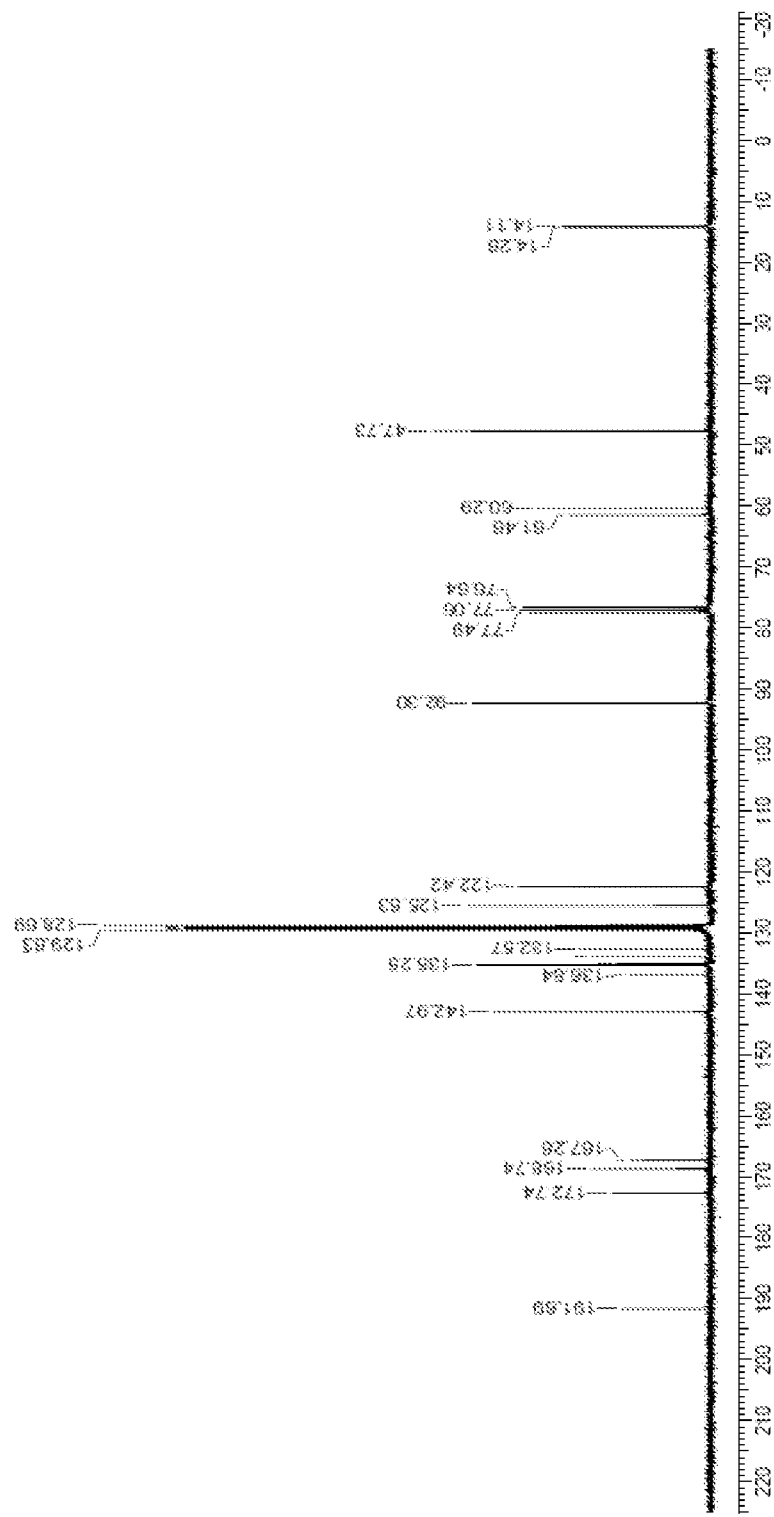
FIG. 10 shows the $^{13}$C NMR spectrum of γ,δ-unsaturated β-keto ethyl ester 4C.
Figure 11:
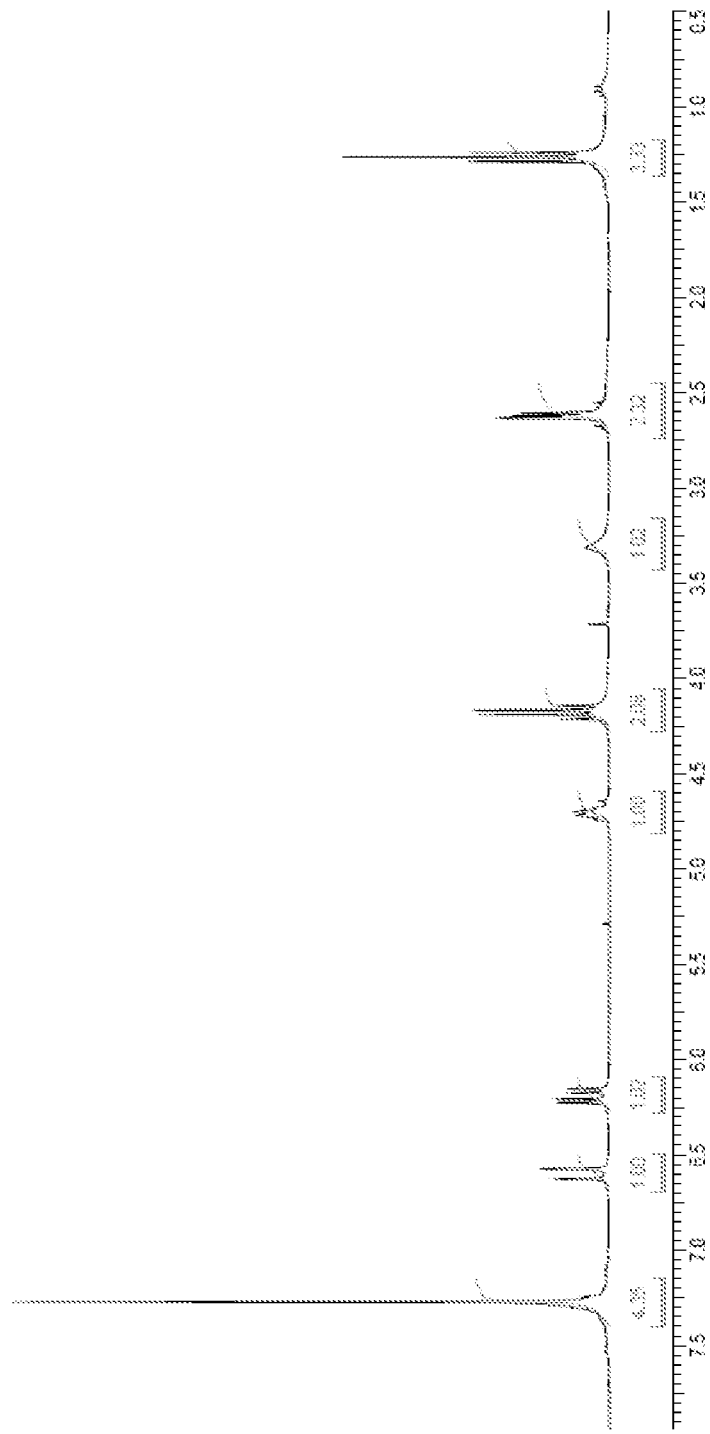
FIG. 11 shows the $^{1}$H NMR spectrum of γ,δ-unsaturated β-hydroxyester 5C.
Figure 12:
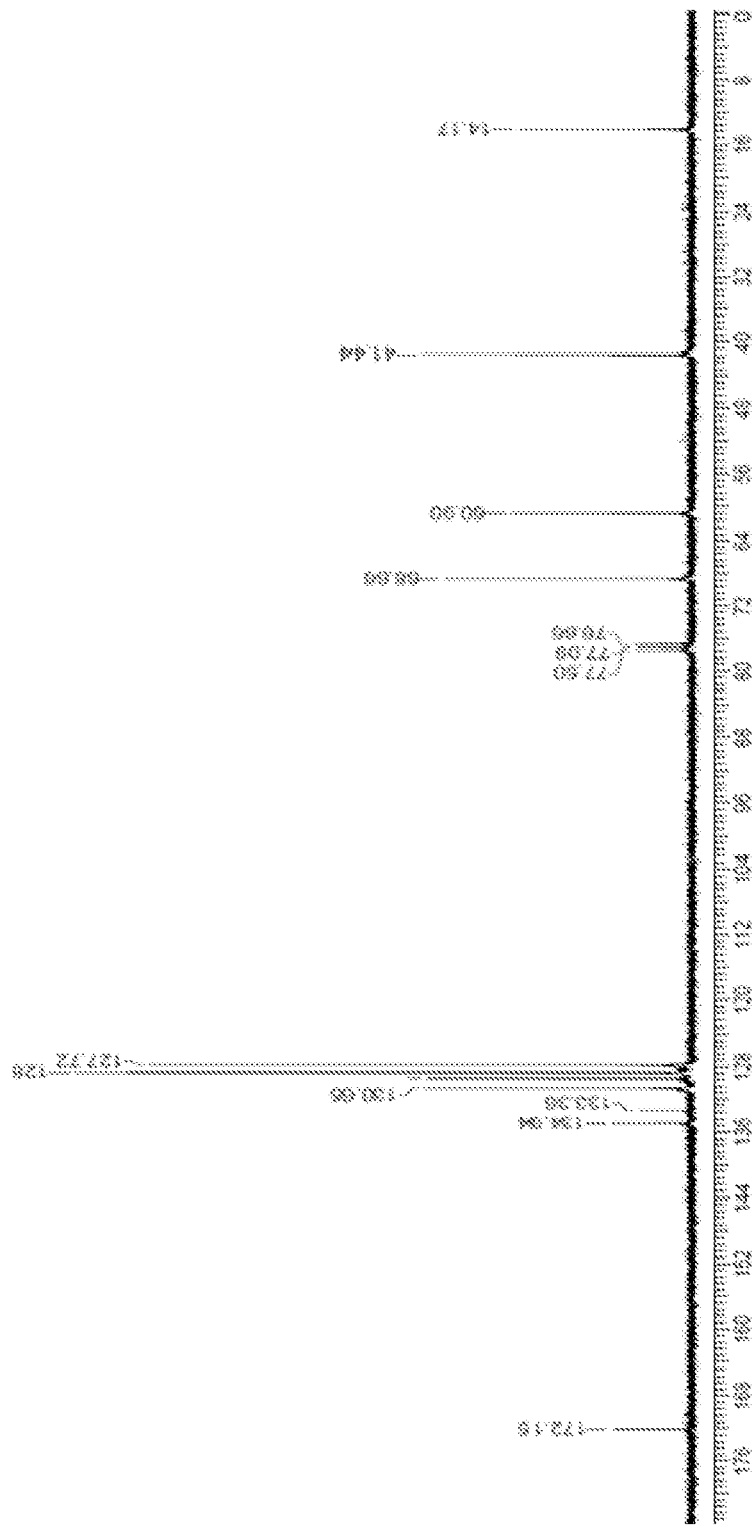
FIG. 12 shows the $^{13}$C NMR spectrum of γ,δ-unsaturated β-hydroxyester 5C.
Figure 13:
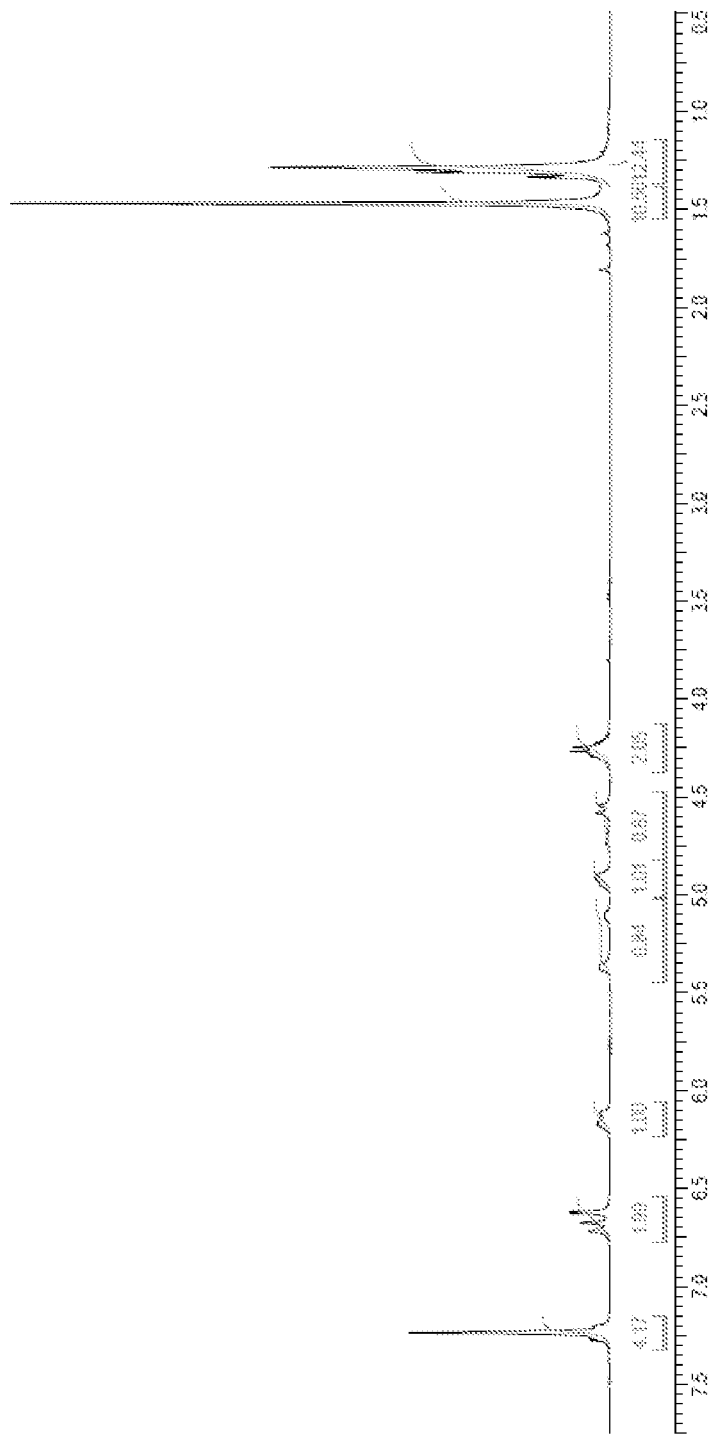
FIG. 13 shows the $^{1}$H NMR spectrum of hydrazine 6C.
Figure 14:
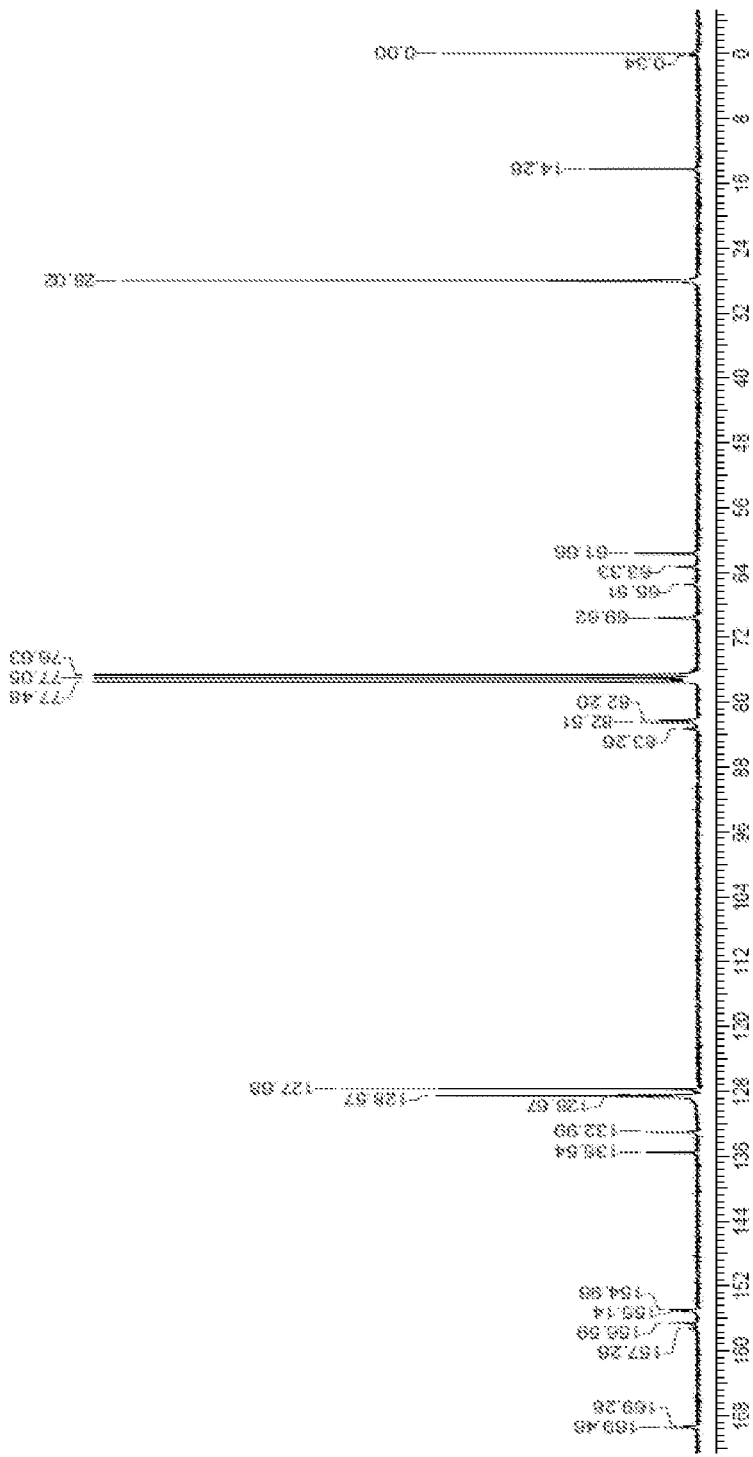
FIG. 14 shows the $^{13}$C NMR spectrum of hydrazine 6C.
Figure 15:
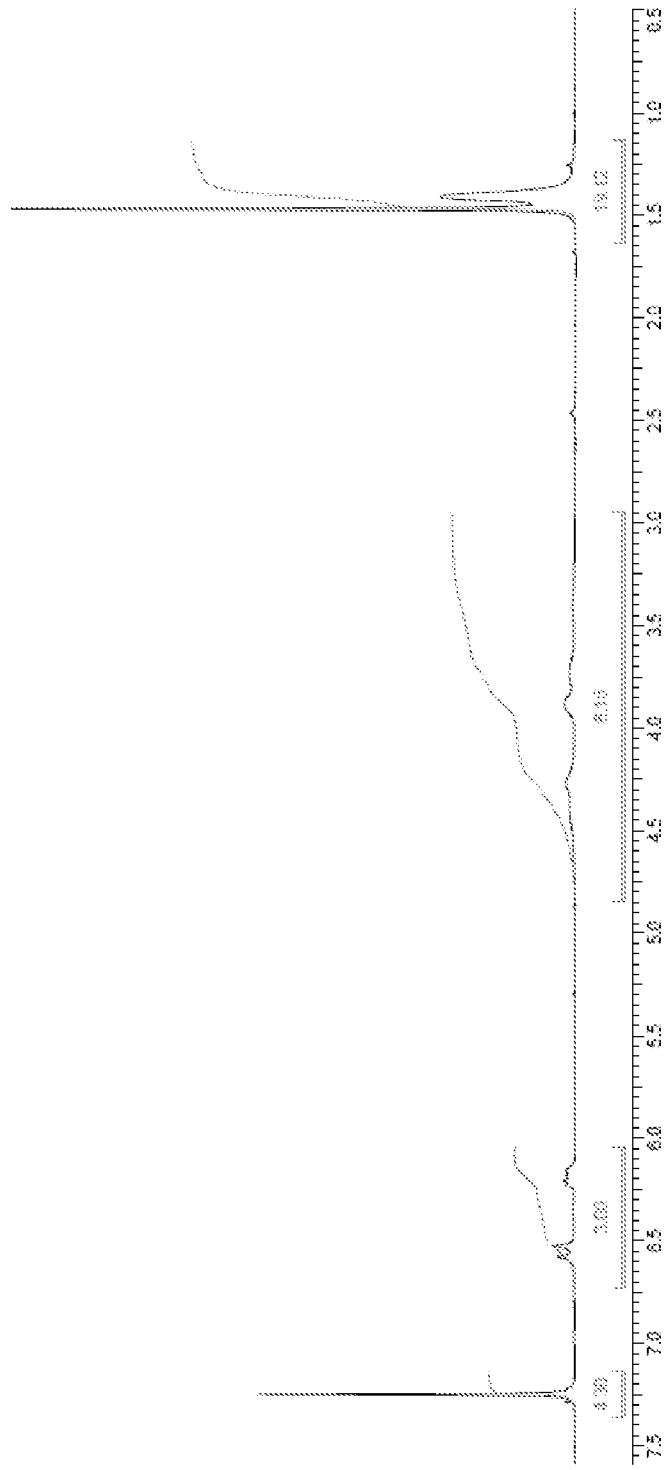
FIG. 15 shows the $^{1}$H NMR spectrum of diol 7C.
Figure 16:
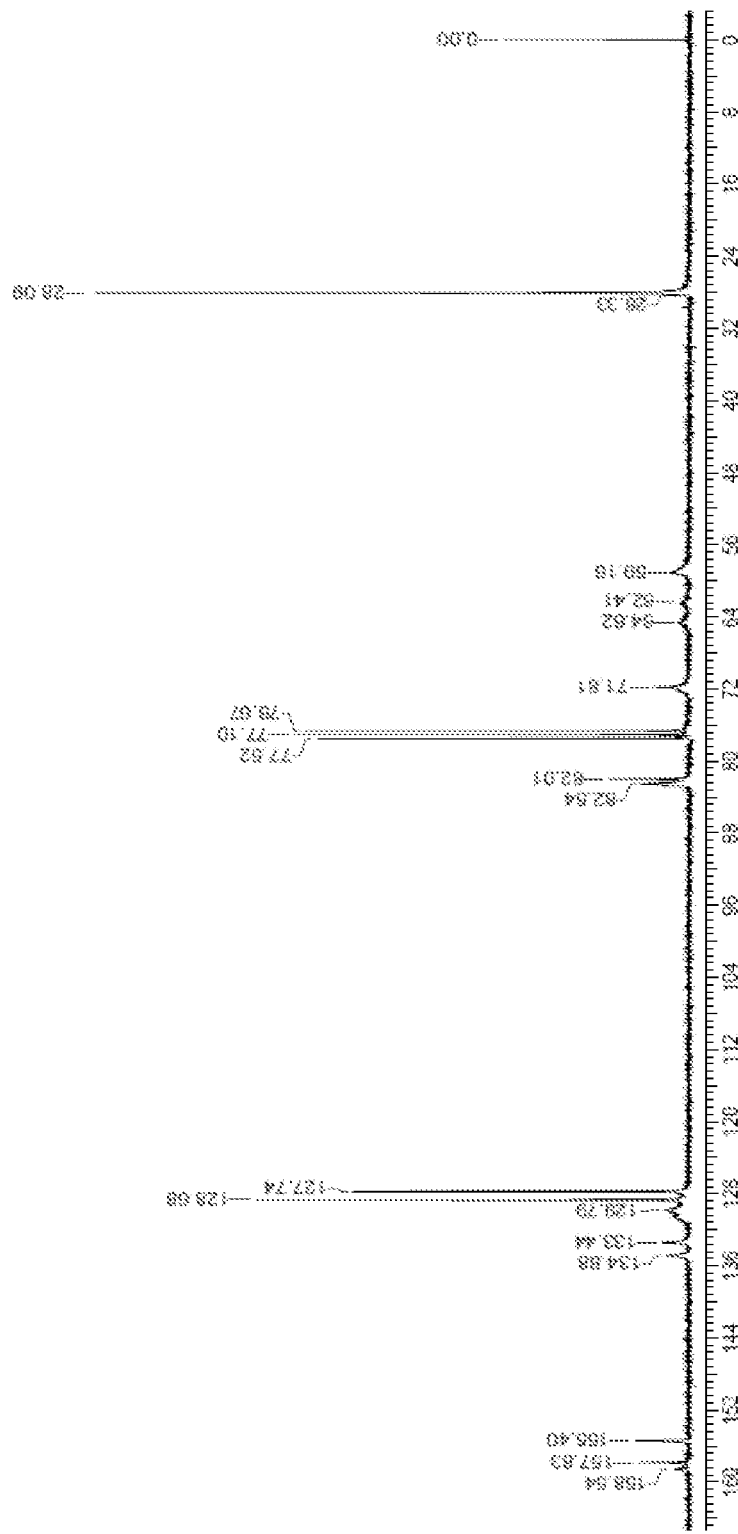
FIG. 16 shows the $^{13}$C NMR spectrum of diol 7C.
Figure 17:
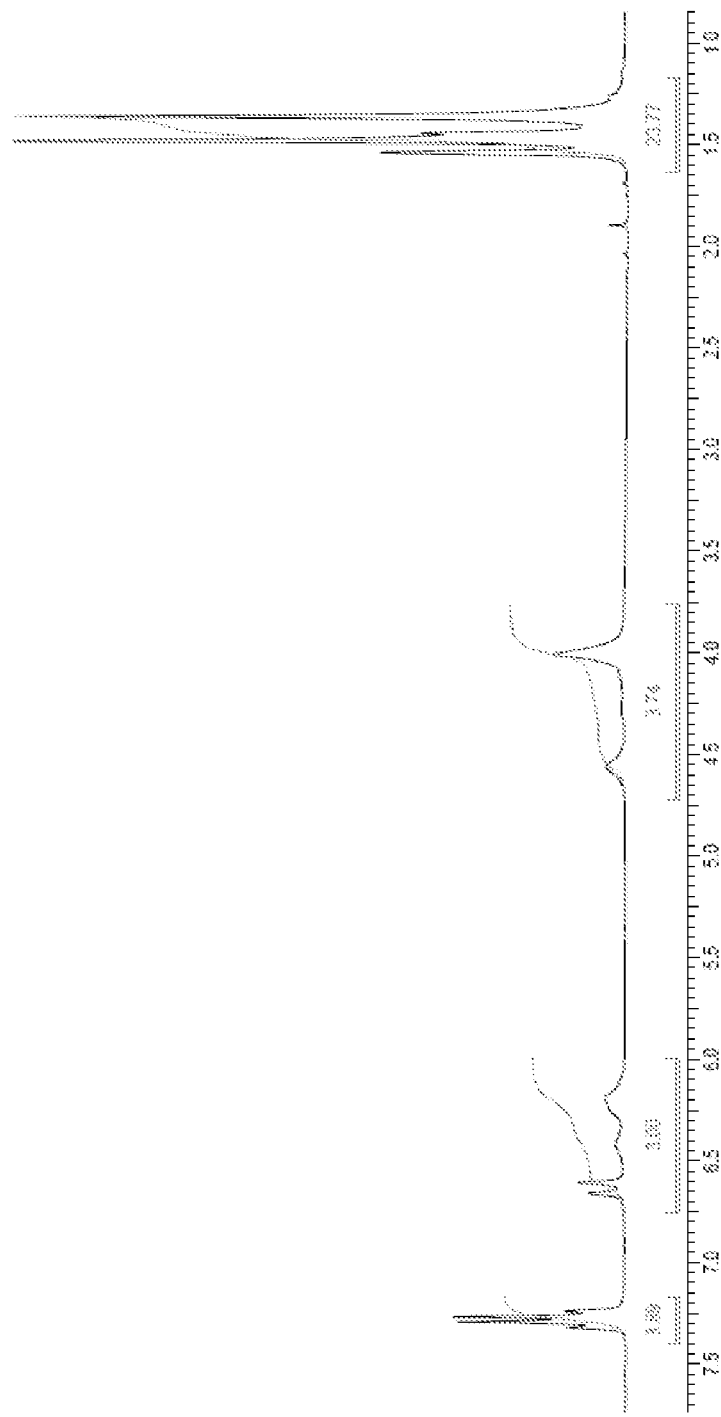
FIG. 17 shows the $^{1}$H NMR spectrum of acetal 8C.
Figure 18:
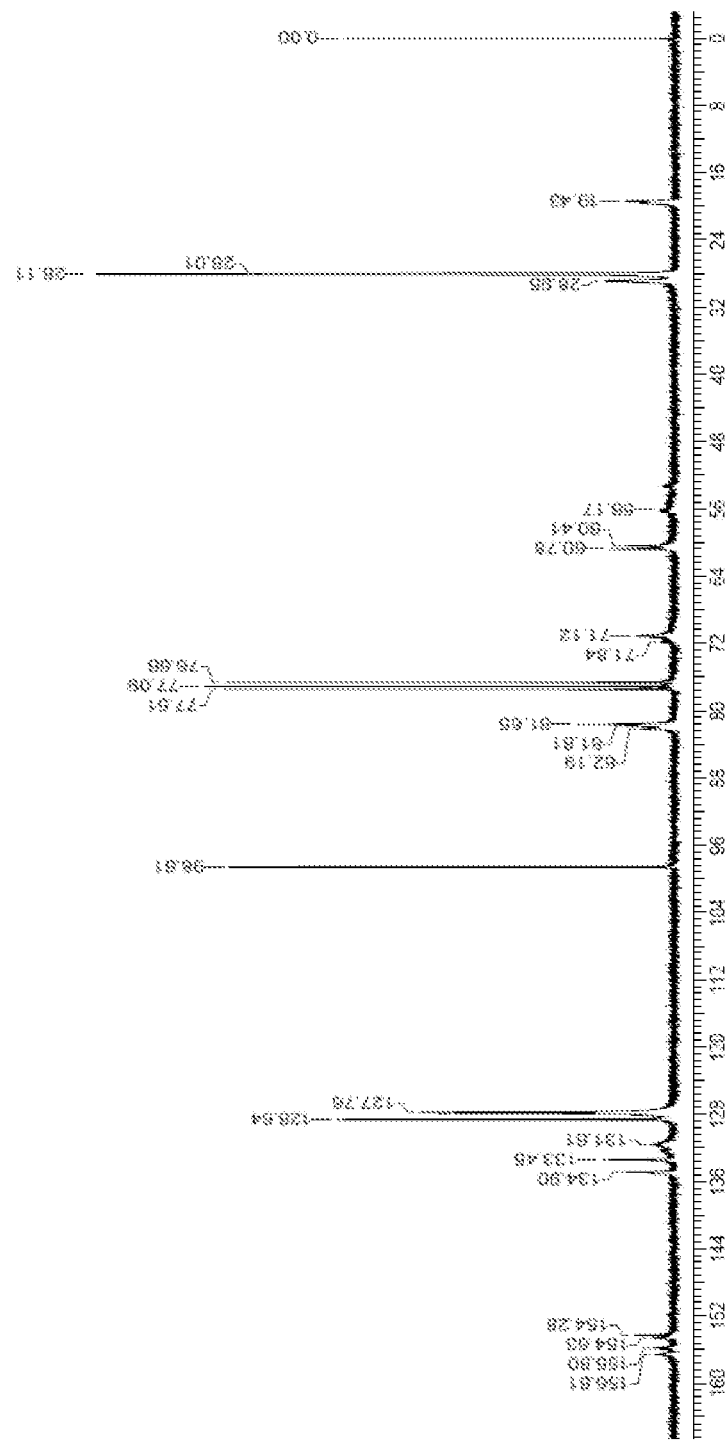
FIG. 18 shows the $^{13}$C NMR spectrum of acetal 8C.
Figure 19:
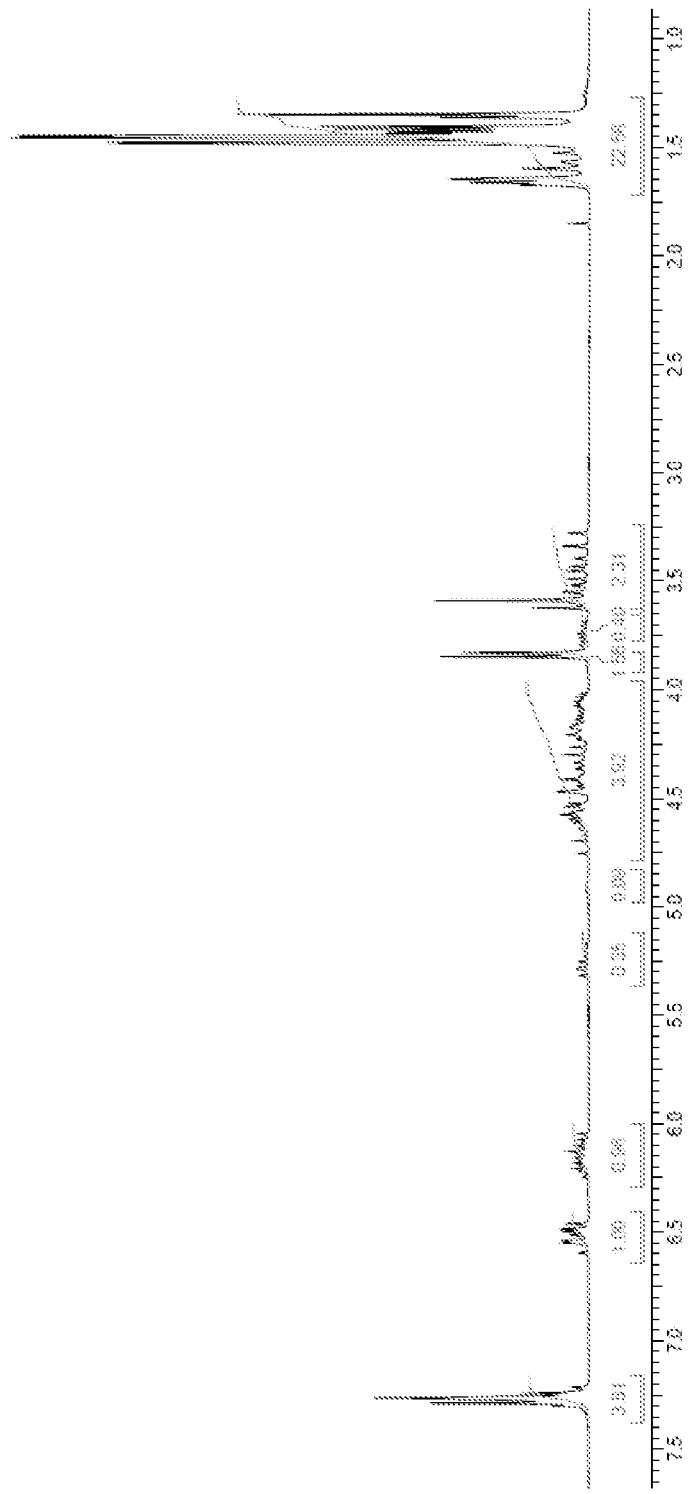
FIG. 19 shows the $^{1}$H NMR spectrum of ester 9C.
Figure 20:
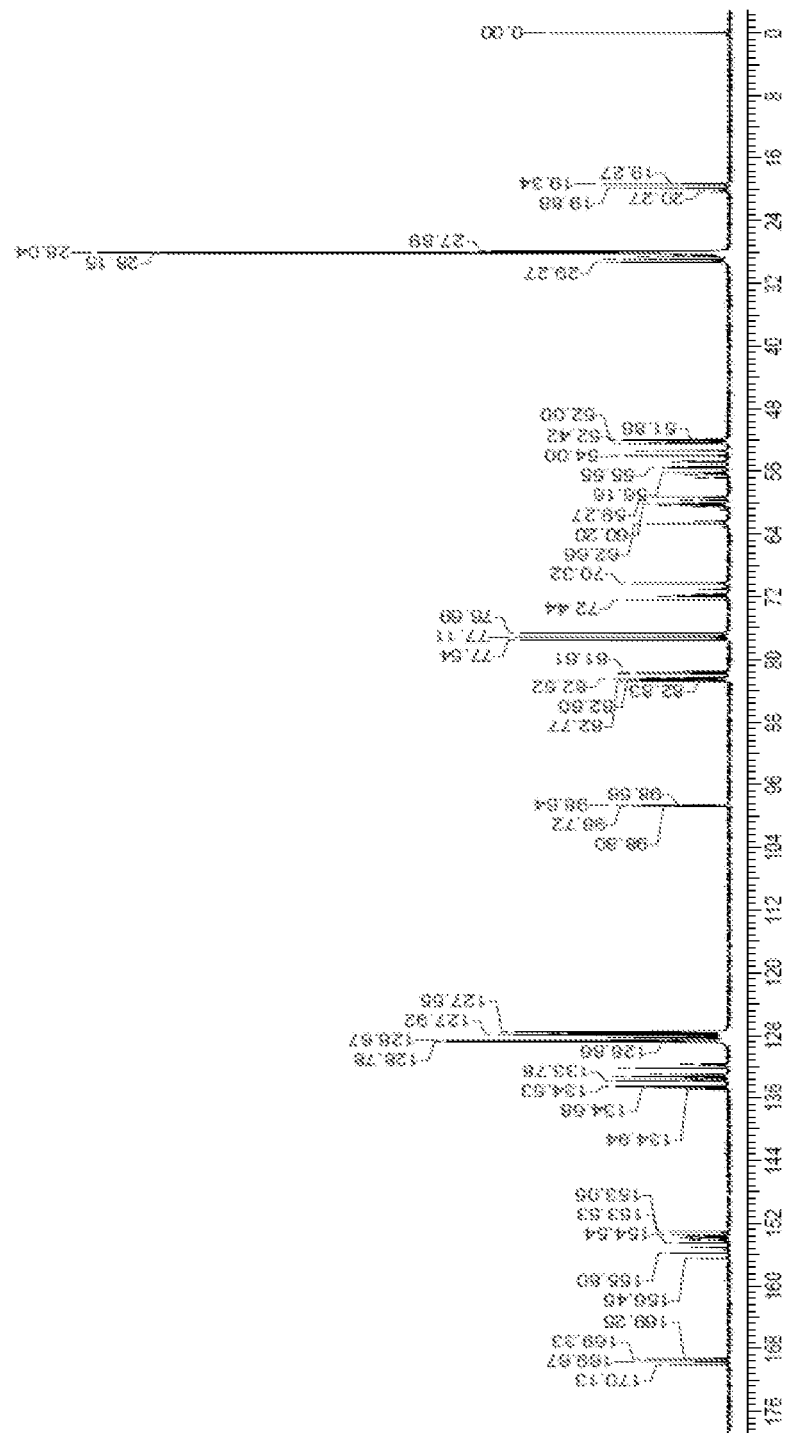
FIG. 20 shows the $^{13}$C NMR spectrum of ester 9C.
Figure 21:
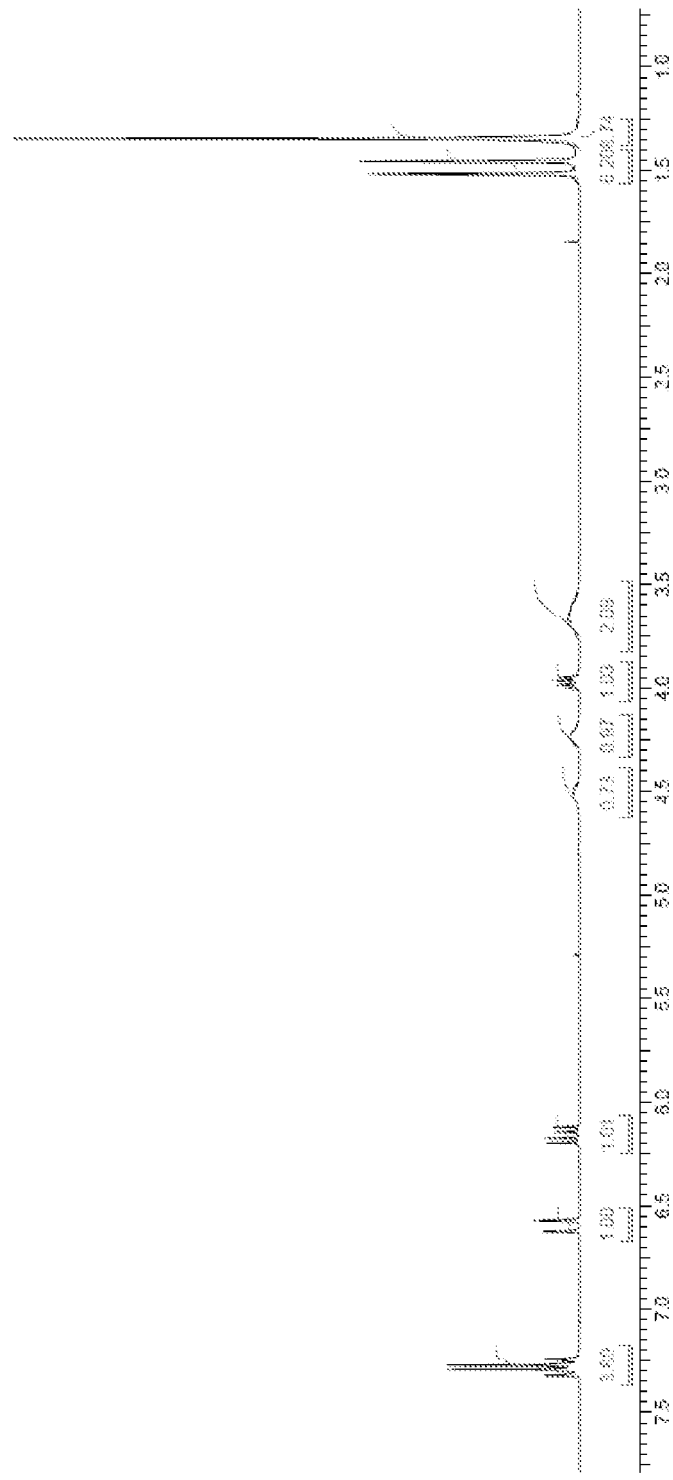
FIG. 21 shows the $^{1}$H NMR spectrum of carbamate 10C.
Figure 22:
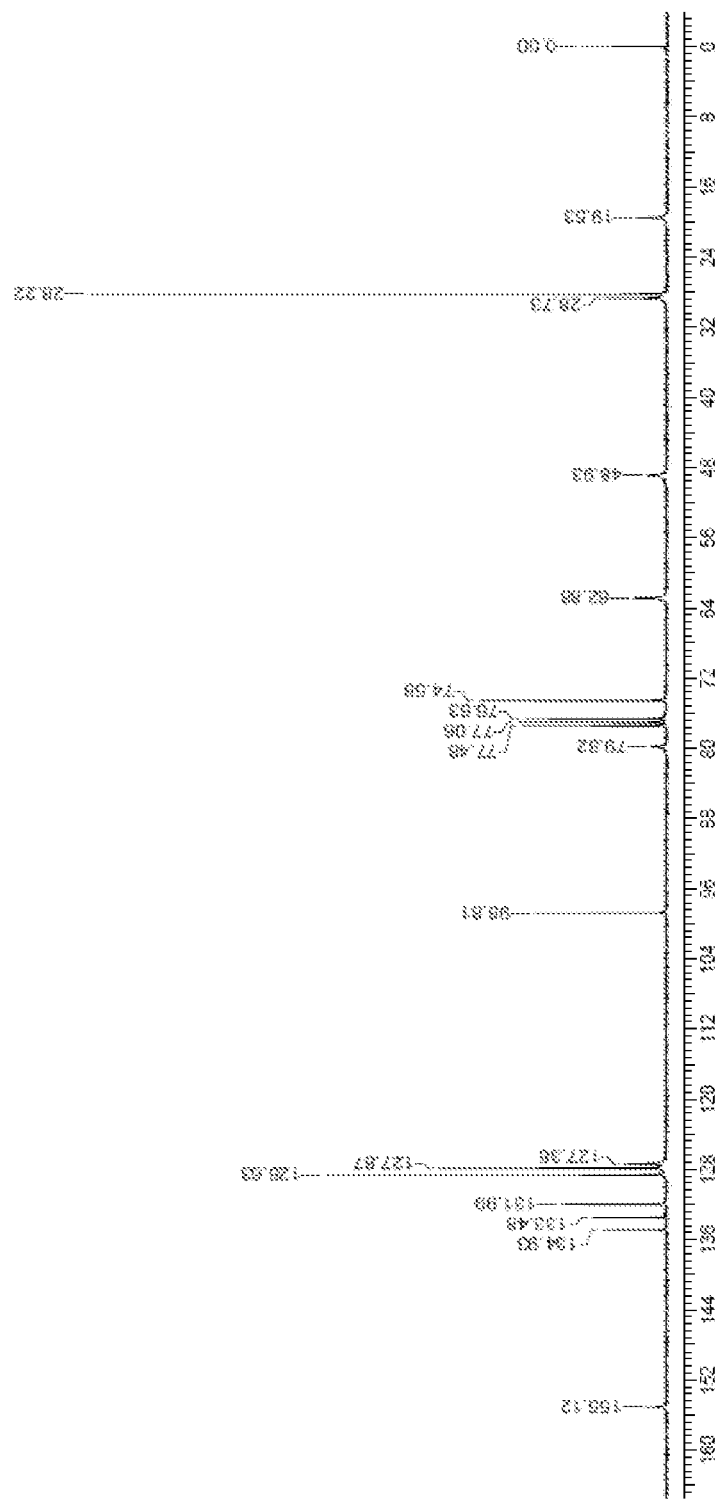
FIG. 22 shows the $^{13}$C NMR spectrum of carbamate 10C.
Figure 23:
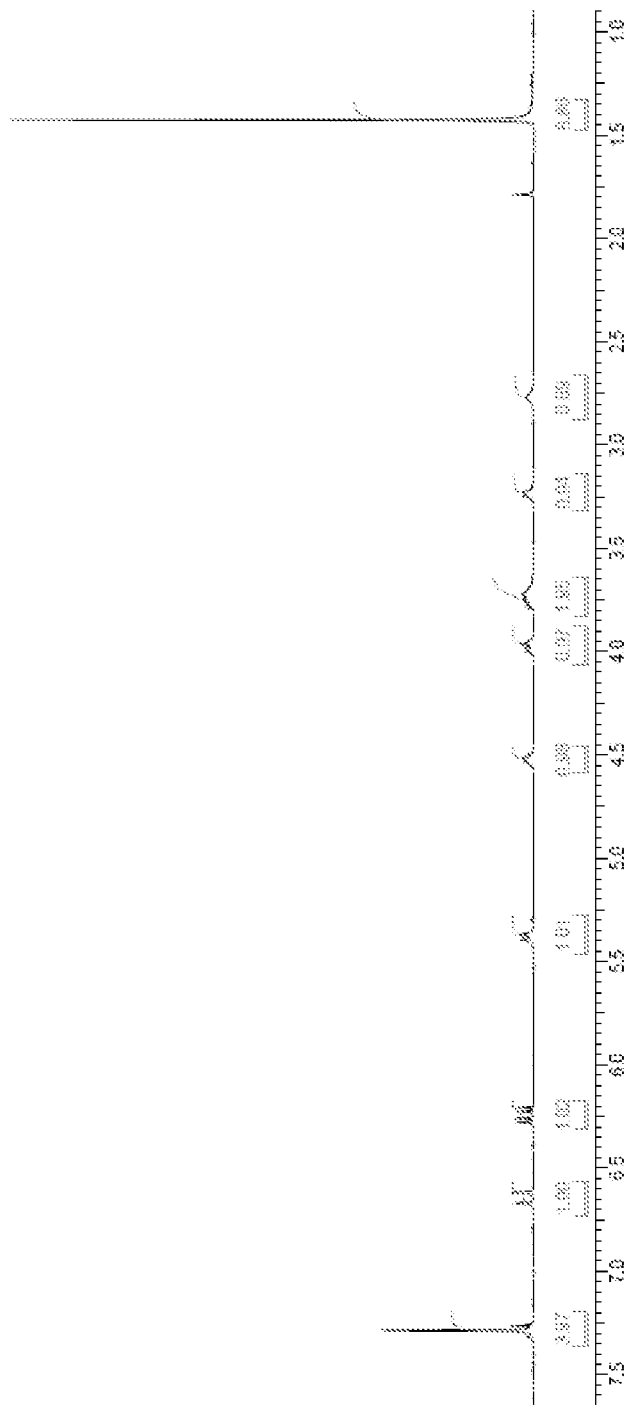
FIG. 23 shows the $^{1}$H NMR spectrum of sphingosine analog 11C.
Figure 24:
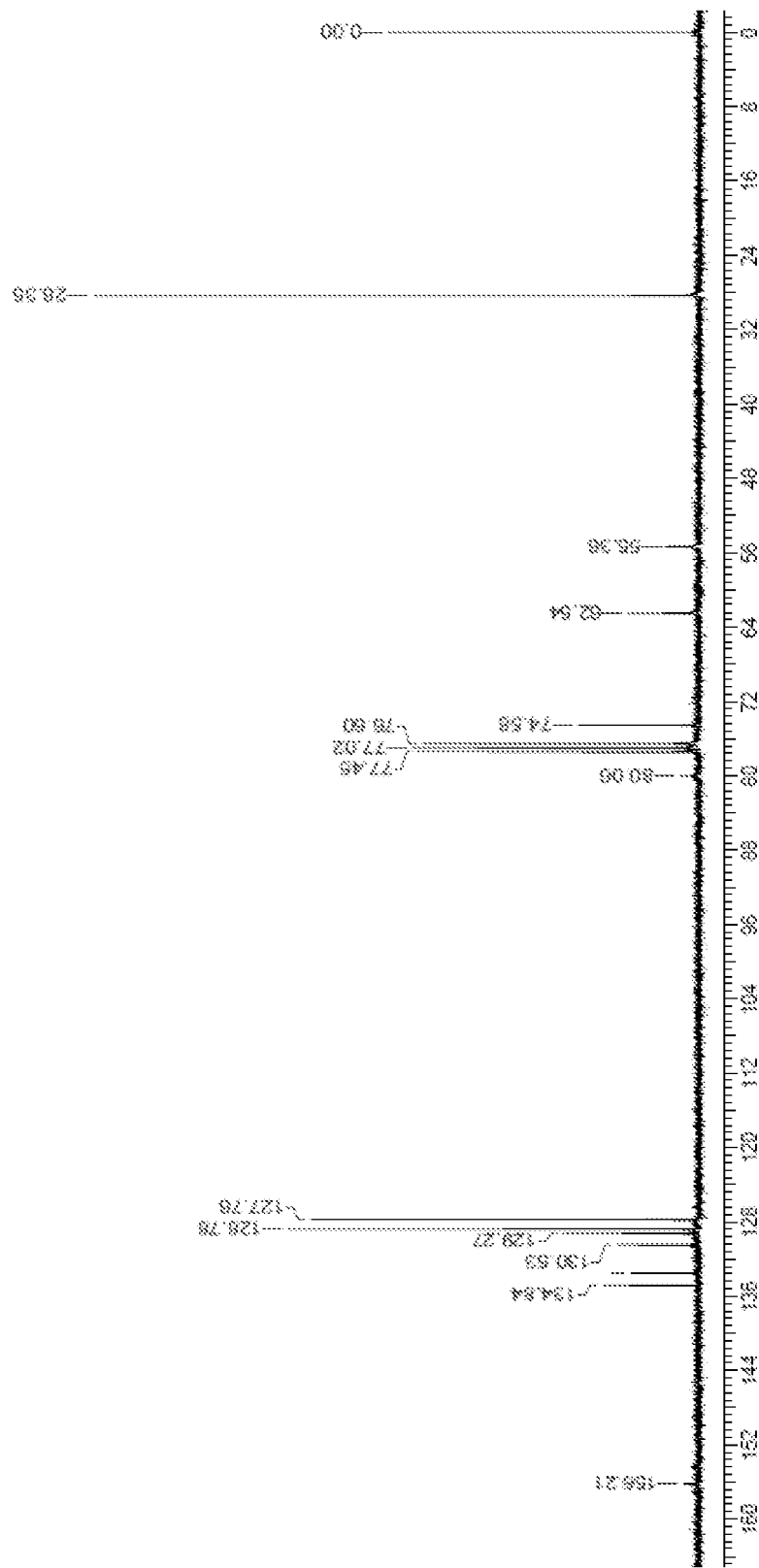
FIG. 24 shows the $^{13}$C NMR spectrum of sphingosine analog 11C.

To determine the absolute configuration of β-hydroxyesters, the reductions of β-ketoesters with enzyme 8 and 23, which provide >99% e.e. of (R) and (S) isomers, respectively, were scaled by a factor of 10 (0.25 mmol) by using the same relative ratio of enzyme to β-ketoesters as the microscale reaction. The Mosher ester method was then used to determine the absolute configuration of each enantiopure β-hydroxyester from enzyme 8 or 23 by comparison with the racemic mixture (FIGS. 7 and 8) (Hoye et al., *Nat. Protoc.* 2007, 2, 2451). Optical rotations of both enantiomers of aryl γ,δ-unsaturated β-hydroxyesters 5A, 5B, 5C, and 5E were measured (Table 3). Comparing the signs of measured values of 3A with those of known literature values, the absolute configurations of β-hydroxyesters were further confirmed (Carreira et al., *J. Am. Chem. Soc.* 1994, 116 8837; Padhi and Chadha, *Tetrahedron: Asymmetry* 2005, 16, 2790). The percent enantiomeric excess (% e.e.) was determined by either chiral HPLC or chiral capillary electrophoresis using a charged cyclodextrin as chiral selector (FIGS. 4-6).

TABLE 3

| Cmpd No. | Substance | KRED | Isolated Yield (%) | e.e.$^a$ (%) | $[\alpha]^{23}_{589}$ |
|---|---|---|---|---|---|
| 5A | Ph-CH=CH-CH(OH)-CH$_2$-C(O)OEt, (R) | P2-B02 | 90 | >99 | +14° (c 0.57, CHCl$_3$) lit. +13.6° (Carreira, 1994) |
| | Ph-CH=CH-CH(OH)-CH$_2$-C(O)OEt, (S) | 130 | 70 | −>99 | −16° (c 0.34, CHCl$_3$) lit. −2.6° (Padhi, 2005), −6.8° (Saravanan, 2012) |
| 5B | 4-Me-C$_6$H$_4$-CH=CH-CH(OH)-CH$_2$-C(O)OEt, (R) | P1-B05 | 79 | >99 | +20° (c 0.10, CHCl$_3$) |
| | 4-Me-C$_6$H$_4$-CH=CH-CH(OH)-CH$_2$-C(O)OEt, (S) | 130 | 75 | −>99 | −15° (c 0.33, CHCl$_3$) |
| 5C | 4-Cl-C$_6$H$_4$-CH=CH-CH(OH)-CH$_2$-C(O)OEt, (R) | P2-C11 | 81 | >99 | +15° (c 0.13, CHCl$_3$) |
| | 4-Cl-C$_6$H$_4$-CH=CH-CH(OH)-CH$_2$-C(O)OEt, (S) | P3-G09 | 81 | −>99 | −16° (c 0.16, CHCl$_3$) |
| 5E | 4-nBu-C$_6$H$_4$-CH=CH-CH(OH)-CH$_2$-C(O)OEt, (R) | P1-B05 | 77 | >99 | +20° (c 0.10, CHCl$_3$) |

TABLE 3-continued

| Cmpd No. | Substance | KRED | Isolated Yield (%) | e.e.[a] (%) | $[\alpha]^{23}_{589}$ |
|---|---|---|---|---|---|
| | nBu–C₆H₄–CH=CH–CH(OH)–CH₂–C(O)OEt | 130 | 64 | ->99 | -11° (c 0.55, CHCl₃) |

[a] Percent e.e. was measured by chiral HPLC.

For β-ketoesters 4A, 4B, 4C, and 4E, the reactions were scaled up by a factor of 20 or 100 using chosen ketoreductases, as shown in Table 3. The product γ,δ-unsaturated β-hydroxyesters 3 were isolated by chromatography on silica gel using 10:1 CH₂Cl₂/EtOAc. Isolated yields were slightly lower compared to NMR yields in Table 2. The same optical purity was obtained in all scaled reactions, compared to the one obtained from crude product as shown in Table 2.

Both (R) and (S) enantiomers of each γ-hydroxyester were produced impressively in optically pure form (>99% e.e.) by a number of KREDs. (S)-Enantiomer β-hydroxyesters were made from four enzymes (130, NADH-101, P3-G09 and P3-H12) while (R)-enantiomers can be accessed using nine enzymes (101, 119, P1-B02, P1-B05, P2-B02, P2-C02, P2-C11, P2-D11 and P2-G03). For each β-ketoester, at least one enzyme could be used to catalyze the formation of the corresponding (S)-enantiomer and several enzymes could be used to produce the corresponding (R)-enantiomer, both with excellent stereoselectivity and good conversion. For example, in the formation of (S)-5A, three out of four enzymes (NADH-101, P3-G09 and P3-H12) had low conversion with over 99% enantiomeric excess. However, enzyme 3 (130) could catalyze formation of (S)-5A with both excellent stereoselectivity (>99%) and conversion (84%). Seven out of nine enzymes catalyzed the formation of (R)-5A with over 99% e.e. and 83-99% conversion. Impressively, the ¹H NMR spectra of several crude products (e.g. those from enzyme 8) showed no impurities, and were essentially identical to the spectrum of the "purified" product.

d. Absolute Configuration of β-Hydroxyesters(5F and 5F')

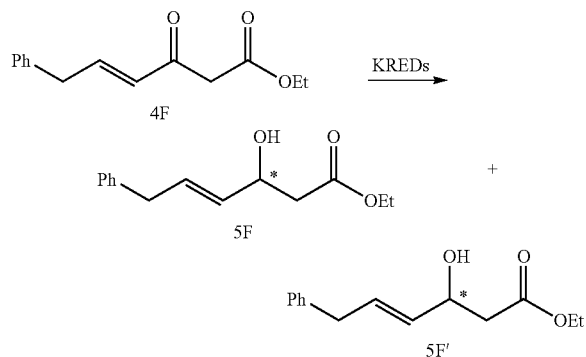

Figures 25A, 25B:
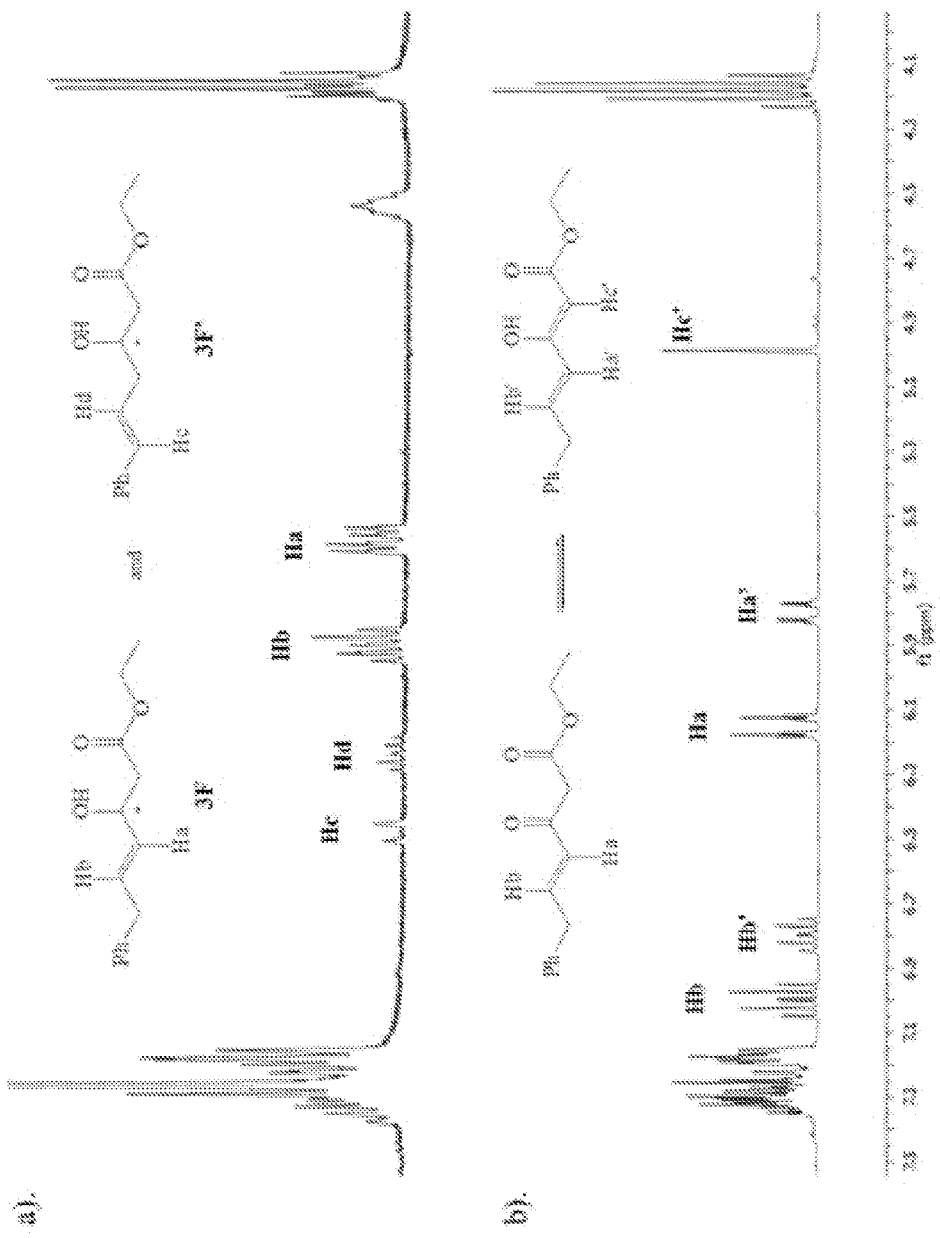
FIGS. 25 A and B show $^{1}$H NMR spectrum of olefinic and methylene hydrogens in 3F and 3F'. 25A): purified enzymatic products 3F and 3F' from β-ketoester 2F reduced by enzyme 23 (KRED-P3-G09). $^{1}$H NMR of olefinic protons in 3F and 3F' made from enezyme 23 (KRED-P3-G09) are displayed. Hc (d, J=15 Hz) and Hd (dt, J=9, 15 Hz) resonance at 6.48 and 6.25 ppm were assigned as olefinic protons of 3F' while Ha (d, J=15 Hz) and Hb (dt, J=9, 15 Hz) resonance at 5.57 and 5.90 ppm belong to olefinic protons of 3F, which confirmed the allylic rearrangement. 25B: β-ketoester 2F in keto-enol form.
Figure 26:
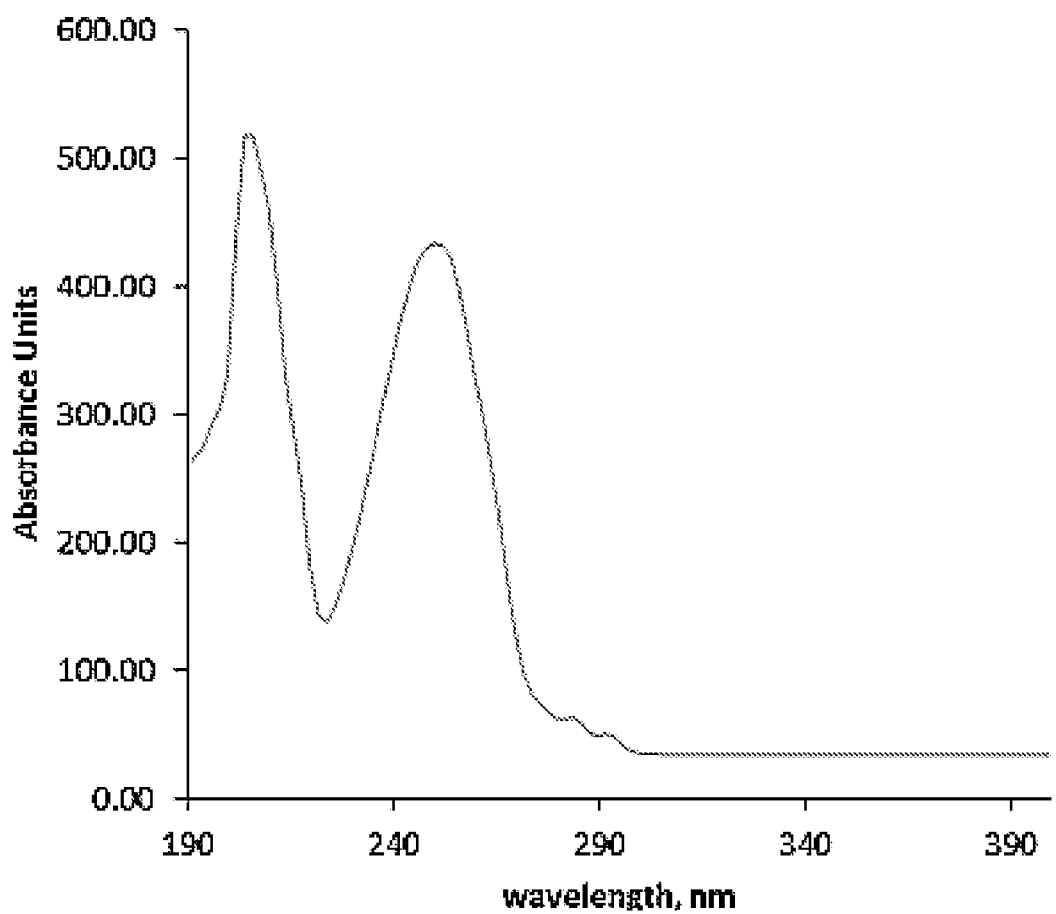
FIG. 26 shows ultraviolet absorption spectrum of ethyl (5E)-3-hydroxy-6-phenylhex-5-enoate 3F'.
Figure 27:
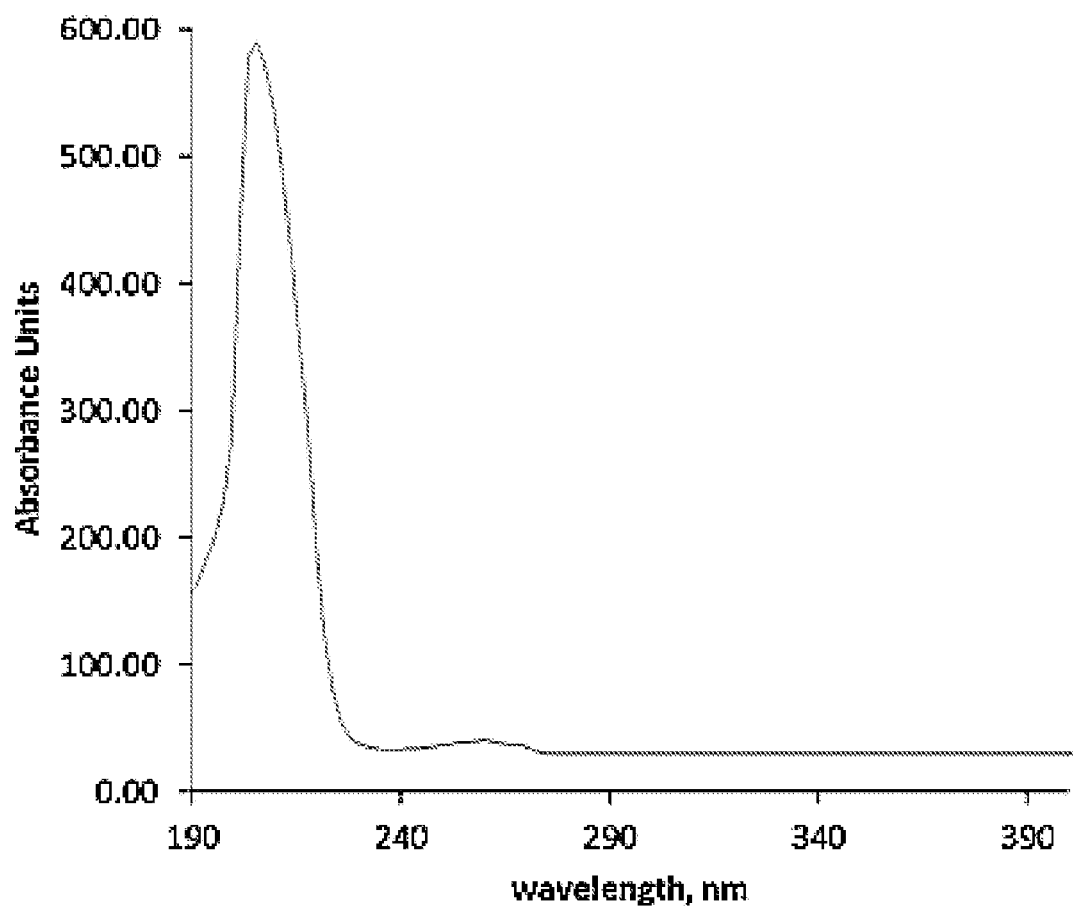
FIG. 27 shows ultraviolet absorption spectrum of ethyl (4E)-3-hydroxy-6-phenylhex-4-enoate 3F.

In the case of β-ketoester 4F, 1,3-hydrogen rearrangement occurred to a small extent when some ketoreductases were used, which produced not only ethyl (4E)-3-hydroxy-6-phenylhex-4-enoate 5F, but also ethyl (5E)-3-hydroxy-6-phenylhex-5-enoate 5F', as shown above. In the rearrangement process, the hydrogen was transferred without formation of the Z-isomer. Evidence of 1,3-hydrogen rearrangement comes from the HPLC ultraviolet absorption spectra of 5F and 5F' which show different absorption maxima ($\lambda_{max}$) for 5F and 5F'. Indeed, a $\lambda_{max}$ at 250 nm is observed in the UV spectrum of 3F' while a $\lambda_{max}$ of 206 nm is the spectrum of 5F (see FIGS. 26 and 27). Further conclusive evidence for allylic rearrangement was obtained by examination of the ¹H NMR spectra of the crude products (See FIG. 25).

The pathway for the formation of 5F' is not clear. Double bond migration of 4F may occur prior to enzymatic reduction to 5F'. Alternatively, 4F may be enzymatically reduced to 5F, followed by isomerization to 5F'. Current literature is lacking on the mechanistic aspects of this process and further studies will be required. Nevertheless, product (R)-5F can be obtained in pure form with high e.e. and conversion (Enzymes 5 and 20) but further optimization is required for obtaining pure (5)-5F with high yield and conversion.

e. Diastereoselective Amination

The diastereospecific formation of anti N-boc-α-hydrazino-β-hydroxyesters (6A-6F) was performed via electrophilic amination of the β-hydroxyesters (5A-5F) with di-tert-butylazodicarboxylate (DBAD) (Girard, A.; et al. *Tetrahedron Letters* 1996, 37, 7967-7970; Labeeuw, O. *Tetrahedron Letters* 2003, 44, 6383-6386; Greck, C. et al., *Synlett* 1993, 475-477.

42. Greck, C.; Genet, J. P., Electrophilic amination: New synthetic applications. *Synlett* 1997, 741) In order to obtain high diastereoisomeric excesses, the zinc enolate form of β-hydroxyesters (5A-5F) was required. This was achieved by adding one equivalent of MeZnBr at 0° C. for 1 h followed by two equivalents of LDA at -78° C. for another 1 h into β-hydroxyesters (5A-5F). Electrophilic amination was achieved via Michael reaction, after addition of DBAD at -78° C. for another 2 h. The product was isolated by normal phase chromatography with a yield of 50-60%. Unreacted β-hydroxyesters (5A-5F) could be recovered without racemization. Due to the rigid zinc enolate form of β-hydroxyesters (5A-5F), the anti-configurational relationship between the hydroxyl and hydrazino functionalities was obtained with excellent diastereoisomeric excesses (>99%) and no syn-diastereoisomer was detected, as indicated by ¹H NMR. The configurations, diastereoisomeric excesses and isolated yields of N-boc-α-hydrazino-β-hydroxyesters (6A-6D) are listed in Table 4.

TABLE 4

| Cmpd. No. | Substance | Configuration[a] | d.e.[b] (%) | Isolated Yield (%) |
|---|---|---|---|---|
| 6A | ethyl (S,S)-2-(NBoc,BocHN-hydrazino)-3-hydroxy-5-phenylpent-4-enoate | (S,S) | >99 | 58 |
|  | ethyl (R,R)-2-(NBoc,BocHN-hydrazino)-3-hydroxy-5-phenylpent-4-enoate | (R,R) | >99 | 58 |
| 6B | ethyl (S,S)-2-(NBoc,BocHN-hydrazino)-3-hydroxy-5-(4-methylphenyl)pent-4-enoate | (S,S) | >99 | 50 |
|  | ethyl (R,R)-2-(NBoc,BocHN-hydrazino)-3-hydroxy-5-(4-methylphenyl)pent-4-enoate | (R,R) | >99 | 60 |
| 6C | ethyl 2-(NBoc,BocHN-hydrazino)-3-hydroxy-5-(4-chlorophenyl)pent-4-enoate | racemic, anti | >99 | 58 |
| 6D | ethyl 2-(NBoc,BocHN-hydrazino)-3-hydroxy-5-(4-nitrophenyl)pent-4-enoate | racemic, anti | >99 | 55 |

[a]Assignment of configuration refers to the configuration of the α and β position;
[b]The percent d.e. was measured by both $^1$H NMR and chiral HPLC.

3. Characterization of Exemplary Intermediates

The configurations, diastereoisomeric excesses and isolated yields of all intermediates are listed in Table 5.

TABLE 5

| Cmpd. |  | 5 | 6 | 7 | 8 | 9 | 10 |
|---|---|---|---|---|---|---|---|
|  | Structure | 3-hydroxy ester (OH, OEt) | 2-hydrazino-3-hydroxy ester (OH, OEt, BocHN-NBoc) | 2-hydrazino-1,3-diol (OH, OH, BocHN-NBoc) | acetonide with BocHN-NBoc | acetonide with BocN(CH$_2$CO$_2$CH$_3$)-NBoc | acetonide with NHBoc |
| A | Configuration[a] | R | S,S | S,R | S,R | S,R | S,R |
|  | e.e. or d.e.[b] (%) | >99 | >99 | >99 | >99 | >99 | >99 |
|  | Isolated Yield (%) | — | 58 | 85 | 94 | 99 | 85 |

TABLE 5-continued

| Cmpd. | | 5 | 6 | 7 | 8 | 9 | 10 |
|---|---|---|---|---|---|---|---|
| B | Configuration[a] | R | S,S | S,R | S,R | S,R | S,R |
|   | e.e. or d.e.[b] (%) | >99 | >99 | >99 | >99 | >99 | >99 |
|   | Isolated Yield (%) | — | 50 | 80 | 94 | 94 | 95 |
| A | Configuration[a] | S | R,R | R,S | R,S | — | R,S |
|   | e.e. or d.e.[b] (%) | 75 | >99 | >99 | >99 | — | >99 |
|   | Isolated Yield (%) | — | 58 | 88 | 93 | — | 94 |
| B | Configuration[a] | S | R,R | R,S | R,S | R,S | R,S |
|   | e.e. or d.e.[b] (%) | >99 | >99 | >99 | >99 | >99 | >99 |
|   | Isolated Yield (%) | — | 60 | 81 | 94 | 95 | 86 |
| C | Configuration[a] | Racemic | racemic, anti | racemic, anti | racemic, anti | racemic, anti | racemic, anti |
|   | e.e. or d.e.[b] (%) | — | >99 | >99 | >99 | >99 | >99 |
|   | Isolated Yield (%) | — | 55 | 83 | 94 | 98 | 97 |
| D | Configuration[a] | Racemic | racemic, anti | racemic, anti | racemic, anti | racemic, anti | racemic, anti |
|   | e.e. or d.e.[b] (%) | — | >99 | >99 | >99 | >99 | >99 |
|   | Isolated Yield (%) | — | 58 | 83 | 94 | 99 | 83 |

[a]Assignment of configuration refers to the configuration of the α and β position for N-boc-α-hydrazino-β-hydroxyesters 5 and to the configuration of carbon-2 and carbon-3 for compounds 6 to 9;
[b]The percent e.e. was measured by chiral HPLC and the percent d.e. was measured by both $^1$H NMR and chiral HPLC.

According to the literature, ketoesters can be effectively reduced to diols using NaBH$_4$ in MeOH at rt (Kim et al., *Tetrahedron* 2010, 66, 3995; Chaudhuri et al., *Beilstein journal of organic chemistry* 2010, 6, 748), while unsaturated esters were reported to be reduced mostly into saturated alcohol in the presence of 10 folds excess NaBH$_4$ (Brown and Rapoport, *JOC* 1963, 28, 3261). Reduction of compound 6A to 1,3-diol 7A using three equivalents of NaBH$_4$ in MeOH, however, resulted in low yield. To enhance the reduction of compounds (6A-6D) to 1,3-diols (7A-7D) and avoid hydrogenation of C—C double bonds induced by a large excess of NaBH$_4$, three equivalents of NaBH$_4$ was added to compounds (6A-6D) in methanol every 15 min until compounds (6A-6D) were completely consumed, as indicated by TLC (5:3/ CH$_2$Cl$_2$:EtOAc). The reaction was complete within 3-4 h at rt, with between 36-51 equivalents of NaBH$_4$ required. The excess NaBH$_4$ was quenched with saturated NH$_4$Cl solution. After simple chromatography on silica gel, a yield of 80-88% was obtained. One possible mechanism for the reduction of ketoesters involves the slow decomposition of NaBH$_4$ to generate trimethoxy borane, which may further serve as a Lewis acid to generate a cyclic intermediate. This, in turn, may activate and promote the reduction of the ester by sodium alkoxyborohydride species (Dai et al., *Molecular Catalysis B: Enzymatic*, In Press).

Compounds (7A-7D) were protected in the form of anti 2-di-tert-butoxycarbonyl hydrazino 1,3-diol ketals (8A-8D). Ketalization was conducted in anhydrous acetone with 10 mol % of p-toluenesulfonic acid at rt to give 1,3-diol ketals (8A-8D) in 93-94% yield.

The ElcB eliminative N—N bond cleavage protocol of Magnus et al. was utilized for the cleavage of hydrazino N—N bond (Magnus et al., *Org. Lett.* 2009, 11, 5646). Alkylation of the —NH— of anti 2-di-tert-butoxycarbonyl hydrazino 1,3-diol ketals (8A-8D) was achieved by reaction with 2.0 equiv. of methyl bromoacetate in anhydrous MeCN in the presence of 2.5 equiv. of $Cs_2CO_3$ at 50° C. After purification by column chromatography, the alkylated 1,3-diol ketals were refluxed with 3.0 equiv. of $Cs_2CO_3$ to give carbamates (10A-10D) with yields between 83-97%. Isolation of the alkylated 1,3 diol ketal is not necessary; for example, S-8B was reacted with 2.0 equiv. of methyl bromoacetate, followed by reflux with 4.0 equiv. of $Cs_2CO_3$ to give S-10B with 95% yield. Chiral HPLC was employed on all intermediates, demonstrating that stereochemical purity was preserved during the conversion of (5A-5D) to (10A-10D).

4. Characterization of Exemplary Analogs

The configurations, diastereoisomeric excesses, isolated and overall yields of all final sphingosine analogs are listed in Table 6.

This demonstrates a novel and effective route for synthesis of sphingosine analogs starting from racemic, enantiomerically-enriched and enantiopure (>99% e.e.) trans-γ,δ-unsaturated β-hydroxyesters. An efficient enzymatic method utilizing isolated NAD(P)H dependent ketoreductases for the direct and stereoselective synthesis of either enantiomer of aryl γ,δ-unsaturated β-hydroxyesters in excellent optical purity (>99%) with good to excellent conversion has been described. The scaled reaction indicates that the isolated yields are very close to the conversion as monitored by NMR spectroscopy, and offer the same optical purity (>99%). Codexis ketoreductases thus may offer potential for large scale synthesis of either enantiomer of aryl γ,δ-unsaturated-β-hydroxyesters.

Additionally, strategies towards the diastereoselective formation of the hydrazine, and non-reductive eliminative cleavage of the N—N bond is essential to the stereoselective formation of the amino group. Either (3R, 2S) or (3S, 2R)

TABLE 6

| Cmpd. No. | SP Analog | Configuration[a] | d.e.[b] (%) | Isolated Yield (%) | Overall Yield (%) |
|---|---|---|---|---|---|
| 10A | (phenyl-CH=CH-CH(OH)-CH(NHBoc)-CH2OH) | S,R | >99 | 96 | 37 |
| 11B | (4-methylphenyl-CH=CH-CH(OH)-CH(NHBoc)-CH2OH) | S,R | >99 | 94 | 32 |
| 11A | (phenyl-CH=CH-CH(OH)-CH(NHBoc)-CH2OH) | R,S | >99 | 93 | 41 |
| 11B | (4-methylphenyl-CH=CH-CH(OH)-CH(NHBoc)-CH2OH) | R,S | >99 | 95 | 35 |
| 11C | (4-chlorophenyl-CH=CH-CH(OH)-CH(NHBoc)-CH2OH) | racemic, anti | — | 94 | 34 |
| 11D | (4-nitrophenyl-CH=CH-CH(OH)-CH(NHBoc)-CH2OH) | racemic, anti | —r | 92 | 34 |

[a]Assignment of configuration refers to the configuration of carbon-2 and carbon-3;
[b]The percent d.e. was measured by both $^1$HNMR and chiral HPLC.

A solution of compound (10A-10D) and 10 mol % of p-toluenesulfonic acid in 80% EtOH in water was refluxed to provide sphingosine derivatives (11A-11D) in 92-96% yield.

enantiomers of D-erythro-sphingosine analogs are synthesized with excellent diastereoisomeric excesses (>99% d.e.), with no loss of stereochemistry detected over the entire synthesis. The optical purities of final sphingosine analogs depend on the enantiopurity of the trans-γ,δ-unsaturated β-hydroxyesters. Most significantly, this strategy permits the preparation of either enantiomer of a sphingosine derivative and offers an opportunity to incorporate substituents into C-1 to C-5 position for further study.

F. REFERENCES

Hopkins, C. D.; Schmitz, J. C.; Chu, E.; Wipf, P., *Org. Lett.* 2011, 13, 4088-4091.

Li, D.; Carr, G.; Zhang, Y.; Williams, D. E.; Amlani, A.; Bottriell, H.; Mui, A. L. F.; Andersen, R. J., *J. Nat. Prod.* 2011, 74, 1093-1099.

Reiff, E. A.; Nair, S. K.; Narayan Reddy, B. S.; Inagaki, J.; Henri, J. T.; Greiner, J. F.; Georg, G. I., *Tetrahedron Lett.* 2004, 45, 5845-5847.

Schmidt, B.; Kunz, O.; Petersen, M. H., *J. Org. Chem.* 2012, 77, 10897-10906.

Mukaiyama, T., The Directed Aldol Reaction, in: Organic Reactions, John Wiley & Sons, Inc., 2004.

Smrčina, M.; Lorenc, M.; Hanuš, V.; Kočovský, P., *Synlett* 1991, 231-232.

Rimoldi, I.; Pellizzoni, M.; Facchetti, G.; Molinari, F.; Zerla, D.; Gandolfi, R., *Tetrahedron: Asymmetry* 2011, 22, 2110-2116.

Hu, A.; Ngo, H. L.; Lin, W., *Angew. Chem., Int. Ed.* 2004, 43, 2501-2504.

Taber, D. F.; Silverberg, L. J., *Tetrahedron Lett.* 1991, 32, 4227-4230.

Zhou, Y.-G.; Tang, W.; Wang, W.-B.; Li, W.; Zhang, X., *J. Am. Chem. Soc.* 2002, 124, 4952-4953.

Zhang, Z.; Qian, H.; Longmire, J.; Zhang, X., *J. Org. Chem.* 2000, 65, 6223-6226.

Burk, M. J.; Harper, T. G. P.; Kalberg, C. S., *J. Am. Chem. Soc.* 1995, 117, 4423-4424.

Genêt, J. P.; Pfister, X.; Ratovelomanana-Vidal, V.; Pinel, C.; Laffitte, J. A., *Tetrahedron Lett.* 1994, 35, 4559-4562.

Seashore-Ludlow, B.; Saint-Dizier, F.; Somfai, P., *Org. Lett.* 2012, 14, 6334-6337.

Genêt, J. P.; Pinel, C.; Ratovelomanana-Vidal, V.; Mallart, S.; Pfister, X.; De Andrade, M. C. C.; Laffitte, J. A., *Tetrahedron: Asymmetry* 1994, 5, 665-674.

Ohkuma, T.; Koizumi, M.; Doucet, H.; Pham, T.; Kozawa, M.; Murata, K.; Katayama, E.; Yokozawa, T.; Ikariya, T.; Noyori, R., *J. Am. Chem. Soc.* 1998, 120, 13529-13530.

Arai, N.; Azuma, K.; Nii, N.; Ohkuma, T., *Angew. Chem., Int. Ed.* 2008, 47, 7457-7460.

Corey, E. J.; Bakshi, R. K.; Shibata, S., *J. Am. Chem. Soc.* 1987, 109, 5551-5553.

Corey, E. J.; Bakshi, R. K.; Shibata, S.; Chen, C. P.; Singh, V. K., *J. Am. Chem. Soc.* 1987, 109, 7925-7926.

Corey, E. J.; Helal, C. J., *Angew. Chem., Int. Ed.* 1998, 37, 1986-2012.

Kawanami, Y.; Murao, S.; Ohga, T.; Kobayashi, N., *Tetrahedron* 2003, 59, 8411-8414.

Mathre, D. J.; Thompson, A. S.; Douglas, A. W.; Hoogsteen, K.; Carroll, J. D.; Corley, E. G.; Grabowski, E. J. J., *J. Org. Chem.* 1993, 58, 2880-2888.

Greck, C.; Ferreira, F.; Genet, J. P., *Tetrahedron Lett.* 1996, 37, 2031-2034.

Ma, X.; Li, W.; Li, X.; Tao, X.; Fan, W.; Xie, X.; Ayad, T.; Ratovelomanana-Vidal, V.; Zhang, Z., *Chem. Commun.* 2012, 48, 5352-5354.

Genêt, J. P.; Pinel, C.; Ratovelomanana-Vidal, V.; Mallart, S.; Pfister, X.; Bischoff, L.; De Andrade, M. C. C.; Darses, S.; Galopin, C.; Laffitte, J. A., *Tetrahedron: Asymmetry* 1994, 5, 675-690.

Schmidt, B., *J. Org. Chem.* 2004, 69, 7672-7687.

Akutagawa, S., *Appl. Catal.* 1995, A 128, 171-207.

Matsuda, T.; Yamanaka, R.; Nakamura, K., *Tetrahedron: Asymmetry* 2009, 20, 513-557.

Turner, N. J., *Nat. Chem. Biol.* 2009, 5, 568-574.

Zhu, D.; Yang, Y.; Hua, L., *J. Org. Chem.* 2006, 71, 4202-4205.

Kaluzna, I. A.; Matsuda, T.; Sewell, A. K.; Stewart, J. D., *J. Am. Chem. Soc.* 2004, 126, 12827-12832.

Huisman, G. W.; Liang, J.; Krebber, A., *Curr. Opin. Chem. Biol.* 2010, 14, 122-129.

Kalaitzakis, D.; Kambourakis, S.; Rozzell, D. J.; Smonou, I., *Tetrahedron: Asymmetry* 2007, 18, 2418-2426.

Baskar, B.; Pandian, N. G.; Priya, K., Chadha, A., *Tetrahedron: Asymmetry* 2004, 15, 3961-3966.

Schroer, K.; Mackfeld, U.; Tan, I. A. W.; Wandrey, C.; Heuser, F.; Bringer-Meyer, S.; Weckbecker, A.; Hummel, W.; DauBmann, T.; Pfaller, R.; Liese, A.; Lütz, S., *J. Biotechnol.* 2007, 132, 438-444.

Ishihara, K.; Yamaguchi, H.; Adachi, N.; Hamada, H.; Nakajima, N., *Biosci., Biotechnol., Biochem.* 2000, 64, 2099-2103.

Rimoldi, I.; Cesarotti, E.; Zerla, D.; Molinari, F.; Albanese, D.; Castellano, C.; Gandolfi, R., *Tetrahedron: Asymmetry* 2011, 22, 597-602.

Kambourakis, S.; Rozzell, J. D., *Tetrahedron* 2004, 60, 663-669.

Zhu, D.; Mukherjee, C.; Rozzell, J. D.; Kambourakis, S.; Hua, L., *Tetrahedron* 2006, 62, 901-905.

Kalaitzakis, D.; Rozzell, J. D.; Kambourakis, S.; Smonou, I., *Org. Lett.* 2005, 7, 4799-4801.

Padhi, S. K.; Chadha, A., *Tetrahedron: Asymmetry* 2005, 16, 2790-2798.

Saravanan, T.; Selvakumar, R.; Doble, M.; Chadha, A., *Tetrahedron: Asymmetry* 2012, 23, 1360-1368.

Kirschner, D.; Jaramillo, M.; Green, T.; Hapiot, F.; Leclercq, L.; Bricout, H.; Monflier, E., *J. Mol. Catal. A: Chem.* 2008, 286, 11-20.

Moorhoff, C. M., *Synth. Commun.* 2003, 33, 2069-2086.

Hoye, T. R.; Jeffrey, C. S.; Shao, F., *Nat. Protoc.* 2007, 2, 2451-2458.

Vandengoorbergh, J. A. M.; Vandergen, A., *Tetrahedron Lett.* 1980, 21, 3621-3624.

Svendsen, A.; Boll, P. M., *Tetrahedron* 1973, 29, 4251-4258.

Bodalski, R.; Pietrusiewicz, K. M.; Monkiewicz, J.; Koszuk, J., *Tetrahedron Lett.* 1980, 21, 2287-2290.

Moorhoff, C. M.; Schneider, D. F., *Tetrahedron Lett.* 1987, 28, 559-562.

du Pisani, C.; Schneider, C. F.; Venter, P. C. R., *Synth. Commun.* 2002, 32, 305-314.

Hannun, Y. A.; Obeid, L. M., *Journal of Biological Chemistry* 2002, 277, 25847-25850.

Ogretmen, B.; Hannun, Y. A., *Nature Reviews Cancer* 2004, 4, 604-616.

Perry, D. K.; Carton, J.; Shah, A. K.; Meredith, F.; Uhlinger, D. J.; Hannun, Y. A., *Journal of Biological Chemistry* 2000, 275, 9078-9084.

Hannun, Y. A.; Obeid, L. M., *Nat Rev Mol Cell Biol* 2008, 9, 139-150.

Pyne, N. J.; Pyne, S., *Nat Rev Cancer* 2010, 10, 489-503.

Spiegel, S.; Milstien, S., *Nat Rev Mol Cell Bio* 2003, 4, 397-407.

Milstien, S.; Spiegel, S., *Cancer Cell* 2006, 9, 148-150.
Wymann, M. P.; Schneiter, R., *Nat Rev Mol Cell Biol* 2008, 9, 162-176.
Reynolds, C. P.; Maurer, B. J.; Kolesnick, R. N., *Cancer Letters* 2004, 206, 169-180.
Radin, N. S., *Biochem J* 2003, 371, 243-256.
Edsall, L. C.; Van Brocklyn, J. R.; Cuvillier, O.; Kleuser, B.; Spiegel, S., *Biochemistry-Us* 1998, 37, 12892-12898.
Yatomi, Y.; Ruan, F.; Megidish, T.; Toyokuni, T.; Hakomori, S.-i.; Igarashi, Y., *Biochemistry-Us* 1996, 35, 626-633.
Ahn, E. H.; Chang, C.-C.; Schroeder, J. J., *Experimental Biology and Medicine* 2006, 231, 1664-1672.
Ahn, E. H.; Schroeder, J. J., *Anticancer Res* 2010, 30, 2881-2884.
Lim, K. G.; Tonelli, F.; Li, Z. G.; Lu, X. Q.; Bittman, R.; Pyne, S.; Pyne, N.J., *Journal of Biological Chemistry* 2011, 286, 18633-18640.
Murakami, T.; Furusawa, K.; Tamai, T.; Yoshikai, K.; Nishikawa, M., *Bioorg Med Chem Lett* 2005, 15, 1115-1119.
Moreno, M.; Murruzzu, C.; Riera, A., *Organic Letters* 2011, 13, 5184-5187.
Lim, H.-S.; Park, J.-J.; Ko, K.; Lee, M.-H.; Chung, S.-K., *Bioorg Med Chem Lett* 2004, 14, 2499-2503.
Paugh, S. W.; Paugh, B. S.; Rahmani, M.; Kapitonov, D.; Almenara, J. A.; Kordula, T.; Milstien, S.; Adams, J. K.; Zipkin, R. E.; Grant, S.; Spiegel, S., *Blood* 2008, 112, 1382-1391.
Pyne, S.; Bittman, R.; Pyne, N.J., *Cancer research* 2011, 71, 6576-6582.
Kumar, P.; Dubey, A.; Puranik, V. G., *Organic & Biomolecular Chemistry* 2010, 8, 5074-5086.
Kobayashi, S.; Hayashi, T.; Kawasuji, T., *Tetrahedron Letters* 1994, 35, 9573-9576.
van den Berg, R. J. B. H. N.; Korevaar, C. G. N.; van der Marel, G. A.; Overkleeft, H. S.; van Boom, J. H., *Tetrahedron Letters* 2002, 43, 8409-8412.
Cai, Y.; Ling, C.-C.; Bundle, D. R., *Organic & Biomolecular Chemistry* 2006, 4, 1140-1146.
Llaveria, J.; Díaz, Y.; Matheu, M. I.; Castillón, S., *Organic Letters* 2008, 11, 205-208.
van den Berg, R. J. B. H. N.; van den Elst, H.; Korevaar, C. G. N.; Aerts, J. M. F. G.; van der Marel, G. A.; Overkleeft, H. S., *European Journal of Organic Chemistry* 2011, 2011, 6685-6689.
Yang, H.; Liebeskind, L. S., *Organic Letters* 2007, 9, 2993-2995.
Chandrasekhar, S.; Saritha, B.; Jagadeshwar, V.; Prakash, S. J., *Tetrahedron: Asymmetry* 2006, 17, 1380-1386.
Herold, P., *Helv Chim Acta* 1988, 71, 354-362.
Van Overmeire, I.; Boldin, S. A.; Dumont, F.; Van Calenbergh, S.; Slegers, G.; De Keukeleire, D.; Futerman, A. H.; Herdewijn, P., *J Med Chem* 1999, 42, 2697-2705.
Wong, L.; Tan, S. S. L.; Lam, Y.; Melendez, A. J., *J Med Chem* 2009, 52, 3618-3626.
Zipkin, R. E. W. P. A.; Spiegel, S. R. V. A.; Adams, J. K. F. W. P. A. US 2010/0035959 A1, 2010.
Radunz, H.-E.; Devant, R. M.; Eiermann, V., *Liebigs Annalen der Chemie* 1988, 1988, 1103-1105.
Nimkar, S.; Menaldino, D.; Merrill, A. H.; Liotta, D., *Tetrahedron Letters* 1988, 29, 3037-3040.
Garner, P.; Park, J. M.; Malecki, E., *The Journal of Organic Chemistry* 1988, 53, 4395-4398.
Dondoni, A.; Fantin, G.; Fogagnolo, M.; Medici, A., *Journal of the Chemical Society, Chemical Communications* 1988, 10-12.
Carreira, E. M.; Singer, R. A.; Lee, W. S., *Journal of the American Chemical Society* 1994, 116, 8837-8838.
Dai, Z.; Guillemette, K.; Green, T. K., *Molecular Catalysis B: Enzymatic*. (In press)
Girard, A.; Greck, C.; Ferroud, D.; Genêt, J. P., *Tetrahedron Letters* 1996, 37, 7967-7970.
Labeeuw, O.; Phansavath, P.; Genêt, J.-P., *Tetrahedron Letters* 2003, 44, 6383-6386.
Greck, C.; Bischoff, L.; Ferreira, F.; Pinel, C.; Piveteau, E.; Genet, J. P., *Synlett* 1993, 475-477.
Greck, C.; Genet, J. P., *Synlett* 1997, 741-&.
Kim, J.; De Castro, K. A.; Lim, M.; Rhee, H., *Tetrahedron* 2010, 66, 3995-4001.
Chaudhuri, S. K.; Saha, M.; Saha, A.; Bhar, S., *Beilstein journal of organic chemistry* 2010, 6, 748-55.
Brown, M. S.; Rapoport, H., *The Journal of Organic Chemistry* 1963, 28, 3261-3263.
Magnus, P.; Garizi, N.; Seibert, K. A.; Ornholt, A., *Organic Letters* 2009, 11, 5646-5648.

What is claimed is:

1. A synthetic method comprising
a) providing a first compound having the structure

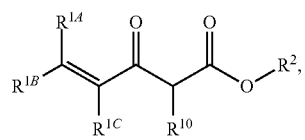

b) reacting the first compound in the presence of a ketoreductase, thereby forming a second compound having the structure

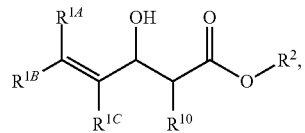

wherein each of $R^{1A}$, $R^{1B}$, and $R^{1C}$ is independently selected from hydrogen, aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, nitro, cyano, —C(O)O—$R^7$, —C(O)—$R^7$, $^-COR^7$, and —O$R^7$, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, $^-COR^7$, and —O$R^7$, wherein at least one of $R^{1A}$ and $R^{1B}$ is not hydrogen,
wherein $R^2$ is selected from alkyl, alkenyl, alkynyl, haloalkyl, haloalkenyl, haloalkynyl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, ⁻COR$^7$, and —OR$^7$, wherein each $R^7$ is independently selected from hydrogen, alkyl, haloalkyl, polyhaloalkyl, alkylamino, dialkylamino, -alkyl-aryl, and -alkyl-heterocyclyl, wherein $R^{10}$ is selected from hydrogen, alkyl, alkenyl, or alkynyl, and wherein the ketoreductase is selected from 101, 119, 130, NADH-101, NADH-110, P1-B02, P1-B05, P1-B10, P1-B12, P1-C01, P1-H08, P2-B02, P2-C11, P2-D03, P2-D11, P2-D12, P2-G03, P3-G09, and P3-H12.

2. The synthetic method of claim 1, wherein $R^{1A}$ is hydrogen and $R^{1B}$ is selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, and haloalkyl.

3. The synthetic method of claim 1, wherein $R^{1C}$ is hydrogen.

4. The synthetic method of claim 1, wherein $R^2$ is selected from alkyl, alkenyl, and alkynyl.

5. The synthetic method of claim 1, wherein the ketoreductase is selected from 130, NADH-101, P3-G09, and P3-H12.

6. The synthetic method of claim 1, wherein the second compound is selected from

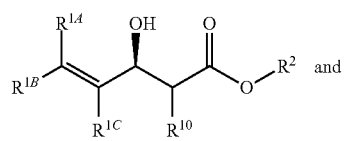

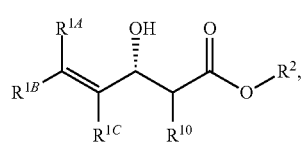

and is formed in at least 90% enantiomeric excess.

7. The synthetic method of claim 1, wherein the second compound has the structure

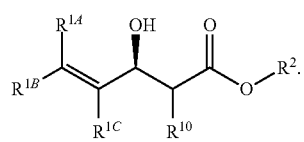

8. The synthetic method of claim 7, wherein the method further comprises aminating the second compound to form a third compound having the structure

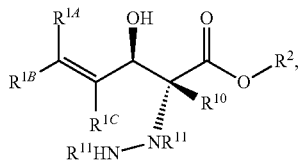

wherein each $R^{11}$ is independently an amine protecting group.

9. The synthetic method of claim 8, wherein the ester of the third compound is reduced to form an alcohol in a fourth compound.

10. The synthetic method of claim 9, wherein the alcohols in the fourth compound are protected, thereby forming a fifth compound having the structure

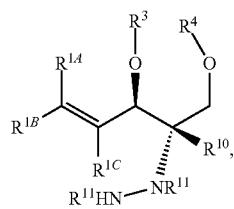

wherein $R^3$ and $R^4$ are alcohol protecting groups, or wherein $R^3$ and $R^4$ are linked together to form an alcohol protecting group.

11. The synthetic method of claim 10, wherein the method further comprises cleaving the N—N bond in the fifth compound, thereby forming a sixth compound.

12. The synthetic method of claim 1, wherein providing the first compound comprises reacting a compound having the structure

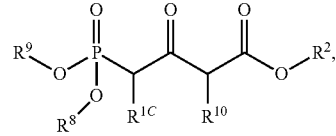

with an aldehyde to form the first compound, wherein each of $R^8$ and $R^9$ is independently selected from alkyl, alkenyl, and alkynyl.

13. A synthetic method comprising aminating a second compound having the structure

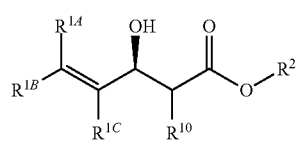

to form a third compound having the structure

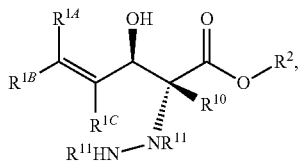

wherein each of $R^{1A}$, $R^{1B}$, and $R^{1C}$ is independently selected from hydrogen, aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, nitro, cyano, —C(O)O—$R^7$, —C(O)—$R^7$, ⁻COR$^7$, and —OR$^7$, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, ⁻COR$^7$, and —OR$^7$, wherein $R^2$ is selected from alkyl, alkenyl, alkynyl, haloalkyl, haloalkenyl, haloalkynyl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, ⁻COR$^7$, and —OR$^7$, wherein each $R^7$ is independently selected from hydrogen, alkyl, haloalkyl, polyhaloalkyl, alkylamino, dialkylamino, -alkyl-aryl, and -alkyl-heterocyclyl, wherein $R^{10}$ is selected from hydrogen, alkyl, alkenyl, or alkynyl, and wherein each $R^{11}$ is an amine protecting group.

14. The synthetic method of claim 13, wherein

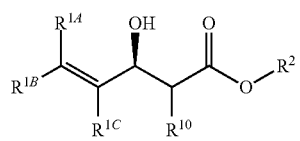

is formed from

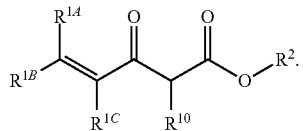

15. The synthetic method of claim 13, wherein the ester of the third compound is reduced to form an alcohol in a fourth compound.

16. The synthetic method of claim 15, wherein the alcohols in fourth compound are protected, thereby forming a fifth compound having the structure

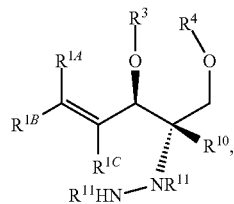

wherein $R^3$ and $R^4$ are alcohol protecting groups, or wherein $R^3$ and $R^4$ are linked together to form an alcohol protecting group.

17. The synthetic method of claim 16, wherein the fifth compound has the structure

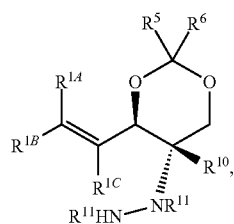

wherein each of $R^5$ and $R^6$ is independently selected from hydrogen, alkyl, and aryl, or wherein $R^5$ and $R^5$ are linked together to form a cycloalkyl, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, ⁻COR$^7$, and —OR$^7$.

18. The synthetic method of claim 17, wherein the method further comprises cleaving the N—N bond in the fifth compound, thereby forming a sixth compound.

19. A synthetic method comprising
a) providing a first compound having the structure

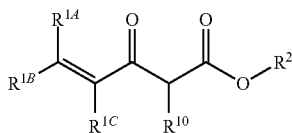

wherein each of $R^{1A}$, $R^{1B}$, and $R^{1C}$ is independently selected from hydrogen, aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, nitro, cyano, —C(O)O—$R^7$, —C(O)—$R^7$, —COR$^7$, and —OR$^7$, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, $^-$COR$^7$, and —OR$^7$,
wherein $R^2$ is selected from alkyl, alkenyl, alkynyl, haloalkyl, haloalkenyl, haloalkynyl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, $^-$COR$^7$, and —OR$^7$,
wherein each $R^7$ is independently selected from hydrogen, alkyl, haloalkyl, polyhaloalkyl, alkylamino, dialkylamino, -alkyl-aryl, and -alkyl-heterocyclyl,
wherein $R^{10}$ is selected from hydrogen, alkyl, alkenyl, or alkynyl;
b) reacting the first compound in the presence of a ketoreductase, thereby forming a second compound having the structure

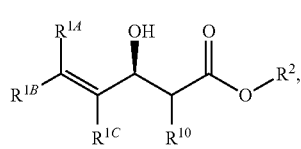

wherein the ketoreductase is 130, NADH-101, P3-G09, or P3-H12;

c) aminating the second compound to form a third compound having the structure

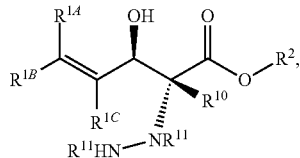

wherein $R^{11}$ is an amine protecting group, d) reducing the ester in the third compound to form an alcohol in a fourth compound;

e) protecting the alcohols in the fourth compound to form a fifth compound; and f) cleaving the N—N bond in the fifth compound to form a sixth compound having the structure

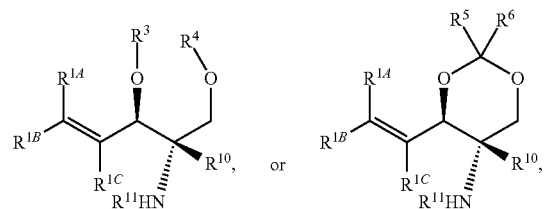

wherein $R^3$ and $R^4$ are alcohol protecting groups, or wherein $R^3$ and $R^4$ are linked together to form an alcohol protecting group, and wherein each of $R^5$ and $R^6$ is independently selected from hydrogen, alkyl, and aryl, or wherein $R^5$ and $R^5$ are linked together to form a cycloalkyl, and is substituted with 0, 1, 2, or 3 groups selected from aryl, cycloalkyl, cycloalkenyl, heterocyclyl, heteroaryl, -alkyl-aryl, -alkenyl-aryl, alkynyl-aryl, -alkyl-cycloalkyl, -alkenyl-cycloalkyl, alkynyl-cycloalkyl, alkyl-heterocyclyl, -alkenyl-heterocyclyl, alkynyl-heterocyclyl, -alkyl-heteroaryl, -alkenyl-heteroaryl, alkynyl-heteroaryl, alkyl, alkenyl, alkynyl, haloalkyl, haloalkenyl, haloalkynyl, alkoxy, aryloxy, mono- or di-alkylamino, a mono- or diaryl amino, hydroxyl, thiol, nitro, cyano, amino, halo, —C(O)O—$R^7$, —C(O)—$R^7$, $^-$COR$^7$, and —OR$^7$.

20. The synthetic method of claim 19, wherein

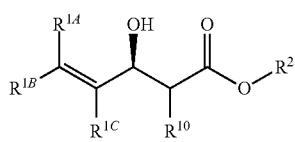

is formed at least 90% enantiomeric excess.

* * * * *